(12) United States Patent
Dempcy et al.

(10) Patent No.: US 7,751,982 B2
(45) Date of Patent: *Jul. 6, 2010

(54) TM LEVELING METHODS

(75) Inventors: Robert O. Dempcy, Kirkland, WA (US); Alexander A. Gall, Woodinville, WA (US); Sergey G. Lokhov, Kirkland, WA (US); Irina A. Afonina, Mill Creek, WA (US); Igor V. Kutyavin, Woodinville, WA (US); Nicolaas M. J. Vermeulen, Woodinville, WA (US)

(73) Assignee: Elitech Holding B.V. (NL)

( * ) Notice: Subject to any disclaimer, the term of this patent is extended or adjusted under 35 U.S.C. 154(b) by 704 days.

This patent is subject to a terminal disclaimer.

(21) Appl. No.: 10/672,429

(22) Filed: Sep. 26, 2003

(65) Prior Publication Data

US 2005/0075491 A1    Apr. 7, 2005

Related U.S. Application Data

(60) Continuation of application No. 10/032,307, filed on Dec. 21, 2001, now Pat. No. 6,683,173, which is a continuation of application No. 09/796,988, filed on Feb. 28, 2001, now Pat. No. 7,045,610, and a continuation-in-part of application No. 09/724,959, filed on Nov. 28, 2000, now Pat. No. 6,949,367, which is a continuation-in-part of application No. 09/640,953, filed on Aug. 16, 2000, now Pat. No. 6,492,346, which is a division of application No. 09/054,832, filed on Apr. 3, 1998, now Pat. No. 6,312,894, said application No. 09/724,959 is a continuation-in-part of application No. 09/431,385, filed on Nov. 1, 1999, now Pat. No. 6,485,906, which is a continuation of application No. 09/054,830, filed on Apr. 3, 1998, now Pat. No. 6,127,121.

(60) Provisional application No. 60/186,046, filed on Mar. 1, 2000.

(51) Int. Cl.
*G06F 19/00* (2006.01)
*C12Q 1/68* (2006.01)

(52) U.S. Cl. .............................. 702/19; 435/6

(58) Field of Classification Search ................. None
See application file for complete search history.

(56) References Cited

U.S. PATENT DOCUMENTS

| | | | |
|---|---|---|---|
| 3,996,345 A | 12/1976 | Ullman et al. | |
| 4,351,760 A | 9/1982 | Khanna et al. | |
| 4,358,535 A | 11/1982 | Falkow et al. | |
| 4,683,195 A | 7/1987 | Mullis et al. | |
| 4,683,202 A | 7/1987 | Mullis | |
| 4,800,159 A | 1/1989 | Mullis et al. | |
| 4,868,105 A | 9/1989 | Urdea et al. | |
| 5,124,246 A | 6/1992 | Urdea et al. | |
| 5,177,196 A | 1/1993 | Meyer, Jr. et al. | |
| 5,210,015 A | 5/1993 | Gelfand et al. | |
| 5,419,966 A | 5/1995 | Reed et al. | |
| 5,449,767 A | 9/1995 | Ward et al. | |
| 5,484,908 A | 1/1996 | Froehler et al. | |
| 5,492,806 A | 2/1996 | Drmanac et al. | |
| 5,512,667 A | 4/1996 | Reed et al. | |
| 5,525,464 A | 6/1996 | Drmanac et al. | |
| 5,556,749 A | 9/1996 | Mitsuhashi et al. | |
| 5,578,467 A | 11/1996 | Schuster et al. | |
| 5,585,481 A | 12/1996 | Arnold, Jr. et al. | |
| 5,594,121 A | 1/1997 | Froehler et al. | |
| 5,645,985 A | 7/1997 | Froehler et al. | |
| 5,696,251 A | 12/1997 | Arnold, Jr. et al. | |
| 5,736,626 A | 4/1998 | Mullah et al. | |
| 5,801,155 A | 9/1998 | Kutyavin et al. | |
| 5,824,796 A | 10/1998 | Petrie et al. | |
| 5,849,482 A | 12/1998 | Meyer et al. | |
| 5,869,251 A | 2/1999 | Schuster et al. | |
| 5,942,610 A | 8/1999 | Nelson et al. | |
| 6,084,102 A | 7/2000 | Kutyavin et al. | |
| 6,127,121 A | 10/2000 | Meyer et al. | |
| 6,143,877 A | 11/2000 | Meyer et al. | |
| 6,156,501 A | 12/2000 | McGall et al. | |
| 6,312,894 B1 | 11/2001 | Hedgpeth et al. | |
| 6,339,147 B1 | 1/2002 | Lukhtanov et al. | |
| 6,403,319 B1 * | 6/2002 | Lizardi et al. ........... | 435/6 |
| 6,426,408 B1 | 7/2002 | Kutyavin et al. | |
| 6,683,173 B2 | 1/2004 | Dempcy et al. | |

FOREIGN PATENT DOCUMENTS

EP    1103910 A1    5/2001

(Continued)

OTHER PUBLICATIONS

Griffin et al. (Analytical Biochemistry, vol. 260, pp. 56-63, 1998).*

(Continued)

*Primary Examiner*—John S Brusca
(74) *Attorney, Agent, or Firm*—Jackson Walker L.L.P.

(57) ABSTRACT

Methods for designing an oligonucleotide sequence having a selected duplex stability are provided wherein the oligonucleotide portion comprises at least one modified base selected from universal bases, unsubstituted and 3-substituted pyrazolo[3,4-d]pyrimidines and 5-substituted pyrimidines, and optionally having attached minor groove binders and reporter groups.

20 Claims, 6 Drawing Sheets

FOREIGN PATENT DOCUMENTS

| | | |
|---|---|---|
| WO | WO 84/03285 | 8/1984 |
| WO | WO 90/03370 | 5/1990 |
| WO | WO 92/10588 | 6/1992 |
| WO | WO 96/17957 | 6/1996 |
| WO | WO 96/32496 | 10/1996 |
| WO | WO 97/46313 | 12/1997 |
| WO | WO 98/49180 | 11/1998 |
| WO | WO 99/37085 | 7/1999 |
| WO | WO 99/51621 | 10/1999 |
| WO | WO 99/51775 | 10/1999 |
| WO | WO 00/06771 | 2/2000 |
| WO | WO 02/12263 | 2/2002 |

OTHER PUBLICATIONS

Kutyavin et al. (Nucleic Acids Research, vol. 28, pp. 655-661, 2000).*
Martin et al. Base pairing involving deoxyinosine: implications for probe design Nucleic Acids Research vol. 13, pp. 8927-8938 (1985).*
Loakes et al. 3-Nitropyrrole and 5-nitroindole as universal bases in promers for DNA sequencing and PCR. Nucleic Acids Research vol. 23 pp. 2361-2366 (1995).*
Kutyavin et al. Oligonucleotides with conjugated dihydropyrroloindole tripeptides: base composition and backbone effects on hybridization Nucleic Acids Research vol. 25 pp. 3718-3723 (1997).*
U.S. Appl. No. 09/457,616, filed Dec. 8, 1999, Reed et al.
Lyamichev et al., Nature Biotechnol., 17:292-296 (1999).
Mueller et al., Histochem, Cell Biol., 108:431-437 (1997).
Nielsen et al. Science, 254: 1497-1500 (1991).
Owczarzy et al. Biopolymers, 44:217-239 (1997).
Palissa et al., Z. Chem., 27:216 (1987).
Pastinen T. et al., Genome Res., 10:1031-42 (2000).
Ramzaeva et al., Helv. Chim, Acta, 80:1809-1822 (1997).
Reddy, et al., Pharmacol. Therap., 84:1-111 (1999).
Santalucia et al., Biochem, 36:10581-10595 (1997).
Scheit, Nucleotide Analogs, John Wiley, New York (1980).
Schutz et al., Biotechniques, 27:1218-22 (1999).
Seela et al., J. Chem. Soc. Perkin Trans., I:479-488 (1999).
Seela et al., Nucl. Acids Res., 28:3224-3232 (2000).
Singh et al., Chem. Comm., 455-456 (1998).
Smith et al., Int. J. Oncol., 17:841-850 (2000).
Sugimoto et al., Biochem 34:11211-11216 (1995).
Taton, T.A. et al., Science, 289:1757-1760 (2000).
Taylor et al., Tetrahedron, 48(37):8089-8100 (1992).
Uhlman et al., Chemical Reviews, 90:543-584 (1990).
Uhlmann et al. Angew. Chem. Ing. Ed. 37:2796-2823 (1998).
Van Ness et al., Nucleic Acids Res., 19:5143-5151 (1991).
Vincent et al. J. Org. Chem., 64:991-997 (1999).
Walker, W.L. et al., Biopolymers, 44:323-334 (1997).
Wemmer, D.E. et al., Current Opinion in Structural Biology, 7:355-361 (1997).
Wengel J., Acc. Chem Res., 32:301-310 (1998).
Zhang et al., Nat. Biotechnol., 18:862-867 (2000).
Zimmer, C et al., U. Pros Biophys. Molec. Bio. 47:31-112 (1986).
Breslauer, K. J. et al.: "Predicting DNA duplex stability from the base sequence"; Proc. Nat. Acad. Sci.; 83:3746-3750 (1986).

Chen, H. et al.: "Computer program for calculating the melting temperature of degenerate oligonucleotides used in PCR or hybridization"; BioTechniques; 22:6:1158-1160 (1997).
Le Novere, N.: "Melting, computing the melting temperature of nucleic acid duplex" Bioinformatics; 17:12:1226-1227 (2001).
U.S. Appl. No. 10/302,607, filed Nov. 20, 2002, Petrie et al.
Clercq, E.D. et al. "Nucleic Acid Related Compounds. 40. Synthesis and Biological Activities of 5-Alkynyluracil Nucleosides," J. Med. Chem., vol. 26, No. 5:661-666 (1983).
Cruickshank, K.A. et al. "Oligonucleotide Labelling: A Concise Synthesis Of A Modified Thymidine Phosphoramidite," Tetrahedron Letters, vol. 29 No. 41, pp. 5221-5224 (1988).
Graham, D. et al. "DNA duplexes stabilized by modified monomer residues: synthesis and stability," J. Chem. Soc., Perkin Trans., 1:1131-1138 (1998).
Hobbs, F. W., Jr. "Palladium-Catalyzed Synthesis of Alkynylamino Nucleosides. A Universal Linker for Nucleic Acids," J. Org. Chem., 54:3420-3422 (1989).
Robins, M.J. et al. "Nucleic Acid Related Compounds. 39. Efficient Conversion of 5-Iodo to 5-Alkynyl and Derived 5-Substituted Uracil Bases and Nucleosides," J. Org. Chem., 48:1854-1862 (1983).
Seela, F. et al. "131. 8-Aza-7-deaza-2'-deoxyguanosine: Phosphoramidite Synthesis and Properties of Octanucleotides," Helvetica Chimica Aca, vol. 71:1191-1197 (1988).
Seela, F. et al. "8-AZA-7-Deazapurine DNA: Synthesis And Duplex Stability Of Oligonucleotides Containing 7-Substituted Bases," Nucleosides & Nucleotides, 18(6&7):1399-1400 (1999).
Seela, F. et al. "Duplex Stability Of Oligonucleotides Containing 7-Substituted 7-DEAZA- and 8-AZA-7-Deazapurine NucleosideS," Nucleosides & Nucleotides, 16(7-9):963-966 (1997).
Seela, F. et al. "Oligonucleotides Containing Pyrazolo [3,4-d] pyrimidines: The Influence of 7-Substituted 8-Aza-7-deaza-2'-deoxyguanosines on the Duplex Structure and Stability," Helveticā Chimica Acta, vol. 82:1640-1655 (1999).
Seela, F. et al. "Synthesis of 7-alkynylated 8-aza-7-deaza-2'-deoxyadenosines via the Pd-catalysed cross-coupling reaction," J. Chem. Soc., Perkin Trans., 1:3233-3239 (1998).
Seela, F. et al. "The Influence of Modified Purine Bases on the Stability of Parallel DNA," Bioorganic & Medicinal Chemistry Letters, 10:289-292 (2000).
Balow et al., Nuc. Acid Res., 26:3350-3357 (1998).
Beaucage et al., Tetrahedron 48:2223-2311 (1992).
Blake et al., Bioinformatics, 15:370-5 (1999).
Bolli et al., Nucl. Acids Res., 24:4660-4667 (1996).
Capaldi et al., Nuc. Acids Res., 28:E21 (2000).
Chen et al. Nucleic Acids Res. 23:2661-2668 (1995).
Draper et al., Biochemistry 19:1774-1791 (1980).
Eisen, et al., Methods in Enzymology, 303:179-205 (1999).
Flanagan et al., Nat Biotechnol., 14:1139-1145, (1996).
Geisen et al. Nucl. Acids Res., 26:5004-5006 (1998).
Hacia et al., J. Mol. Genet., 36:730-736 (1999).
Hall et al., PNAS 97:8272-77 (2000).
Heid et al., Genome Res. 6:986-994 (1996).
J. Chromatogr., B. Biomed. Sci. Appl. 739:139-150 (2000).
Livak et al., PCT Meth. App. 4:357-362 (1995).
Lohkov, S.G., FEBS Letters 420:134-138 (1997).

* cited by examiner

PPPG

HOPPPG  R = OH
NH₂PPPG  R = NH₂

(NH₂)₂PPPA (NH₂)₂PPPAOH  R = OH
(NH₂)₂PPPANH₂  R = NH₂

PPPA

HOPPPA  R = OH
NH₂PPPA  R = NH₂

PU  R = H
HOPU  R = OH

PC  R = H
HOPC  R = OH
NH₂PC  R = NH₂

A   Six Gs substituted with PPG (tg*g*g*g*g*g*ccttggcggctacg)

B   One G substituted with PPG (tgggg*ggccttggcggctacg)

C   No G substituted with PPG (tggggggccttggcggctacg)

TM LEVELING METHODS

CROSS-REFERENCES TO RELATED APPLICATIONS

This application is a continuation of U.S. application Ser. No. 10/032,307 filed Dec. 21, 2001, now U.S. Pat. No. 6,683,173, which is a continuation of U.S. application Ser. No. 09/796,988, filed Feb. 28, 2001, now, U.S. Pat. No. 7,045,610, which claims the benefit of Provisional Application Ser. No. 60/186,046, filed Mar. 1, 2000; and is a continuation-in-part of Ser. No. 09/724,959, filed Nov. 28, 2000; which is a continuation-in-part of U.S. application Ser. No. 09/640,953, filed Aug. 16, 2000; which is a division of U.S. application Ser. No. 09/054,832, filed Apr. 3, 1998; U.S. application Ser. No. 09/724,959 is a continuation-in-part of U.S. application Ser. No. 09/431,385, filed Nov. 1, 1999; which is a continuation of U.S. application Ser. No. 09/054,830, filed Apr. 3, 1998, now U.S. Pat. No. 6,127,121; the disclosures of each being incorporated herein by reference.

STATEMENT AS TO RIGHTS TO INVENTIONS MADE UNDER FEDERALLY SPONSORED RESEARCH AND DEVELOPMENT

Not applicable.

BACKGROUND OF THE INVENTION

This application is in the field of molecular biology relating to the use of oligonucleotides as probes and primers in liquid, solid and mixed phase assays. The application further relates to the use of modified nucleic acid bases and modified oligonucleotides to improve the hybridization properties and discriminatory abilities of oligonucleotides that are used in arrays and as probes and primers.

Many techniques currently in use in molecular biology utilize oligonucleotides as probes and/or primers. It is often advantageous, in the practice of these techniques, to be able to distinguish between two or more sequences which are related but which differ by one or more nucleotides. For example, many mutations of clinical significance differ by only a single nucleotide from the wild-type sequence. Polymorphisms in mammalian genomes are also often characterized by sequence differences of one or a few nucleotides. The ability to make such a distinction is known as mismatch discrimination. In practical terms, mismatch discrimination describes the property by which a defined sequence oligonucleotide, at a given stringency, hybridizes strongly (one manifestation of which is that the hybrids have a high melting temperature) to a target sequence with which it is complementary along its entire length (a perfect hybrid or perfect match), but hybridizes detectably more weakly to a target sequence that is non-complementary to the sequence of the oligonucleotide at one or a few nucleotides (a mismatch). The differences in hybridization strength are such that a particular stringency can be selected at which a perfect match is detectable as a hybrid and a mismatch fails to form a hybrid.

In a nucleic acid duplex, each base pair contributes to stability. Hence, the shorter the duplex, the greater the relative contribution of each individual base pair to the stability of the duplex. As a result, the difference in stability between a perfect match and a mismatch will be greater for shorter oligonucleotides. However, short oligonucleotides hybridize weakly, even to a perfectly complementary sequence, and thus must be hybridized under conditions of reduced stringency. Thus, the potential discriminatory power of short oligonucleotides cannot be easily realized except under conditions of low stringency.

What is needed in the art are new methods for mismatch discrimination, particularly for single-nucleotide mismatches, under conditions of high stringency; for example, at the elevated temperatures characteristic of most nucleic acid amplification reactions. Surprisingly, the present invention provides such methods, along with new reagents and compositions which can be used in the methods.

SUMMARY OF THE INVENTION

The present invention provides a number of modified oligonucleotides found to have exceptional properties and usefulness in a variety of assays. Accordingly, the present invention also provides methods for using the modified oligonucleotides described herein.

In one aspect, the present invention provides modified oligonucleotides having at least two bases selected from unsubstituted and 3-substituted pyrazolo[3,4-d]pyrimidine bases. In preferred embodiments, the oligonucleotides having modified bases will further comprise other moieties such as detectable labels, fluorescence and chemiluminescence quenchers and/or minor groove binders and/or other types of modified bases or base analogs.

In another aspect, the present invention provides modified oligonucleotides having at least one 5-substituted pyrimidine base and at least one 3-substituted pyrazolo[3,4-d]pyrimidine base. In preferred embodiments, these modified oligonucleotides will further comprise other moieties (as above) such as detectable labels, fluorescence and chemiluminescence quenchers and/or minor groove binders.

In yet another aspect, the present invention provides methods for distinguishing polynucleotides having related sequences.

In still another aspect, the present invention provides methods for detecting the presence of a target sequence in a polynucleotide.

In still other aspects, the present invention provides methods for primer extension, and methods for determining the nucleotide sequence of a polynucleotide.

In related aspects, the present invention provides methods for examining gene expression in a cell, and methods for identifying a mutation or polymorphism in a target sequence of a gene of interest.

In still another aspect, the present invention provides a number of modified bases that are useful in preparing modified oligonucleotides for the methods described herein and other conventional assays and methods.

In yet another aspect, the present invention provides modified oligonucleotide arrays wherein the array members have $T_m$s within about 1-2° C. and lengths within 1-2 bases from each other. Methods are also provided for determining sequences of the array members.

DESCRIPTION OF THE INVENTION

Abbreviations and Definitions

Figure 1A:
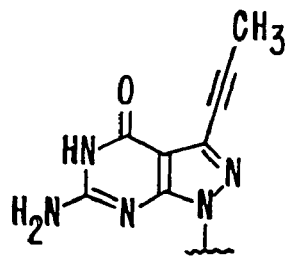
FIGS. 1A and 1B provide structures for several modified bases and their abbreviations. The wavy line is used to denote the position of an attached sugar moiety (unprotected, protected, activated and the like).
Figure 1A:
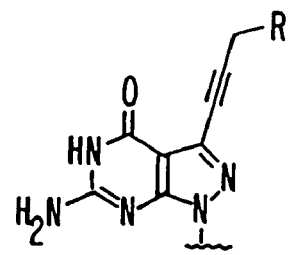
Figure 1A:
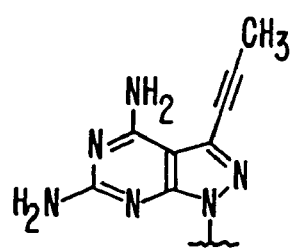
Figure 1A:
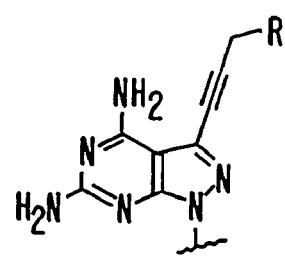
Figure 1A:
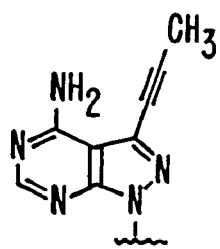
Figure 1A:
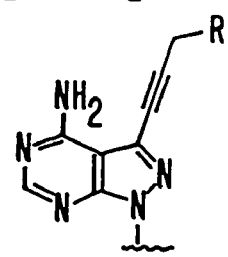
Figure 1A:
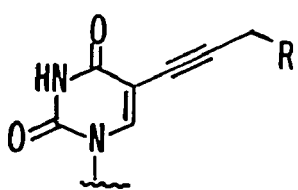
Figure 1A:
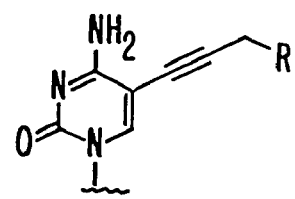
Figure 1B:
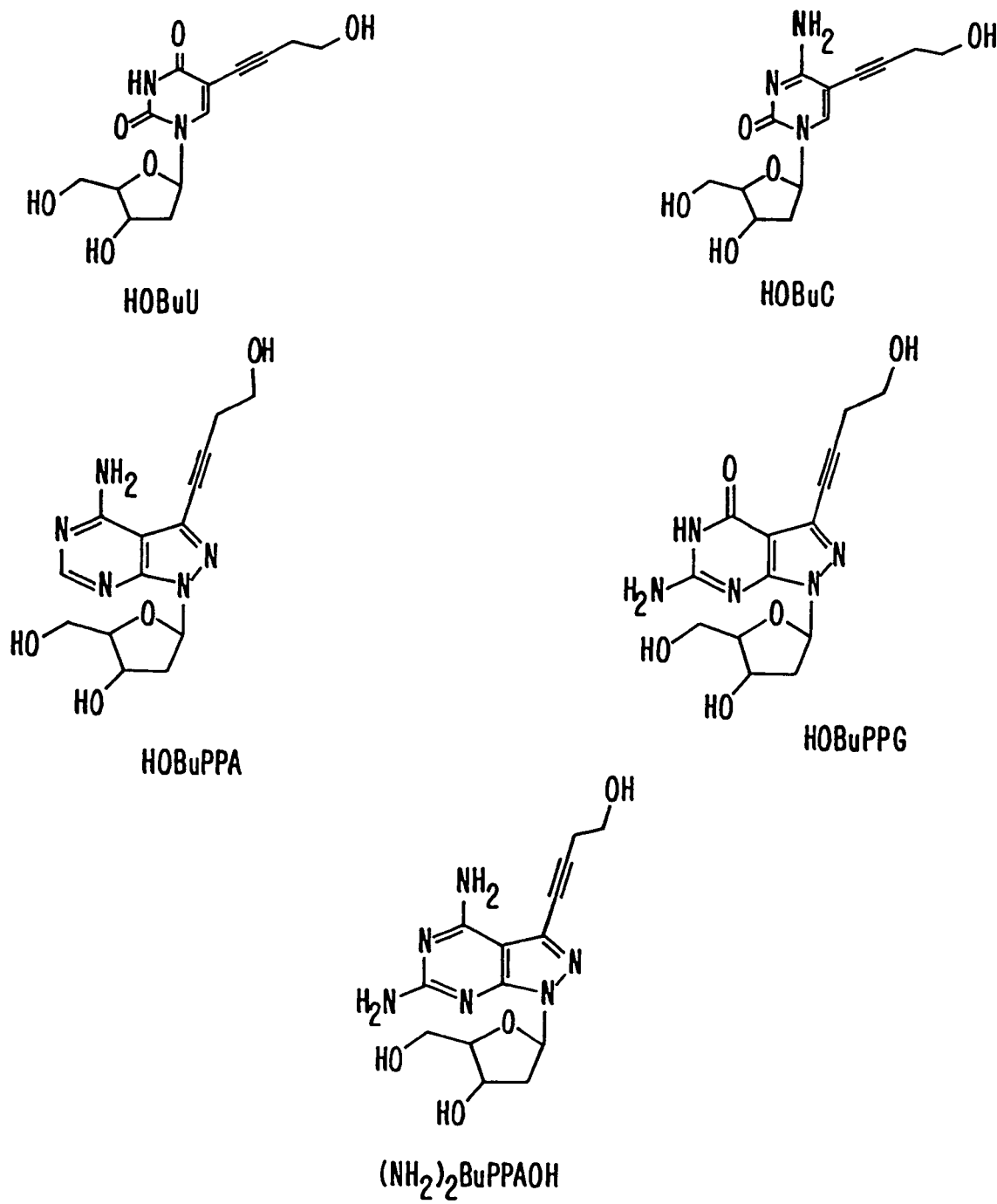

Abbreviations for a number of the modified bases described herein are provided as follows (structures of these bases are shown in FIGS. 1A and 1B): 6-amino-3-prop-1-ynyl-5-hydropyrazolo[3,4-d]pyrimidine-4-one, PPPG; 6-amino-3-(3-hydroxyprop-1-yny)1-5-hydropyrazolo[3,4-d]pyrimidine-4-one, HOPPPG; 6-amino-3-(3-aminoprop-1-ynyl)-5-hydropyrazolo[3,4-d]pyrimidine-4-one, $NH_2$PPPG; 4-amino-3-(prop-1-ynyl)pyrazolo[3,4-d]pyrimidine, PPPA; 4-amino-3-(3-hydroxyprop-1-ynyl)pyrazolo[3,4-d]pyrimidine, HOPPPA; 4-amino-3-(3-aminoprop-1-ynyl)pyrazolo[3,4-d]pyrimidine, $NH_2$PPPA; 3-prop-1-ynylpyrazolo[3,4-d]pyrimidine-4,6-diamino, $(NH_2)_2$PPPA; 2-(4,6-diaminopyrazolo[3,4-d]pyrimidin-3-yl)ethyn-1-ol, $(NH_2)_2$PPPAOH; 3-(2-aminoethynyl)pyrazolo[3,4-d]pyrimidine-4,6-diamine, $(NH_2)_2$PPPA$NH_2$; 5-prop-1-ynyl-1,3-dihydropyrimidine-2,4-dione, PU; 5-(3-hydroxyprop-1-ynyl)-1,3-dihydropyrimidine-2,4-dione, HOPU; 6-amino-5-prop-1-ynyl-3-dihydropyrimidine-2-one, PC; 6-amino-5-(3-hydroxyprop-1-yny)-1,3-dihydropyrimidine-2-one, HOPC; and 6-amino-5-(3-aminoprop-1-yny)-1,3-dihydropyrimidine-2-one, $NH_2$PC; 5-[4-amino-3-(3-methoxyprop-1-ynyl)pyrazol[3,4-d]pyrimidinyl]-2-(hydroxymethyl)oxolan-3-ol, $CH_3$OPPPA; 6-amino-1-[4-hydroxy-5-(hydroxymethyl)oxolan-2-yl]-3-(3-methoxyprop-1-ynyl)-5-hydropyrazolo[3,4-d]pyrimidine-4-one, $CH_3$OPPPG; 5-(4-hydroxybut-1-ynyl)-1,3-dihydropyrimidine-2,4-dione, HOBuU; 6-amino-5-(4-hydroxybut-1-ynyl)-3-hydropyrimidine-2-one, HOBuC; 4-(4-aminopyrazolo[3,4-d]pyrimidin-3-yl)but-3-yn-1-ol, HOBuPPA; 6-amino-3-(4-hydroxybut-1-ynyl)pyrazolo[3,4-d]pyrimidin-4-ol, HOBuPPG; 4-(4,6-diaminopyrazolo[3,4-d]pyrimidin-3-yl)but-3-yn-1-ol, $(NH_2)_2$BuPPAOH.

Unless otherwise stated, the following terms used in the specification and claims have the meanings given below:

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, $(C_1-C_8)$alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, aralkyloxy), when a prefix is not included to indicate the number of main chain carbon atoms in an alkyl portion, the radical or portion thereof will have eight or fewer main chain carbon atoms.

The term "alkylene" means a linear saturated divalent hydrocarbon radical or a branched saturated divalent hydrocarbon radical having the number of carbon atoms indicated in the prefix. For example, $(C_1-C_6)$alkylene is meant to include methylene, ethylene, propylene, 2-methylpropylene, pentylene, and the like.

The term "alkenyl" refers to a linear monovalent hydrocarbon radical or a branched monovalent hydrocarbon radical having the number of carbon atoms indicated in the prefix and containing at least one double bond. For example, $(C_2-C_6)$ alkenyl is meant to include, ethenyl, propenyl, and the like.

The term "alkynyl" refers to a linear monovalent hydrocarbon radical or a branched monovalent hydrocarbon radical containing at least one triple bond and having the number of carbon atoms indicated in the prefix. For example, $(C_2-C_6)$ alkynyl is meant to include ethynyl, propynyl, and the like.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "aryl" means a monovalent monocyclic or bicyclic aromatic hydrocarbon radical of 6 to 10 ring atoms which is unsubstituted or substituted independently with one to four substituents, preferably one, two, or three substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkylalkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl) or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the substituted forms thereof. Similarly, the term "heteroaryl" refers to those aryl groups wherein one or more heteroatoms or heteroatom functional groups have replaced a ring carbon, while retaining aromatic properties, e.g., pyridyl, quinolinyl, quinazolinyl, thienyl, and the like. For brevity, the term aryl, when used in combination with other radicals (e.g., aryloxy, arylalkyl) is meant to include both aryl groups and heteroaryl groups as described above.

The term "arylalkyl" refers to a radical —R$^a$R$^b$ where R$^a$ is an alkylene group (having the indicated number of carbon atoms, or if unspecified having six or fewer main chain carbon atoms) and R$^b$ is an aryl group as defined herein. Examples of arylalkyl groups include benzyl, phenylethyl, 3-(3-chlorophenyl)-2-methylpentyl, and the like.

Similarly the term "arylalkenyl" means a radical —R$^a$R$^b$ where R$^a$ is an alkenylene group and R$^b$ is an aryl group as defined herein, e.g., 3-phenyl-2-propenyl, and the like.

"Arylheteroalkyl" means a radical —R$^a$R$^b$ where R$^a$ is an heteroalkylene group (having the indicated number of carbon atoms) and R$^b$ is an aryl group as defined herein, e.g., 2-hydroxy-2-phenyl-ethyl, 2-hydroxy-1-hydroxymethyl-2-phenyl-ethyl, and the like.

The term "aryloxy", refers to a radical —OR where R is an aryl group, e.g., phenoxy, naphthyloxy and the like.

The prefix "halo" and the term "halogen" when used to describe a substituent, refer to —F, —Cl, —Br and —I.

The term "heteroalkyl" refers to an alkyl radical as defined herein with one, two or three substituents independently selected from cyano, —OR$^a$, —NR$^b$R$^c$, and —S(O)$_n$R$^d$ (where n is an integer from 0 to 2), with the understanding that the point of attachment of the heteroalkyl radical is through a carbon atom of the heteroalkyl radical. R$^a$ is hydrogen, alkyl, aryl, arylalkyl, alkoxycarbonyl, aryloxycarbonyl, carboxamido, or mono- or di-alkylcarbamoyl. $R^b$ is hydrogen, alkyl, aryl or arylalkyl. $R^c$ is hydrogen, alkyl, aryl, arylalkyl, alkoxycarbonyl, aryloxycarbonyl, carboxamido, mono- or di-alkylcarbamoyl or alkylsulfonyl. $R^d$ is hydrogen (provided that n is 0), alkyl, aryl, arylalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, $R^a$, $R^b$, $R^c$, and $R^d$ can be further substituted by $NH_2$, fluorine, alkylamino di-alkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —$OR^a$, —$NR^bR^c$, or —$S(O)_nR^d$ portions.

The term "heterocyclyl" refers to a saturated or unsaturated non-aromatic cyclic radical of 3 to 8 ring atoms in which one or two ring atoms are heteroatoms selected from O, NR (where R is independently hydrogen or alkyl) or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, halo, nitro, cyano, hydroxy, alkoxy, amino, mono-alkylamino, di-alkylamino, haloalkyl, haloalkoxy, —COR (where R is hydrogen, alkyl, cycloalkyl, cycloalkyl-alkyl, phenyl or phenylalkyl), —(CR'R")$_n$—COOR (n is an integer from 0 to 5, R' and R" are independently hydrogen or alkyl, and R is hydrogen, alkyl, cycloalkyl, cycloalkyl-alkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, phenyl or phenylalkyl). More specifically the term heterocyclyl includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof. The prefix indicating the number of carbon atoms (e.g., $C_3$-$C_{10}$) refers to the total number of carbon atoms in the portion of the heterocyclyl group exclusive of the number of heteroatoms.

The terms "heterocyclylalkyl," "heterocyclylalkenyl," "heterocyclylalkynyl" refer to radicals —$R^aR^b$ where $R^a$ is an alkylene, alkenylene or alkynylene group, respectively, and $R^b$ is a heterocyclyl group as defined herein, e.g., tetrahydropyran-2-ylmethyl, 4-methylpiperazin-1-ylethyl, 3-piperidinylmethyl, and the like.

The terms "heteroalkylene" means a linear saturated divalent hydrocarbon radical of one to six carbons or a branched saturated hydrocarbon radical of three to six carbon atoms with one, two or three substituents independently selected from —$OR^a$, —$NR^bR^c$, and —$S(O)_nR^d$ (where n is an integer from 0 to 2) where, $R^a$, Rb, Rc, and $R^d$ are as defined herein for a heteroalkyl radical. Examples include, 2-hydroxyethan-1,2-diyl, 2-hydroxypropan-1,3-diyl and the like.

Each of the above terms (e.g., "alkyl," "heteroalkyl," and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, heterocycloalkyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O) NR"R'", —NR"C(O)$_2$R', —NH—C(NH$_2$)=NH, —NR'C (NH$_2$)=NH, —NH—C(NH$_2$)=NR', —S(O)R', —S(O)$_2$R', —S(O)$_2$NR"R'", —CN and —NO$_2$ in a number ranging from zero to four, preferably, zero, one, two or three substituents. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the alkyl groups will have from 0-3 substituents, more preferably 0, 1, or 2 substituents, unless otherwise specified.

Similarly, substituents for the aryl groups are varied and are selected from: -halogen, —OR', —OC(O)R', —NR'R", —SR', —R', —CN, —NO$_2$, —CO$_2$R', —CONR'R", —C(O) R', —OC(O)NR'R", —NR"C(O)R', —NR"C(O)$_2$R', —NR'—C(O)NR"R'", —NH—C(NH$_2$)=NH, —NR'C (NH$_2$)=NH, —NH—C(NH$_2$)=NR', —S(O)R', —S(O)$_2$R', —S(O)$_2$NR"R'", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR' and —S(O)$_2$NR'— is selected from hydrogen or unsubstituted ($C_1$-$C_6$)alkyl.

Certain compounds or oligonucleotides of the present invention may exist in a salt form. Such salts include base addition salts such as sodium, potassium, calcium, ammonium, organic amino, or magnesium salt, or a similar salt. When the compounds or modified oligonucleotides of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention. The methods for the determination of stereochemistry and the separation of isomers are well-known in the art (see discussion in Chapter 4 of "Advanced Organic Chemistry", 4th edition J. March, John Wiley and Sons, New York, 1992).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not (e.g., $^2$H), are intended to be encompassed within the scope of the present invention.

"Protecting group" or "protected form thereof" refers to a grouping of atoms that when attached to a reactive group in a molecule masks, reduces or prevents that reactivity. Examples of protecting groups can be found in T. W. Greene and P. G. Futs, Protective Groups in Organic Chemistry, (Wiley, 2nd ed. 1991), Beaucage and Iyer, Tetrahedron 48:2223-2311 (1992), and Harrison and Harrison et al., Compendium of Synthetic Organic Methods, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

General

Oligonucleotides are short polymers of nucleotides, generally less than 200 nucleotides, preferably less than 150 nucleotides, more preferably less than 100 nucleotides, more preferably less than 50 nucleotides and most preferably less than 21 nucleotides in length. Polynucleotides are generally considered, in the art, to comprise longer polymers of nucleotides than do oligonucleotides, although there is an art-recognized overlap between the upper limit of oligonucleotide length and the lower limit of polynucleotide length. With respect to the present invention, "oligonucleotide" generally refers to a nucleic acid, usually comprising a detectable label, that is used as a probe or as a primer; while polynucleotide refers to a nucleic acid containing a target sequence. Consequently, for the purposes of the present invention, the terms "oligonucleotide" and "polynucleotide" shall not be considered limiting with respect to polymer length.

The present invention provides modified oligonucleotides having new and surprising properties of superior mismatch discrimination, compared to unmodified oligonucleotides. Modified oligonucleotides of the invention are used as probes, wherein their hybridization to a target sequence is detected, or as primers, wherein their hybridization to a target sequence is followed by polynucleotide synthesis initiated from the 3' terminus of the modified oligonucleotide, and the synthesized product (i.e., the extension product) is detected.

A target sequence refers to a nucleotide sequence which comprises a site of hybridization for a probe or a primer. Target sequences can be found in any nucleic acid including, but not limited to, genomic DNA, cDNA, RNA and any amplified product thereof, and can comprise a wild-type gene sequence, a mutant gene sequence, a non-coding sequence, a regulatory sequence, etc. A target sequence will generally be less than 100 nucleotides, preferably less than 50 nucleotides, and most preferably, less than 21 nucleotides in length.

DESCRIPTION OF THE EMBODIMENTS

The present invention provides a number of modified oligonucleotides which can generally be divided into three groups.

The first group of modified oligonucleotides are those having at least two modified bases replacing the naturally-occurring bases. Here, the modified bases will be unsubstituted or 3-substituted pyrazolo[3,4-d]pyrimidines. In some embodiments, however, the modified bases will be selected such that at least one of the bases is a 5-substituted pyrimidine and at least one of the bases is an unsubstituted or a 3-substituted pyrazolo[3,4-d]pyrimidine. Preferably, this group of modified oligonucleotides will have additional attached groups (e.g., minor groove binders, reporter groups, quenchers, etc.) which assist during assays to detect target sequences.

The second group of modified oligonucleotides are those having at least one modified base, but also having an attached minor groove binder, reporter group, quencher, or the like.

The third group of modified oligonucleotides are those that comprise one or more of the novel modified bases described below. As in the first group, this group of modified oligonucleotides will preferably have attached groups selected from, for example, minor groove binders, reporter groups or quenchers.

Modified Oligonucleotides

In one aspect, the present invention provides modified oligonucleotides comprising at least two bases selected from the group consisting of unsubstituted and 3-substituted pyrazolo [3,4-d]pyrimidine bases.

The pyrazolo[3,4-d]pyrimidine bases are those bases in which a pyrazole ring is fused to a pyrimidine ring in the following specific orientation:

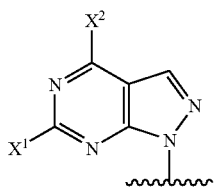

Ia in which the wavy line indicates the point of attachment between the base and either an attached oligomer-forming sugar or an amino acid involved in peptide nucleic acid formation. Additionally, the groups $X^1$ and $X^2$ are independently H, OH or $NH_2$ such that the pyrazolo[3,4-d]pyrimidine bases approximate the construction of the natural purine bases, guanosine, adenine and inosine, as well as related derivatives of those bases. In this group of embodiments, an "unsubstituted pyrazolo[3,4-d]pyrimidine base" refers to those bases of the general formula Ia, while the term "3-substituted pyrazolo[3,4-d]pyrimidine base" refers to those bases having the formula Ib, in which $R^1$ is defined as described below.

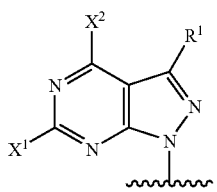

Ib

In formula Ib, the symbols $X^1$ and $X^2$ independently represent H, OH, $NH_2$ or a protected form thereof. The symbol $R^1$ represents a member selected from $(C_1-C_{12})$heteroalkyl, $(C_2-C_{12})$heteroalkenyl, $(C_2-C_{12})$heteroalkynyl, $-O-(C_1-C_{12})$alkyl, $-O-(C_2-C_{12})$alkenyl, $-O-(C_2-C_{12})$alkynyl, $-S-(C_1-C_{12})$alkyl, $-S-(C_2-C_{12})$alkenyl, $-S-(C_2-C_{12})$alkynyl, heterocyclyl$(C_1-C_{12})$alkyl, heterocyclyl$(C_2-C_{12})$alkenyl, heterocyclyl$(C_2-C_{12})$alkynyl, aryl$(C_1-C_{12})$alkyl, aryl$(C_2-C_{12})$alkenyl, aryl$(C_2-C_{12})$alkynyl, aryl, heterocyclyl, halogen, $-CN$, $-CONH_2$ and protected forms thereof. Preferred heteroalkyl, heteroalkenyl and heteroalkynyl groups are those that terminate (distal to the pyrazolo[3,4-d]pyrimidine ring system) in a heteroatom group (e.g., OH, $NH_2$, SH and the like). For example, preferred heteroalkyl, heteroalkenyl and heteroalkynyl groups include 3-amino-1-propyl, 4-hydroxy-1-butyl, 3-amino-1-propyn-1-yl, 3-hydroxy-1-propyn-1-yl, 4-hydroxy-3-hydroxymethyl-1-butyn-1-yl, 4-hydroxy-1-butyn-1-yl, and their higher homologs. Other preferred $R^1$ groups include those which terminate in an aryl or heterocyclic group (e.g., heterocyclyl$(C_1-C_{12})$alkyl, heterocyclyl$(C_2-C_{12})$alkenyl, heterocyclyl$(C_2-C_{12})$alkynyl, aryl $(C_1-C_{12})$alkyl, aryl$(C_2-C_{12})$alkenyl and aryl$(C_2-C_{12})$alkynyl). Preferred aryl and heterocyclic groups are either substituted or unsubstituted phenyl, thienyl, thiazolyl, imidazolyl, furanyl, oxazolyl, pyridinyl, pyrrolyl, indolyl, benzimidazolyl, benzthiazolyl and benzoxazolyl.

In particularly preferred embodiments, the pyrazolo[3,4-d]pyrimidine base is selected from:

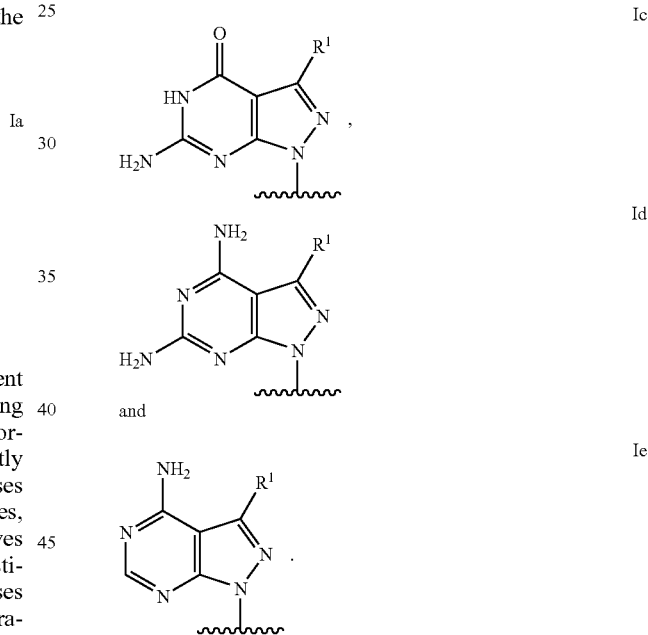

Still more preferably, the modified bases are selected from Ic, Id or Ie wherein each $R^1$ is a propynyl, hydroxypropynyl, aminopropynyl, aminobutynyl, hydroxybutynyl, or a substituted or unsubstituted phenyl, thienyl, thiazolyl, imidazolyl, furanyl, oxazolyl, pyridinyl, pyrrolyl, indolyl, benzimidazolyl, benzthiazolyl or benzoxazolyl group attached directly to the pyrazolo[3,4-d]pyrimidine ring system or attached to the ring system via a one to four carbon linking group which can be saturated (e.g., ethylene, propylene, butylene) or unsaturated (e.g., acetylenyl, propynylene, butynylene, propenylene, butenylene).

The modified oligonucleotides of the present invention have a backbone such as, for example, that found with the naturally-occurring oligonucleotides or peptide-nucleic acids (e.g., heterocyclic bases attached to oligomer-forming sugars or peptide-nucleic acid-forming amino acids). Alternative oligomeric backbones are known to those of skill in the art (referred to below as "modified" backbones or comprising backbone modifications). For the purpose of this invention a modified oligonucleotide is any oligomeric polymer, including the natural phosphate backbone and non-natural backbones, that contains natural and/or modified bases and retains the ability to hybridize specifically to a complementary nucleic acid to form a stable duplex.

In preferred embodiments, the modified oligonucleotides of the invention have a backbone of sugar or glycosidic moieties, preferably 2-deoxyribofuranosides wherein all internucleotide linkages are the naturally occurring phosphodiester linkages. In alternative embodiments however, the 2-deoxy-β-D-ribofuranose groups are replaced with other sugars, for example, β-D-ribofuranose. In addition, β-D-ribofuranose may be present wherein the 2-OH of the ribose moiety is alkylated with a $C_{1-6}$ alkyl group (2-(O—$C_{1-6}$ alkyl) ribose) or with a $C_{2-6}$ alkenyl group (2-(O—$C_{2-6}$ alkenyl) ribose), or is replaced by a fluoro group (2-fluororibose). Related oligomer-forming sugars useful in the present invention are those that are "locked", i.e., contain a methylene bridge between C-4' and an oxygen atom at C-2'. Other sugar moieties compatible with hybridization of the oligonucleotide can also be used, and are known to those of skill in the art, including, but not limited to, α-D-arabinofuranosides, α-2'-deoxyribofuranosides or 2',3'-dideoxy-3'-aminoribofuranosides. Oligonucleotides containing α-D-arabinofuranosides can be prepared as described in U.S. Pat. No. 5,177,196. Oligonucleotides containing 2',3'-dideoxy-3'-aminoribofuranosides are described in Chen et al. ((1995) *Nucleic Acids Res.* 23:2661-2668). Synthetic procedures for locked nucleic acids (Singh et al, *Chem. Comm.*, 455-456 (1998); Wengel J., *Acc. Chem. Res.*, 32:301-310 (1998)) and oligonucleotides containing 2'-halogen-2'-deoxyribofuranosides (Palissa et al., *Z. Chem.* 27:216 (1987)) have been described. The phosphate backbone of the modified oligonucleotides described herein can also be modified so that the oligonucleotides contain phosphorothioate linkages and/or methylphosphonates and/or phosphoroamidates (Chen et al., *Nucl. Acids Res.*, 23:2662-2668 (1995)). Combinations of oligonucleotide linkages are also within the scope of the present invention. Still other backbone modifications are known to those of skill in the art.

In another group of embodiments, the modified bases described herein are incorporated into PNA and DNA/PNA chimeras to balance $T_m$s and provide modified oligonucleotides having improved mismatch discrimination. Various modified forms of DNA and DNA analogues have been used in attempts to overcome some of the disadvantages of the use of DNA molecules as probes and primers. Among these are peptide nucleic acids (PNAs, also known as polyamide nucleic acids). Nielsen et al. (1991) *Science* 254:1497-1500. PNAs contain heterocyclic base units, as found in DNA and RNA, that are linked by a polyamide backbone, instead of the sugar-phosphate backbone characteristic of DNA and RNA. PNAs are capable of hybridization to complementary DNA and RNA target sequences and, in fact, hybridize more strongly than a corresponding nucleic acid probe. The synthesis of PNA oligomers and reactive monomers used in the synthesis of PNA oligomers have been described in U.S. Pat. Nos. 5,539,082; 5,714,331; 5,773,571; 5,736,336 and 5,766,855. Alternate approaches to PNA and DNA/PNA chimera synthesis and monomers for PNA synthesis have been summarized. Uhlmann et al. (1998) *Angew. Chem. Int. Ed.* 37:2796-2823. Accordingly, the use of any combination of normal bases, unsubstituted pyrazolo[3,4-d]pyrimidine bases (e.g., PPG and PPA), 3-substituted pyrazolo[3,4-d]pyrimidines, modified purine, modified pyrimidine, 5-substituted pyrimidines, universal bases or a minor groove binder to balance the $T_m$ of a PNA or DNA/PNA chimera is in the scope of this invention. A variety of universal bases are known in the art. Other universal bases have recently been described and are also useful in the present invention (see, Seela, et al., XIV International Round Table: Nucleosides, Nucleotides and Their Biological Applications, Sep. 10-14, 2000, San Francisco Calif., pp. 40). The synthetic methods necessary for the synthesis of modified base monomeric units required for PNA and PNA/DNA chimeras synthesis are available in the art, see methods in this application and Uhlmann et al. *Angew. Chem. Int. Ed.* 37:2796-2823 (1998).

Similarly, the present invention demonstrates a combination of normal bases, unsubstituted pyrazolo[3,4-d]pyrimidine bases (e.g., PPG and PPA), 3-substituted pyrazolo[3,4-d]pyrimidines, modified purine, modified pyrimidine, 5-substituted pyrimidines, universal bases or a minor groove binder can be used to balance the $T_m$ of any oligonucleotide polymer or oligopolymer/DNA chimera.

For the uses described herein, the modified oligonucleotides will preferably have from 4 to 70 bases, more preferably from 4 to 25 bases. In some embodiments, the modified oligonucleotides will have 15 or fewer, or more preferably 10 or fewer bases. Additionally, the modified oligonucleotides will, in some embodiments, have 3, 4, 5, 6, 7, 8, or 9 or more modified bases (either unsubstituted or 3-substituted pyrazolo[3,4-d]pyrimidines). For each of the embodiments wherein multiple 3-substituted pyrazolo[3,4-d]pyrimidine bases are present, the modified bases can either be the same or different from each other.

In addition to the modified base components, the modified oligonucleotides of the present invention will in some embodiments comprise additional pendant groups such as, for example, intercalators, lipophilic groups, minor groove binders, reporter groups, chelating agents, quenchers and cross-linking agents attached to one or more of the internally located nucleotide bases, to the 3', to the 5' end, to both ends, or can have such pendant groups attached both internally and at one or both ends. Methods suitable for attaching intercalator, lipophilic groups, minor grove binders, reporter groups, chelating agents, quenchers and cross-linking agents to oligonucleotides have been described in, for example, U.S. Pat. Nos. 5,512,667 and 5,419,966, PCT publication WO 96/32496 and U.S. application Ser. No. 09/457,616. The oligonucleotides of the invention can also have a relatively low molecular weight "tail moiety" attached either at the 3' or 5' end, or at both ends. By way of example a tail molecule can be a phosphate, a phosphate ester, an alkyl group, an aminoalkyl group, or a lipophilic group. The tail moiety can also link the intercalators, lipophilic groups, minor groove binders, reporter groups, chelating agents and cross-linking functionalities to the oligonucleotides of the invention. The nature of tail moieties and methods for obtaining oligonucleotides with various tail moieties are also described in the above-referenced U.S. Pat. Nos. 5,512,667 and 5,419,966.

Minor Groove Binders

In one group of embodiments, the modified oligonucleotide will also have a covalently attached minor groove binder (MGB). A variety of suitable minor groove binders have been described in the literature. See, for example, Kutyavin, et al. U.S. Pat. No. 5,801,155; Wemmer, D. E., and Dervan P. B., *Current Opinion in Structural Biology*, 7:355-361 (1997); Walker, W. L., Kopka, J. L. and Goodsell, D. S., *Biopolymers*, 44:323-334 (1997); Zimmer, C & Wahnert, U. *Prog. Biophys. Molec. Bio.* 47:31-112 (1986) and Reddy, B. S. P., Dondhi, S. M., and Lown, J. W., *Pharmacol. Therap.*, 84:1-111 (1999).

Suitable methods for attaching MGBs (as well as reporter groups such as fluorophores and quenchers described below) through linkers to oligonucleotides are described in, for example, U.S. Pat. Nos. 5,512,677; 5,419,966; 5,696,251; 5,585,481; 5,942,610 and 5,736,626.

The MGB can be attached at either or both ends of the oligonucleotide. In addition or alternatively, one or more MGBs can be attached in the interior of the oligonucleotide, depending on the length of the oligonucleotide. In general, conjugation of a MGB to either end of an oligonucleotide would provide the greatest degree of hybrid stability, since melting of an oligonucleotide duplex begins at the termini. Nonetheless, if both ends of a duplex formed by an oligonucleotide are relatively stable, for example, due to a high G+C content, attachment of a MGB in the interior of an oligonucleotide (for instance, near an A+T-rich sequence) could also enhance stability. The intended use of the MGB-oligonucleotide conjugate may also place limitations on the location of the conjugated MGB. For example, if an oligonucleotide is designed to be used as a primer, the 3'-hydroxy group must be free and capable of being elongated by a polymerizing enzyme. Alternatively, an assay that requires an oligonucleotide possessing a labeled 5'-end would require internal or 3'-end attachment of a MGB.

The location of a MGB within a MGB-modified oligonucleotide conjugate can also affect the discriminatory properties of such a conjugate. An unpaired region within a duplex will result in changes in the shape of the minor groove in the vicinity of the mispaired base(s). Since MGBs fit best within the minor groove of a perfectly-matched DNA duplex, mismatches resulting in shape changes in the minor groove would reduce binding strength of a MGB to a region containing a mismatch. Hence, the ability of a MGB to stabilize such a hybrid would be decreased, thereby increasing the ability of a MGB-oligonucleotide conjugate to discriminate a mismatch from a perfectly-matched duplex. On the other hand, if a mismatch lies outside of the region complementary to a MGB-oligonucleotide conjugate, discriminatory ability for unconjugated and MGB-conjugated oligonucleotides of equal length is expected to be approximately the same. Since the ability of an oligonucleotide probe to discriminate single base pair mismatches depends on its length, shorter oligonucleotides are more effective in discriminating mismatches. The primary advantage of the use of MGB-oligonucleotides conjugates in this context lies in the fact that much shorter oligonucleotides compared to those used in the prior art (i.e., 20-mers or shorter), having greater discriminatory powers, can be used, due to the pronounced stabilizing effect of MGB conjugation.

Preferred minor groove binders are those selected from the formulae:

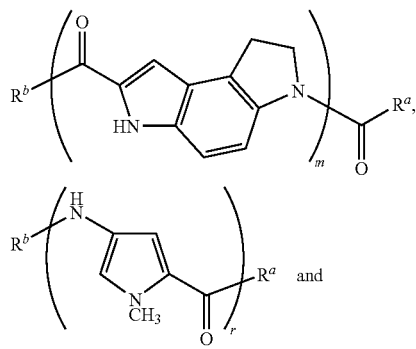

-continued

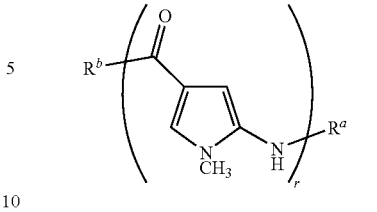

the subscript m is an integer of from 2 to 5; the subscript r is an integer of from 2 to 10; and each $R^a$ and $R^b$ is independently a linking group to the modified oligonucleotide, H, —$OR^c$, —$NR^cR^d$, —$COOR^c$ or —$CONR^cR^d$, wherein each $R^c$ and $R^d$ is selected from H, ($C_1$-$C_{12}$)heteroalkyl, ($C_2$-$C_{12}$) heteroalkenyl, ($C_2$-$C_{12}$)heteroalkynyl, ($C_1$-$C_{12}$)alkyl, ($C_2$-$C_{12}$)alkenyl, ($C_2$-$C_{12}$)alkynyl, aryl($C_1$-$C_{12}$)alkyl and aryl.

Particularly preferred minor groove binders include the trimer of 3-carbamoyl-1,2-dihydro-(3H)-pyrrolo[3,2-e]indole-7-carboxylate ($CDPI_3$), the pentamer of N-methylpyrrole-4-carbox-2-amide ($MPC_5$) and other minor groove binders that exhibit increased mismatch discrimination. Additional MGB moieties that will find use in the practice of the present invention are disclosed in co-owned U.S. Pat. No. 5,801,155. In certain embodiments, the MGBs can have attached water solubility-enhancing groups (e.g., sugars or amino acids).

Reporter Groups

In another group of embodiments, the modified oligonucleotide will further comprise at least one covalently attached reporter group. The reporter groups can be attached using methods and linking groups described above for the MGBs. Suitable reporter groups for the present modified oligonucleotides include beads, nanoparticles (Taton, T. A. et al, *Science* 289:1757-1760 (2000)), chemiluminescers, isotopes, enzymes and fluorophores. Preferably, the reporter group is a fluorophore (see, Haugland, R. P., HANDBOOK OF FLUORESCENT PROBES AND RESEARCH CHEMICALS, Sixth Edition, Molecular Probes, Eugene, Oreg., 1996). Suitable fluorophores include the resorufin dyes, coumarin dyes, rhodamine dyes, cyanine dyes, BODIPY dyes and pyrenes.

Quenchers

Recently developed detection methods employ the process of fluorescence resonance energy transfer (FRET) for the detection of probe hybridization rather than direct detection of fluorescence intensity. In this type of assay, FRET occurs between a donor fluorophore (reporter) and an acceptor molecule (quencher) when the absorption spectrum of the quencher molecule overlaps with the emission spectrum of the donor fluorophore and the two molecules are in close proximity. The excited-state energy of the donor fluorophore is transferred to the neighboring acceptor by a resonance dipole-induced dipole interaction, which results in quenching of the donor fluorescence. If the acceptor molecule is a fluorophore, its fluorescence may sometimes be increased. The efficiency of the energy transfer between the donor and acceptor molecules is highly dependent on distance between the molecules. Equations describing this relationship are known. The Forster distance ($R_o$) is described as the distance between the donor and acceptor molecules where the energy transfer is 50% efficient. Other mechanisms of fluorescence quenching are also known, such as, collisional and charge transfer quenching. There is extensive guidance in the art for selecting quencher and fluor pairs and their attachment to oligonucleotides (Haugland, R. P., HANDBOOK OF FLUORESCENT PROBES AND RESEARCH CHEMICALS, Sixth Edition, Molecular Probes, Eugene, Oreg., 1996; U.S. Pat. Nos. 3,996,345 and 4,351,760 and the like).

Preferred quenchers are described in co-owned U.S. Ser. No. 09/457,616 (filed Dec. 8, 1999).

Fluorophores and Quenchers

In certain embodiments of the present invention, oligonucleotides comprising fluorescent labels (fluorophores) and/or fluorescence quenching agents are used. In a preferred embodiment, an oligonucleotide contains both a fluorophore and a quenching agent. Fluorescent labels include, but are not limited to, fluoresceins, rhodamines, cyanines, phycoerythrins, and other fluorophores as described herein. Still other suitable fluorophores are known to those of skill in the art. As noted above, quenching agents or quenchers can absorb energy emitted by a fluorophore so as to reduce the amount of fluorescence emitted (i.e., quench the emission of the fluorescent label). Different fluorophores are quenched by different quenching agents. In general, the spectral properties of a particular fluorophore/quenching agent pair are such that one or more absorption wavelengths of the quencher overlaps one or more of the emission wavelengths of the fluorophore. A preferred fluorophore/quencher pair can be selected by one of skill in the art by comparison of emission and excitation wavelengths according to the properties set forth above.

For use in amplification assays conducted at elevated temperatures, such as a polymerase chain reaction, or other procedures utilizing thermostable enzymes, the label is preferably one that is stable at elevated temperatures. For assays involving polymerization, the label is one that does not interfere with the activity of the polymerizing enzyme. Additionally, the label will be present at the 5' and/or 3' end of the oligonucleotide, and/or can also be present internally in a non-interfering position. Accordingly, the label can be attached to any of the bases, sugars or phosphate moieties of the oligonucleotide, or to any linking group that is itself attached to one of these moieties.

While the invention has been described in terms of the various bases and other optional components, the overall structure of the modified oligonucleotides can also be expressed in a formula to indicate a desired construction.

Thus, in one group of embodiments, the modified oligonucleotides have the formula:

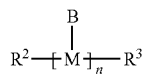

wherein $R^2$ and $R^3$ represent the termini of the modified oligonucleotide; the subscript n is an integer of from 4 to 70, more preferably 4 to 25 and still more preferably 4 to 10; each B is a member independently selected from adenine, thymine, cytosine, guanine, uracil, an unsubstituted pyrazolo[3,4-d]pyrimidine and a 3-substituted pyrazolo[3,4-d]pyrimidine; and each M is selected from an oligomer-forming sugar and a peptide-nucleic acid-forming amino acid, with the proviso that at least two of the Bs are selected from unsubstituted pyrazolo[3,4-d]pyrimidines and a 3-substituted pyrazolo[3,4-d]pyrimidines. In certain specific embodiments, $R^2$ and $R^3$ represent the 5'- and 3'-ends of a modified oligonucleotides wherein M is an oligomer-forming sugar (e.g., 2-deoxy-β-D-ribofuranose, β-D-ribofuranose, α-D-arabinofuranosides, α-2'-deoxyribofuranosides, 2',3'-dideoxy-3'-aminoribofuranosides, and locked sugars). For those embodiments in which the modified oligonucleotides have attached minor groove binders, reporter groups, etc., each of the $R^2$ and $R^3$ groups are meant to include functional groups suitable for attachment of linking groups and the additional functional component (MGB, fluorophore, quencher, and the like). Such functional groups include, for example, hydroxy groups, amino groups, carboxylic acid or ester groups, phosphoric, phosphonic, or phosphinic acid or ester groups, sulfonic acid and ester groups, and the like. In other embodiments, MGBs, reporter groups and the like are attached to any of the interior base/backbone groups using conventional methodology.

In a related aspect, the present invention provides modified oligonucleotides comprising at least one 5-substituted pyrimidine base and at least one unsubstituted or 3-substituted pyrazolo[3,4-d]pyrimidine base. The unsubstituted or 3-substituted pyrazolo[3,4-d]pyrimidine bases useful in this aspect of the invention are essentially those that have been described above (see formulae Ia and Ib). A variety of 5-substituted pyrimidine bases are useful including those described in U.S. Pat. Nos. 5,645,985 and 5,484,908.

In preferred embodiments, the 5-substituted pyrimidine base has the formula:

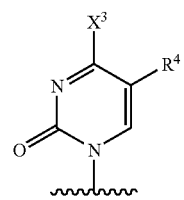

IIa and the unsubstituted or 3-substituted pyrazolo[3,4-d]pyrimidine base has the formula:

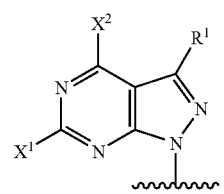

Ib wherein each of the $X^1$, $X^2$ and $X^3$ groups is independently selected from H, OH, $NH_2$ and a protected amino group; and each of the $R^1$ and $R^4$ groups is independently selected from $(C_1-C_{12})$heteroalkyl, $(C_2-C_{12})$heteroalkenyl, $(C_2-C_{12})$heteroalkynyl, —O—$(C_1-C_{12})$alkyl, —O—$(C_2-C_{12})$alkenyl, —O—$(C_2-C_{12})$alkynyl, —S—$(C_1-C_{12})$alkyl, —S—$(C_2-C_{12})$alkenyl, —S—$(C_2-C_{12})$alkynyl, heterocyclyl$(C_1-C_{12})$alkyl, heterocyclyl$(C_2-C_{12})$alkenyl, heterocyclyl$(C_2-C_{12})$alkynyl, aryl$(C_1-C_{12})$alkyl, aryl$(C_2-C_{12})$alkenyl, aryl$(C_2-C_{12})$alkynyl, aryl, heterocyclyl, halogen, —CN, —$CONH_2$ and protected forms thereof, with the additional feature that $R^1$ can also be H.

In particularly preferred embodiments, the 5-substituted pyrimidine base is selected from:

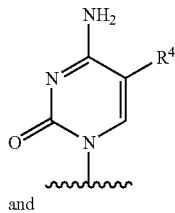

IIb and

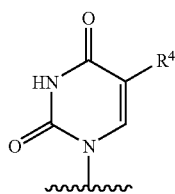

IIc wherein R⁴ is preferably selected from propynyl, hydroxypropynyl, aminopropynyl, hydroxybutynyl or a substituted or unsubstituted phenyl, thienyl, thiazolyl, imidazolyl, furanyl, oxazolyl, pyridinyl, pyrrolyl, indolyl, benzimidazolyl, benzthiazolyl or benzoxazolyl group attached directly to the pyrimidine ring or attached to the ring via a one to four carbon linking group which can be saturated (e.g., ethylene, propylene, butylene) or unsaturated (e.g., acetylenyl, propynylene, butynylene, propenylene, butenylene).

In other preferred embodiments, the pyrazolo[3,4-d]pyrimidine base is selected from the preferred bases provided above (Ic, Id and Ie). Additionally, suitable bases are also depicted in FIG. 1.

As with the earlier aspect of the invention wherein the modified oligonucleotides comprise at least two unsubstituted or 3-substituted pyrazolo[3,4-d]pyrimidines, this aspect of the invention can similarly comprise additional groups such as MGBs and reporter groups (e.g., fluorophores, quenchers and the like) as well as linking groups suitable for the attachment of these additional components.

Also preferred are those embodiments in which the modified oligonucleotide is represented by the formula:

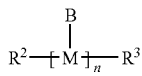

wherein R² represents a first end of the modified oligonucleotide; R³ represents a second end of the modified oligonucleotide; the subscript n is an integer of from 4 to 70; each B is independently selected from adenine, thymine, cytosine, guanine, uracil, a 5-substituted pyrimidine, an unsubstituted pyrazolo[3,4-d]pyrimidine and a 3-substituted pyrazolo[3,4-d]pyrimidine (with the proviso that at least one base is a 5-substituted pyrimidine and at least one base is a pyrazolo [3,4-d]pyrimidine); and each M is an oligomer-forming sugar or a peptide-nucleic acid-forming amino acid.

In yet another aspect of the invention, modified oligonucleotides are provided which comprise an attached minor groove binder and in which as few as one of the bases is replaced with a modified base. Surprisingly, the combination of MGBs and a single modified base (or optionally multiple modified bases) leads to modified oligonucleotides having particularly useful properties for mismatch discrimination as well as primer extensions and other utilities described below. This group of modified oligonucleotides preferably comprise from 4 to 70 bases, and an attached minor groove binder, wherein at least one of the bases is replaced by a modified base selected from the group consisting of 5-substituted pyrimidines and unsubstituted or 3-substituted pyrazolo[3,4-d]pyrimidines.

In this aspect of the invention, the minor groove binders, 5-substituted pyrimidines and unsubstituted or 3-substituted pyrazolo[3,4-d]pyrimidines can be essentially any of those components described above.

In one group of embodiments, the modified oligonucleotide has at least one 5-substituted pyrimidine, preferably having the formula:

IIa wherein $X^3$ is selected from H, $NH_2$, OH and SH; and $R^4$ is selected from $(C_1$-$C_{12})$heteroalkyl, $(C_2$-$C_{12})$heteroalkenyl, $(C_2$-$C_{12})$heteroalkynyl, —O—$(C_1$-$C_{12})$alkyl, —O—$(C_2$-$C_{12})$alkenyl, —O—$(C_2$-$C_{12})$alkynyl, —S—$(C_1$-$C_{12})$alkyl, —S—$(C_2$-$C_{12})$alkenyl, —S—$(C_2$-$C_{12})$alkynyl, heterocyclyl $(C_1$-$C_{12})$alkyl, heterocyclyl$(C_2$-$C_{12})$alkenyl, heterocyclyl $(C_2$-$C_{12})$alkynyl, aryl$(C_1$-$C_{12})$alkyl, aryl$(C_2$-$C_{12})$alkenyl, aryl$(C_2$-$C_{12})$alkynyl, aryl, heterocyclyl, halogen, —CN, —$CONH_2$ and protected forms thereof. In this group of embodiments, preferred aryl and heterocyclyl group (including those components of other groups, e.g., arylalkyl) are selected from substituted and unsubstituted versions of phenyl, tolyl, pyridyl, thiazolyl, imidazolyl, furanyl, oxazolyl, thienyl, pyrrolyl, benzimidazolyl, benzoxazolyl, benzthiazolyl, indolyl, triazinyl, pyrimidinyl and naphthyl. Suitable substituents for these aryl and heterocyclyl groups are those provided in the general definitions above.

More preferably, the modified oligonucleotides comprise at least one 5-substituted pyrimidine based group of Formula IId and IIe, where the R⁴ substituent group is selected from a substituted or unsubstituted alkyl group or alkynyl group. Preferably, R⁴ is a hydroxypropynyl, hydroxybutynyl, aminopropynyl, aminobutynyl or propynyl group, as well as the higher homologs (e.g., $C_5$-$C_8$) of these alkynyl groups. Alternatively, the R⁴ substituent can be a 3-(hydroxymethyl)-4-hydroxy-1-butynyl group (described in more detail below).

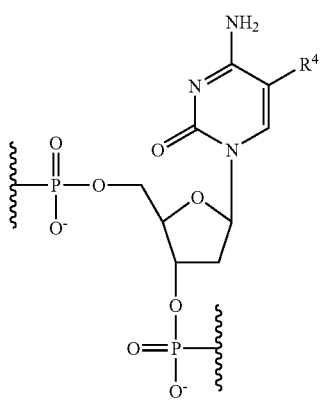

IId

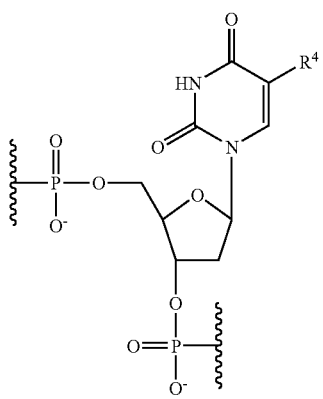

IIe

In another group of preferred embodiments, the modified oligonucleotide has at least one modified base having the formula:

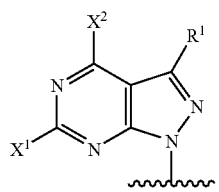

Ib wherein each of the $X^1$ and $X^2$ groups is independently selected from H, OH, $NH_2$ and a protected amino group; and $R^1$ is selected from H, $(C_1-C_{12})$heteroalkyl, $(C_2-C_{12})$heteroalkenyl, $(C_2-C_{12})$heteroalkynyl, —O—$(C_1-C_{12})$alkyl, —O—$(C_2-C_{12})$alkenyl, —O—$(C_2-C_{12})$alkynyl, —S—$(C_1-C_{12})$alkyl, —S—$(C_2-C_{12})$alkenyl, —S—$(C_2-C_{12})$alkynyl, heterocyclyl$(C_1-C_{12})$alkyl, heterocyclyl$(C_2-C_{12})$alkenyl, heterocyclyl$(C_2-C_{12})$alkynyl, aryl$(C_1-C_{12})$alkyl, aryl$(C_2-C_{12})$alkenyl, aryl$(C_2-C_{12})$alkynyl, aryl, heterocyclyl, halogen, —CN, —$CONH_2$ and protected forms thereof. In this group of embodiments, preferred aryl and heterocyclyl group (including those components of other groups, e.g., arylalkyl, heterocyclylalkyl) are selected from substituted and unsubstituted versions of phenyl, tolyl, pyridyl, thiazolyl, imidazolyl, furanyl, oxazolyl, thienyl, pyrrolyl, benzimidazolyl, benzoxazolyl, benzthiazolyl, indolyl, triazinyl, pyrimidinyl and naphthyl. Suitable substituents for these aryl and heterocyclyl groups are those provided in the general definitions above.

In particularly preferred embodiments, the modified oligonucleotides comprise at least one monomer of formula If,

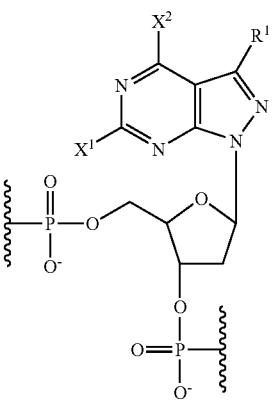

If wherein $X^1$ and $X^2$ are independently H, OH or $NH_2$; and $R^1$ is most preferably 3-hydroxypropyn-1-yl, propynyl, 3-aminopropyn-1-yl, 4-hydroxy-1-butynyl, 3-(hydroxymethyl)-4-hydroxy-1-butynyl, halogen or 3,3,3-trifluoropropyn-1-yl. Syntheses of some of these monomers have been reported (Balow et al., *Nuc. Acid Res.*, 26:3350-3357 (1998); Seela et al., *J. Chem. Soc. Perkin Trans., I*, 479-488 (1999); Ramzaeva et al., *Helv. Chim. Acta*, 80:1809-1822 (1997)).

Preparation of Modified Bases and Oligonucleotides

Reaction Schemes 1-10 provide illustrative methods for preparing a number of modified bases (unsubstituted and 3-substituted pyrazolo[3,4-d]pyrimidines and 5-substituted pyrimidines) that are useful in the present invention. The schemes illustrate the preparation of phosphoramidite derivatives of the modified bases which can be used in, for example, automatic synthesizers for preparing the modified oligonucleotides of the invention.

Reaction Scheme 1 illustrates the preparation of 5-(prop-2-ynyl-4-methylbenzoate)-5'-O-(4,4'-dimethoxytriphenylmethyl)-2'-deoxyuridine 3'-[(2-cyanoethyl)N,N-diisopropylphosphoramidite] (3) starting from 5-iodo-2'-deoxyuridine. The starting materials was treated with prop-2-ynyl 4-methylbenzoate in the presence of Pd(PPh₃)₄—CuI to yield the methylbenzoate derivative (1) which was then converted to the 5'-blocked DMTr derivative (2) and then to the phosphoramidite (3).

Reaction Scheme 1

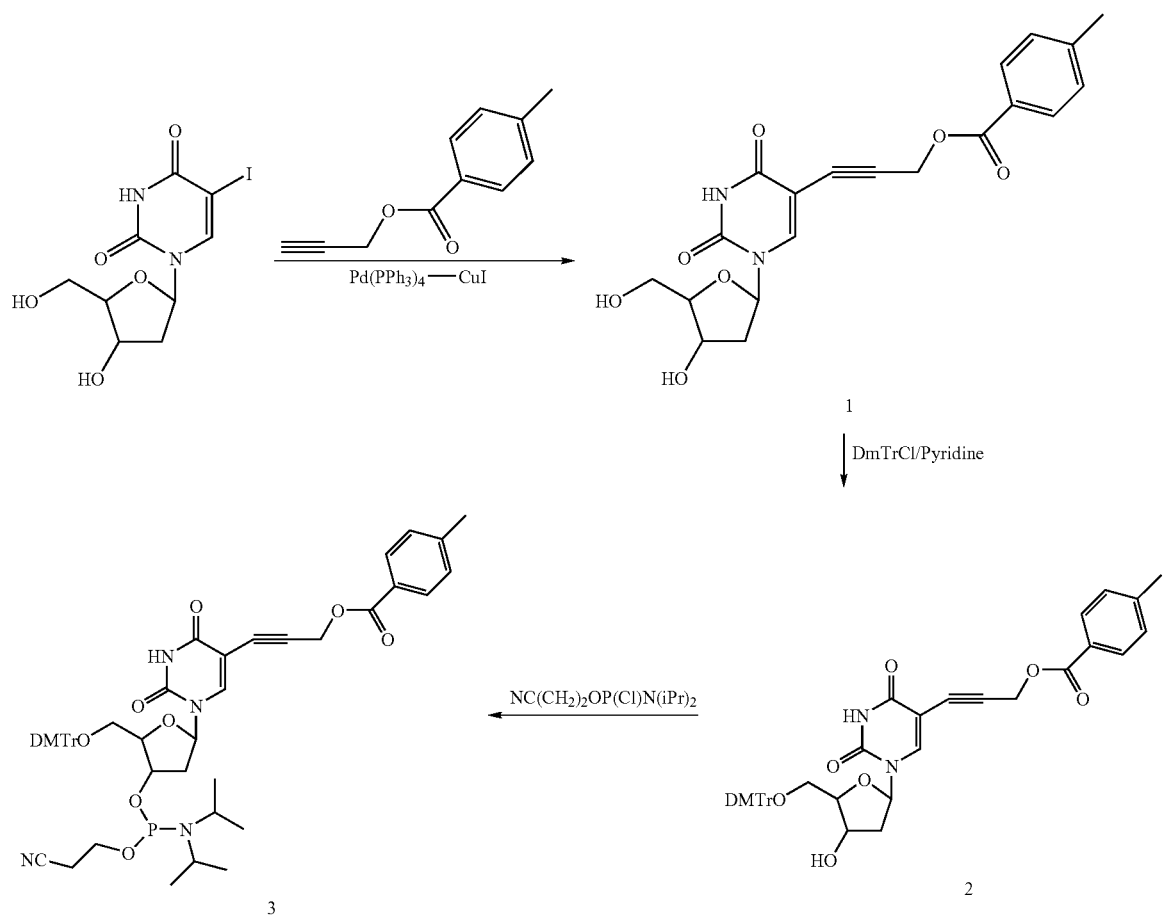

Reaction Schemes 2 and 3 provide one method for the preparation of pyrazolo[3,4-d]pyrimidine phosphoramidites. More particularly, these schemes illustrate the preparation of 3-[-4((1E)-1-aza-2-methylprop-1-enyl)-1-((2R,5R)-4-{[bis(methylethyl)amino](2-cyanoethoxy)phosphinooxy}-5-{[bis(4-methoxyphenyl)phenylmethoxy]methyl}oxolan-2-yl)pyrazolo[3,4-d]pyrimidin-3-yl]prop-2-ynyl 4-methylbenzoate (13; $R_1$=—OCOPhCH$_3$) is synthesized in two portions.

Reaction Scheme 2

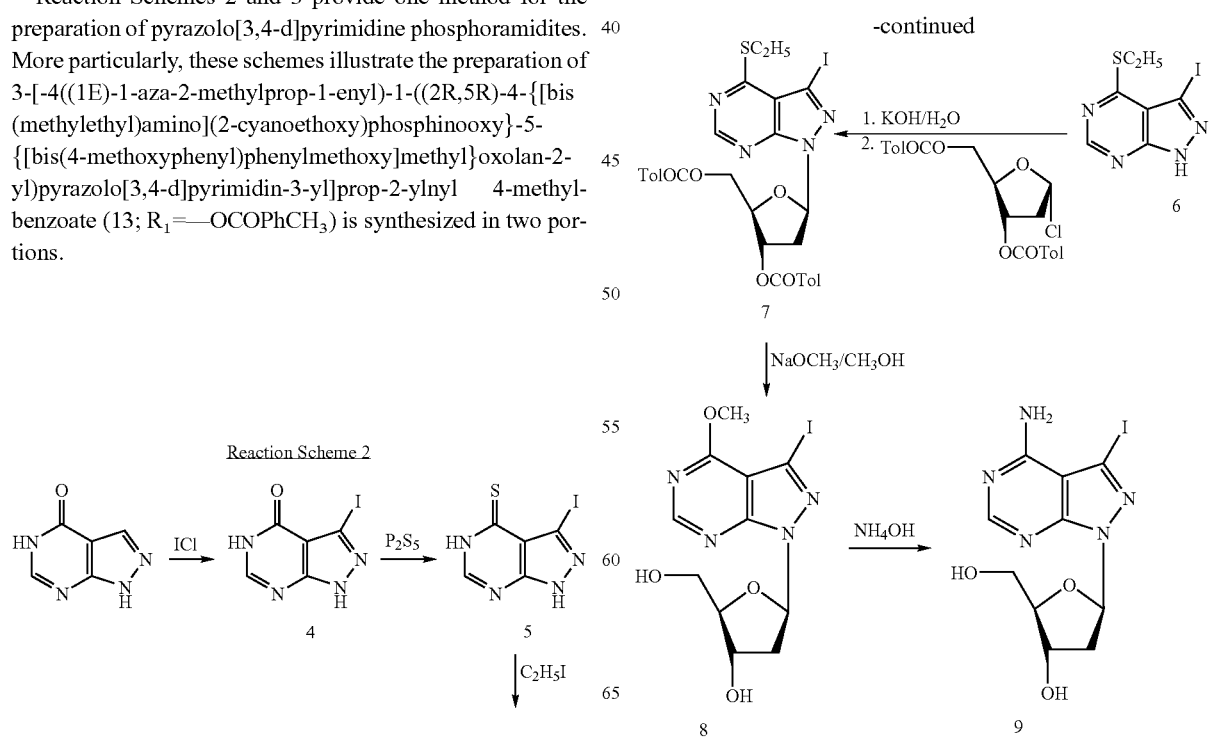

In the first portion (Reaction Scheme 2), (2R,5R)-5-(4-amino-3-iodopyrazolo[3,4-d]pyrimidinyl)-2-(hydroxymethyl)oxolan-3-ol (9) was synthesized starting from 1,5-hydropyrazolo[3,4-d]pyrimidin-4-one. The starting material was treated with iodine monochloride and $P_2S_5$ successively to yield the iodo (4) and thione (5) derivatives respectively. The thione (5) was converted to the ethylthio-derivative (6), which was combined with a 1-chloro-1,2-dideoxy-3,5-di-O-toluoylribofuranose derivative to yield the blocked nucleoside (7). Reaction of compound (7) with sodium methoxide followed by ammonium hydroxide gave hydroxymethyl derivative (8) and compound (9) respectively.

In the second portion (Reaction Scheme 3), 2,3-[-4 ((1E)-1-aza-2-methylprop-1-enyl)-1-((2R,5R)-4-{[bis(methylethyl)amino](2-cyanoethoxy)phosphinooxy}-5-{[bis (4-methoxyphenyl) phenylmethoxy]methyl}oxolan-2-yl) pyrazolo[3,4-d]pyrimidin-3-yl]prop-2-ylnyl 4-methylbenzoate (13 $R_1$=—OCOPhCH$_3$) was prepared starting from compound (9). Compound (9) was reacted with prop-2-ynyl 4-methylbenzoate in the presence of Pd(PPh$_3$)$_4$—CuI to yield the prop-2-ynyl derivative (10; $R_1$=—OCOPhCH$_3$). The amino group in this compound was protected by reaction with N,N dimethylacetamide dimethyl acetal to give (11; $R_1$=—OCOPhCH$_3$). Compound (11; $R_1$=—OCOPhCH$_3$) was converted to the DMTr derivative (12; $R_1$=—OCOPhCH$_3$) and then to the phosphoramidite (13; $R_1$=—OCOPhCH$_3$).

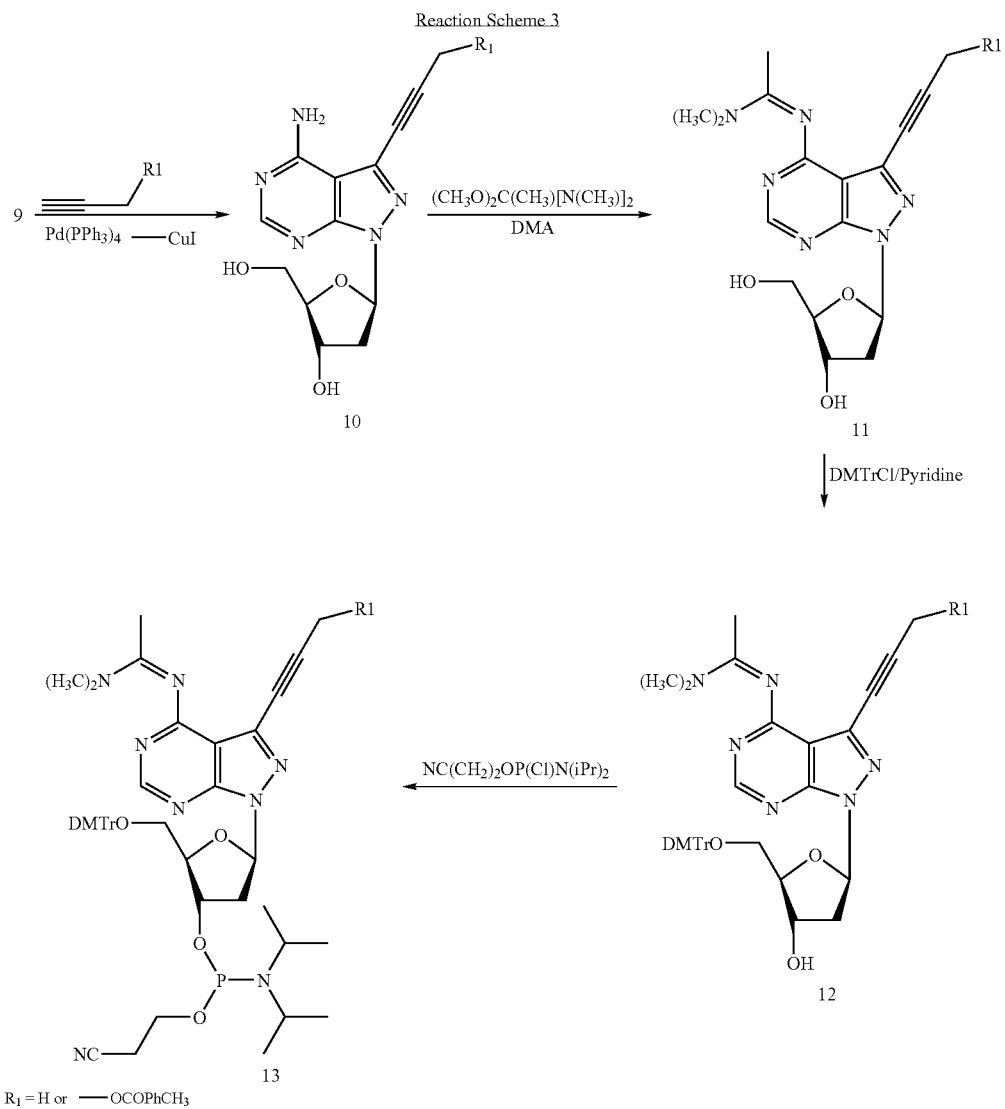

Reaction Scheme 4 illustrates the preparation of N-{3-[1-((2R,5R)-5-{bis(4-methoxyphenyl)phenylmethoxy]methyl}-4-{[bis(methylethyl)amino](2-cyanoethoxy) phosphinooxy}oxolan-2-yl)-6-amino-4-oxo(5-hydropyrazolo[3,4-d]pyrimidin-3-yl)]propyl}-2,2,2-trifluoroacetamide (22).

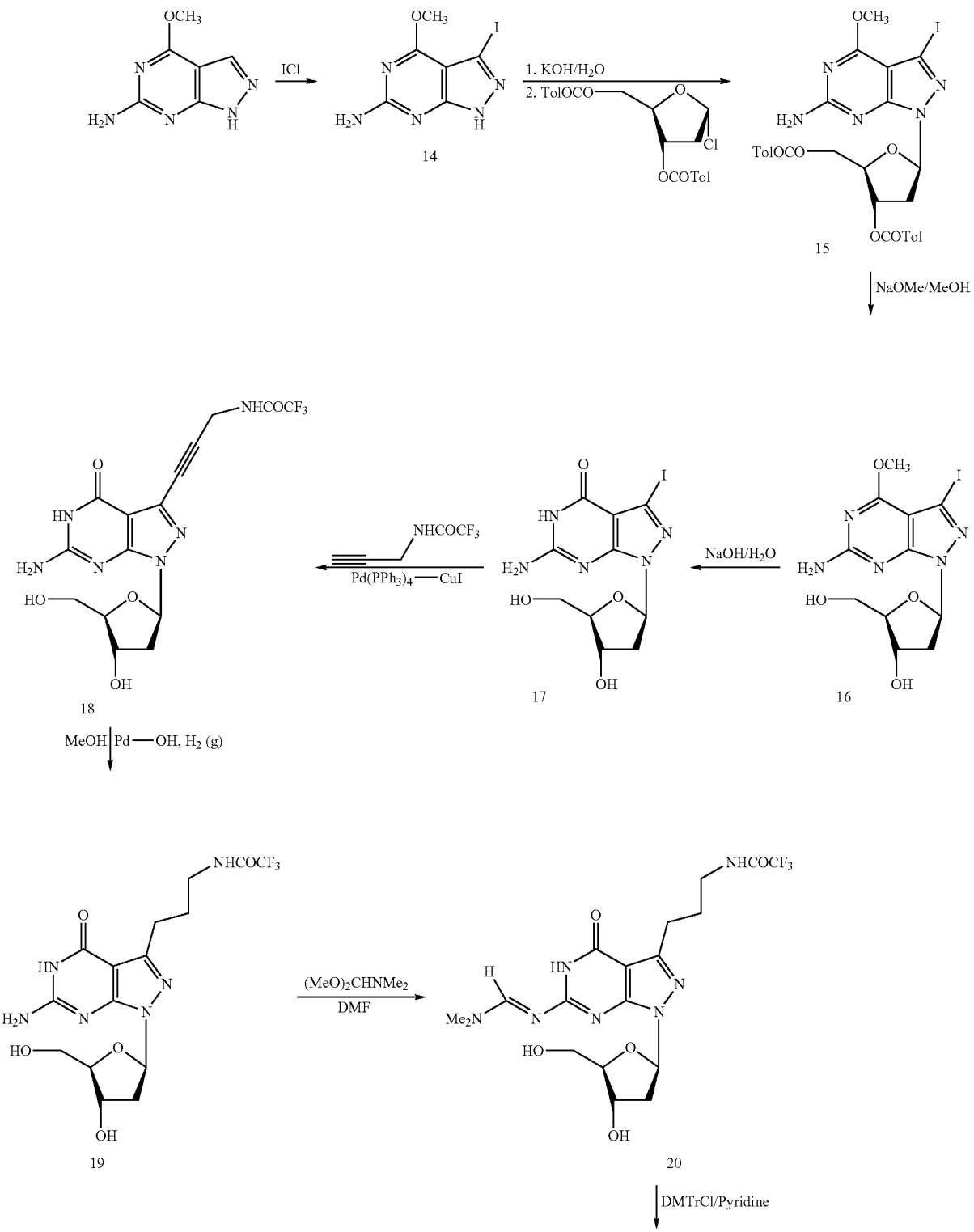

-continued

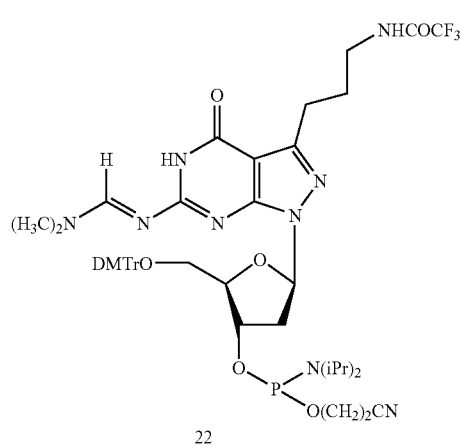

22

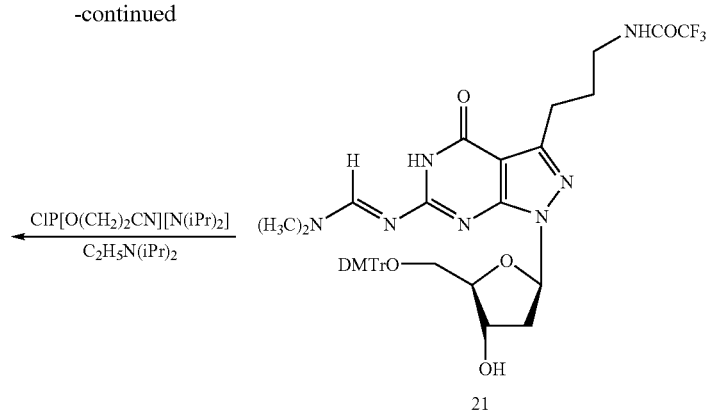

21

In Reaction Scheme 4, 6-amino-4-methoxypyrazolo[3,4-d]pyrimidine was converted to the iodo derivative (14) which was treated with 1-chloro-1,2-dideoxy-3,5-di-O-toluoylribofuranose to yield the nucleoside (15). Compound (15) was treated with NaOMe/MeOH to hydrolyze the toluoyl groups and yield the unblocked nucleoside (16). Treatment of (16) with aqueous sodium hydroxide gave (17) which could be converted to the trifluoro-N-prop-2-ynyl acetamide derivative (18). Compound (18) was reduced with hydrogen and a Pd catalyst to yield the trifluoro-N-propylacetamide derivative (19). The 4-amino group of compound (19) was protected by treatment with N,N-dimethylformamide dimethylacetal to give compound (20) which was converted to DMTr derivative (21) and then to the phosphoramidite derivative (22).

Compounds of Formula 4 (3-[((2R,5R)-5-(6-amino-4-oxo-3-prop-1-ynyl(5-hydropyrazolo[3,4-d]pyrimidinyl))-2-{[bis(4-methoxyphenyl)phenylmethoxy]-methyl}oxolan-3-yloxy)[bis(methylethyl)amino]phosphinooxy]propanenitrile) (PPPG phosphoramidite) can be synthesized using some of the reactions in Reaction Scheme 4.

-continued

Formula 5

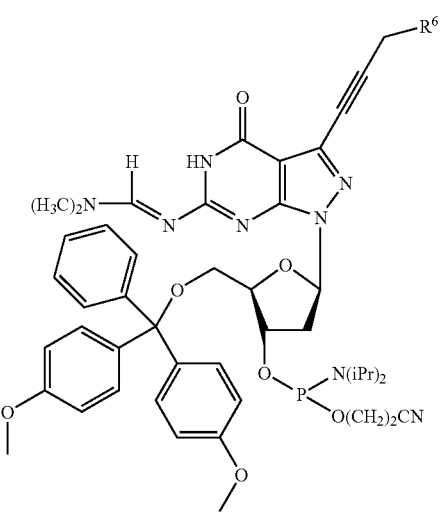

In the conversion of (17) to (18), prop-1-yne is used in place of 2,2,2-trifluoro-N-prop-2-ynylacetamide. The 6-amino group can be protected as described for compound (20) and the 5'-hydroxyl can be protected with a DMTr group as described for compound (21). Finally the phosphoramidite can be prepared as described for compound (22) to yield the compound of Formula 4. In a similar way compounds of Formula 5 where $R^6$ is —OCOPhCH$_3$ or —NHCOCF$_3$. can be prepared using related reactions known in the art.

Reaction Scheme 5 illustrates the preparation of 3-{[5-(4,6-bis{(1E)-1-aza-2-[bis(2-methylpropyl)amino]vinyl}-3-prop-1-ynylpyrazolo[3,4-d]pyrimidinyl)-2-{[bis(4-methoxyphenyl)phenylmethoxy]-methyl}oxolan-3-yloxy][ethyl(methylethyl)amino]-phosphino}propanenitrile (26).

Formula 4

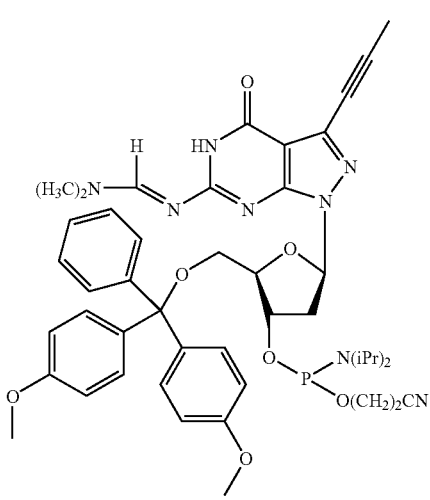

Reaction Scheme 5

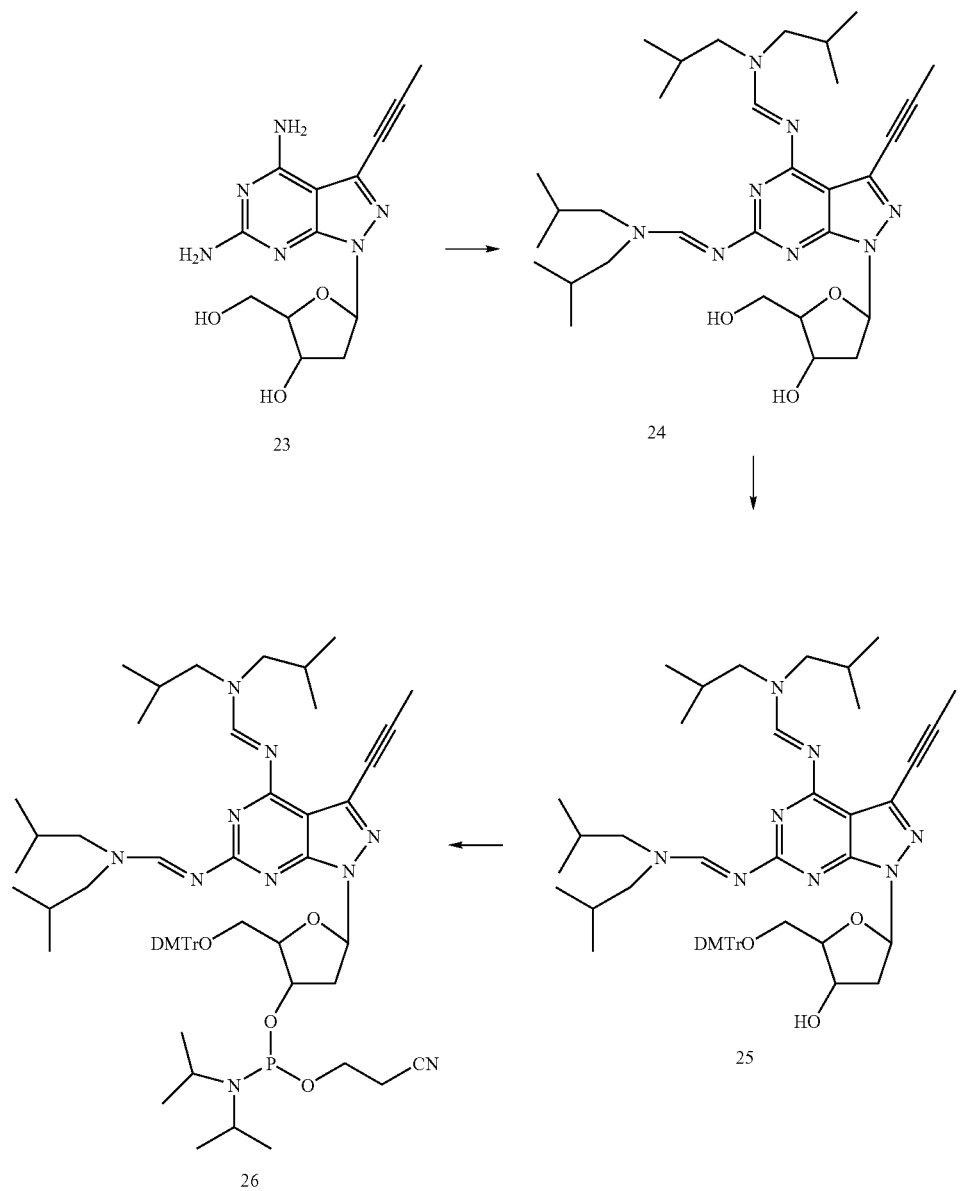

Compound (26) can be synthesized starting from (NH$_2$)$_2$PPPA (23) (see, Seela & Driller, *Helv. Chim. Acta* 71:757-761(1988)). Compound (23) can be converted to the bis(m-ethylethyl)amino derivative (24) (Vincent et al, *J. Org. Chem.*, 64:991-997 (1999)), followed by reaction first with DMTrCl to yield (25) that can be converted to the phosphoramidite (26).

Reaction Scheme 6 provides the synthesis of protected 3-substituted pyrazolo[3,4-d]pyrimidines in which the substituent is a heteroalkyl group.

Reaction Scheme 6
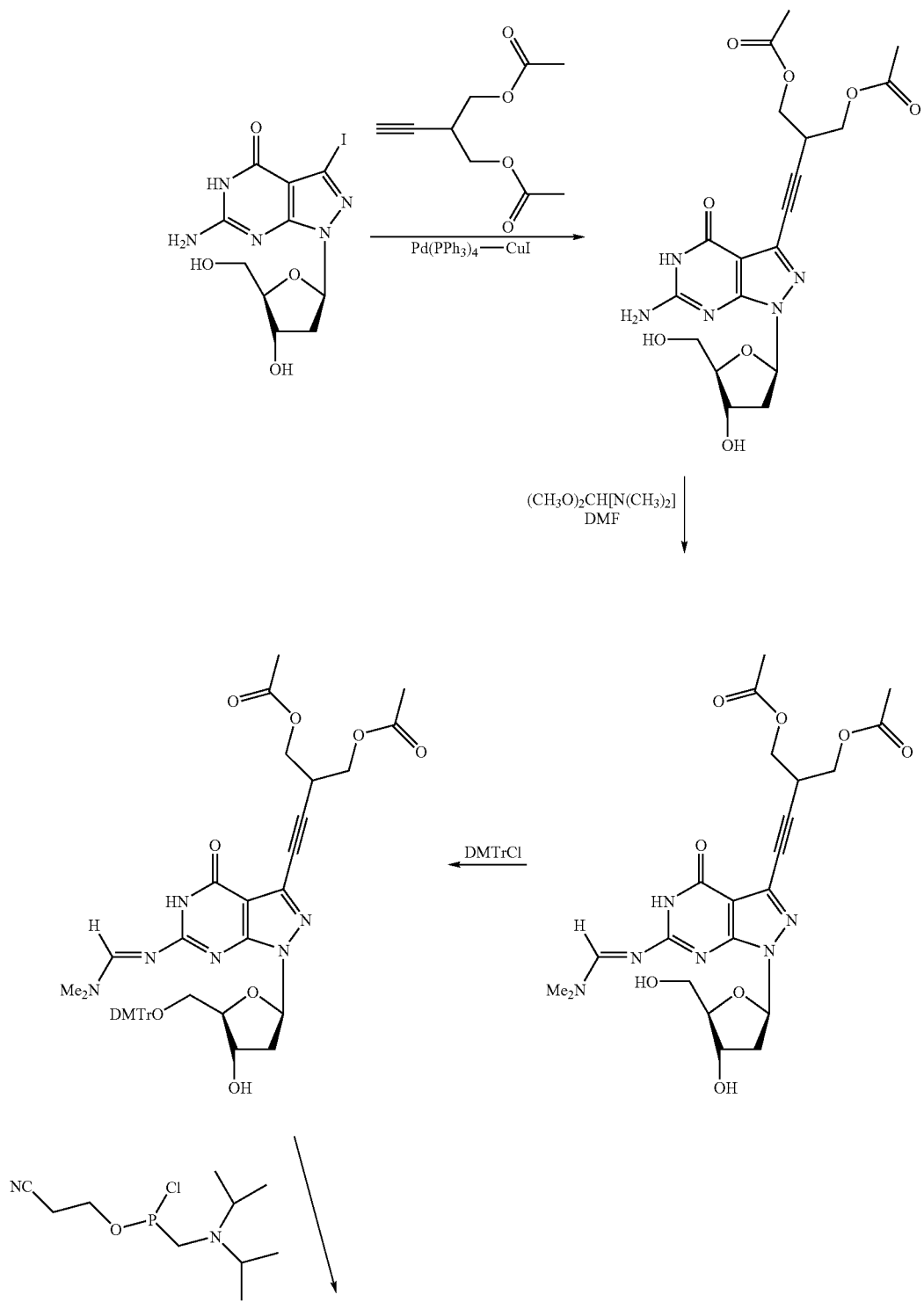

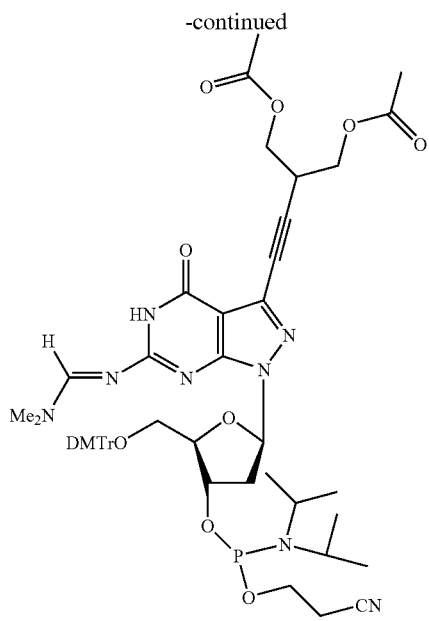

Reaction Scheme 7 provides the synthesis of protected 3-substituted pyrazolo[3,4-d]pyrimidine in which the substituent is a methoxypropynyl group. The 3-iodo diamino derivative (23) was reacted with Pd(PPh$_3$)$_4$—CuI, triethylamine in anhydrous DMF followed by methyl propargyl ether to yield the 3-methoxypropynyl-2,4-diaminopyrazolo [3,4-d]pyrimidine derivative (27). The amino groups in this compound were blocked by reaction with N,N-dimethylformamide dimethylacetal to yield (28). The blocked nucleoside was first reacted with dimethoxytrityl chloride and then with 2-cyanoethyl diisopropylchlorophosphoramidite to yield the desired blocked phosphoramidite (29).

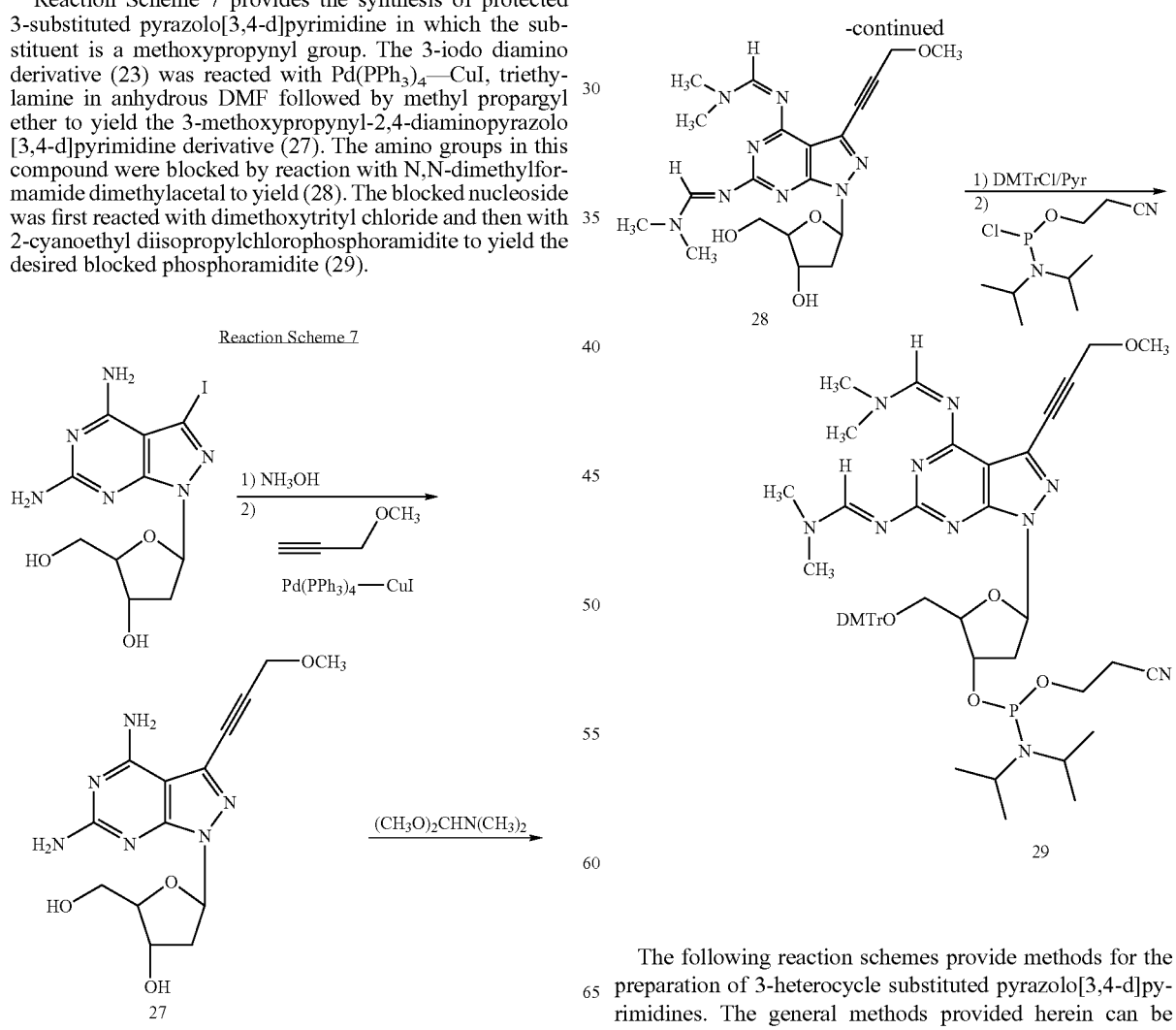

The following reaction schemes provide methods for the preparation of 3-heterocycle substituted pyrazolo[3,4-d]pyrimidines. The general methods provided herein can be adapted for the preparation of other heterocyclic substituents.

Reaction Scheme 8

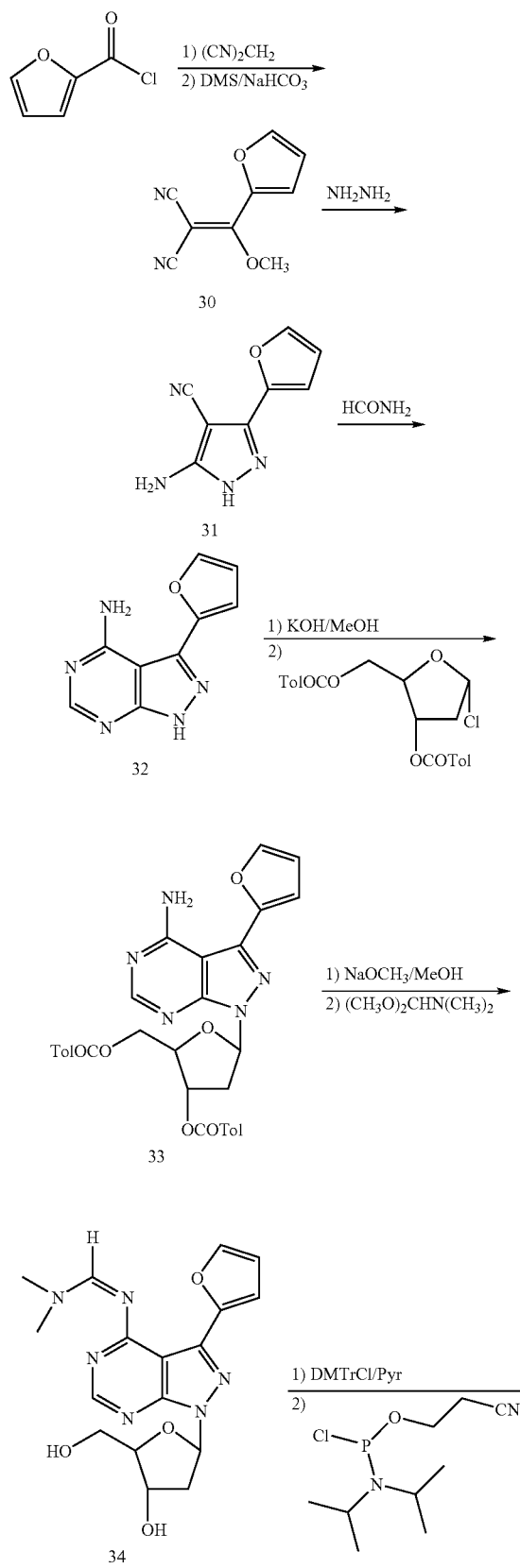

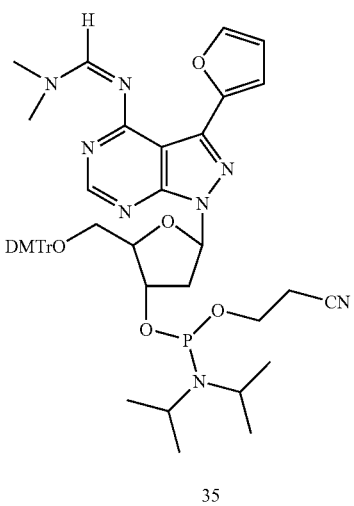

Reaction Scheme 8 provides the synthesis of protected 3-substituted pyrazolo[3,4-d]pyrimidine in which the substituent is a furanyl group. Malononitrile was reacted with 2-furfuryl chloride in the presence of a base, followed by treatment with dimethylsulfide to give the methoxy dinitrile derivative (30). Reaction of (30) with hydrazine yielded the substituted pyrazole (31) which was reacted with formamide to give 3-(2-furyl)pyrazolo[3,4-d]pyrimidine-4-ylamine (32). Base (32) was treated with 1-chloro-1,2-dideoxy-3,5-di-O-toluoylribofuranose to yield the blocked nucleoside (33). Compound (33) was first treated with NaOMe/MeOH to hydrolyze the toluoyl groups to yield the unblocked nucleoside which was reacted with N,N-dimethylformamide dimethylacetal to yield the protected nucleoside derivative (34). This derivative was first reacted with dimethoxytrityl chloride and then with 2-cyanoethyl diisopropylchlorophosphoramidite to yield the desired blocked phosphoramidite (35).

Reaction Scheme 9

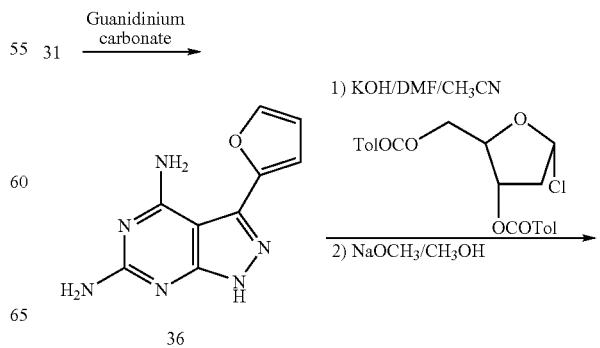

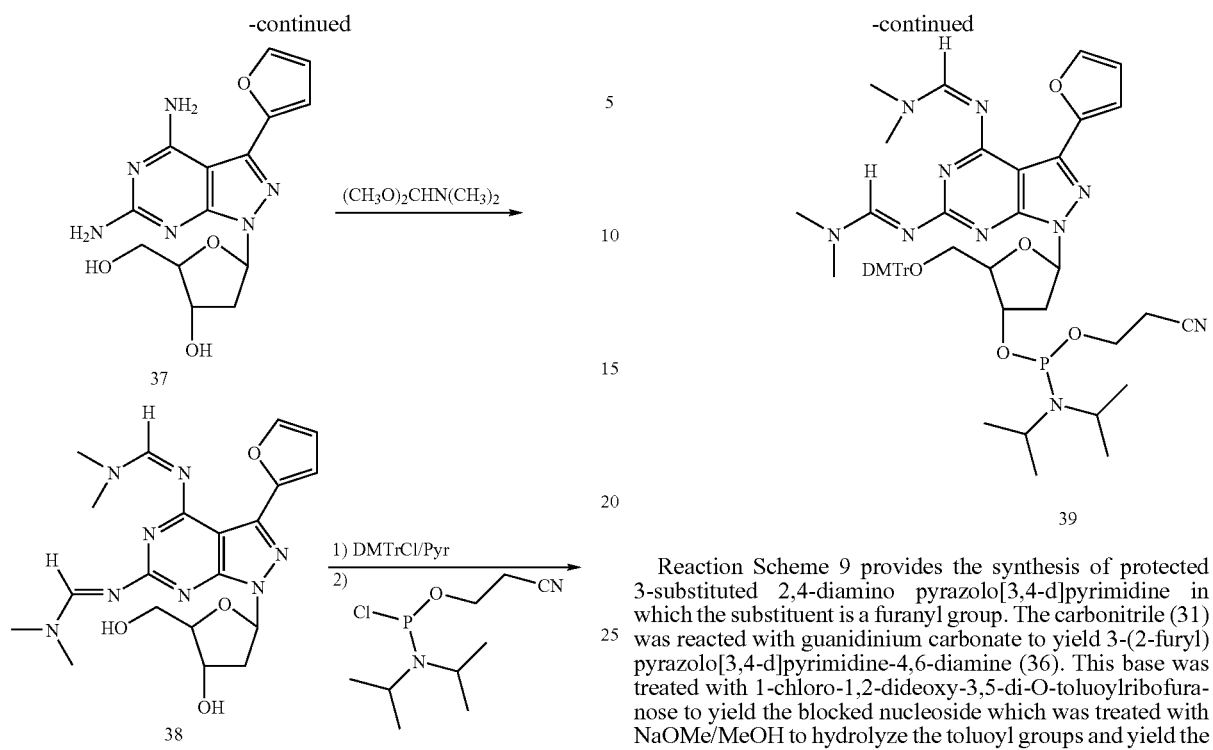

Reaction Scheme 9 provides the synthesis of protected 3-substituted 2,4-diamino pyrazolo[3,4-d]pyrimidine in which the substituent is a furanyl group. The carbonitrile (31) was reacted with guanidinium carbonate to yield 3-(2-furyl) pyrazolo[3,4-d]pyrimidine-4,6-diamine (36). This base was treated with 1-chloro-1,2-dideoxy-3,5-di-O-toluoylribofuranose to yield the blocked nucleoside which was treated with NaOMe/MeOH to hydrolyze the toluoyl groups and yield the unblocked nucleoside derivative (37). The latter compound was reacted with N,N-dimethylformamide dimethylacetal to yield the protected nucleoside derivative (38). This derivative was first reacted with dimethoxytrityl chloride and then with 2-cyanoethyl diisopropylchlorophosphoramidite to yield the desired blocked phosphoramidite (39).

Reaction Scheme 10

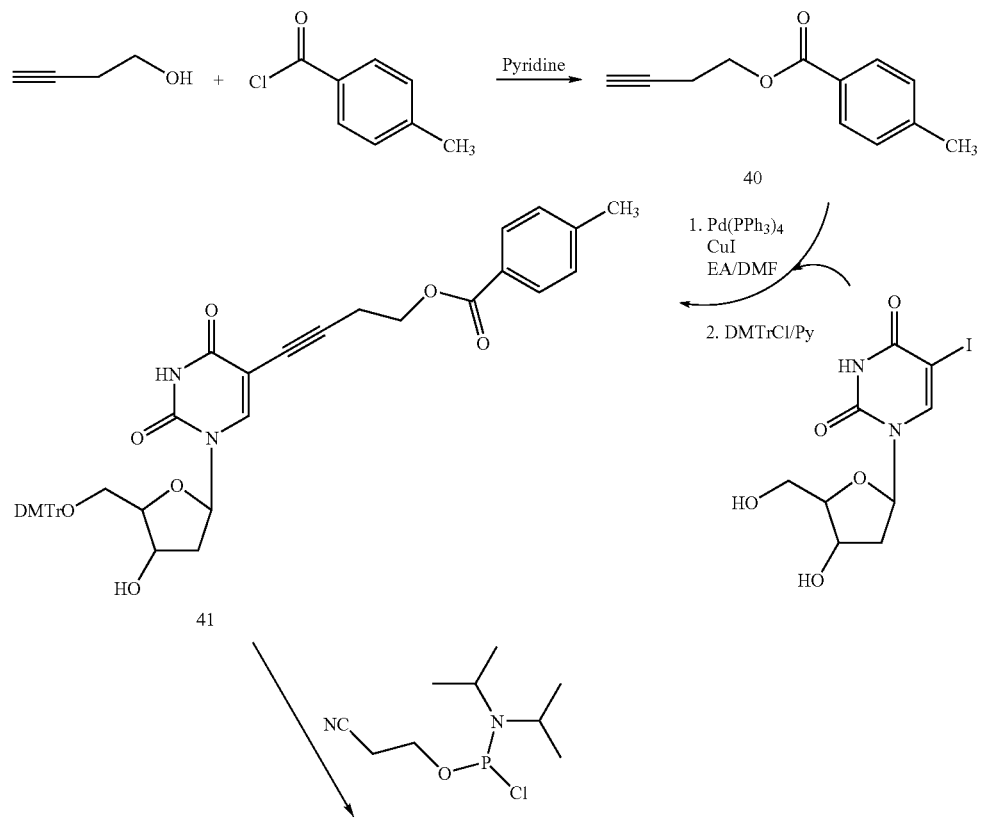

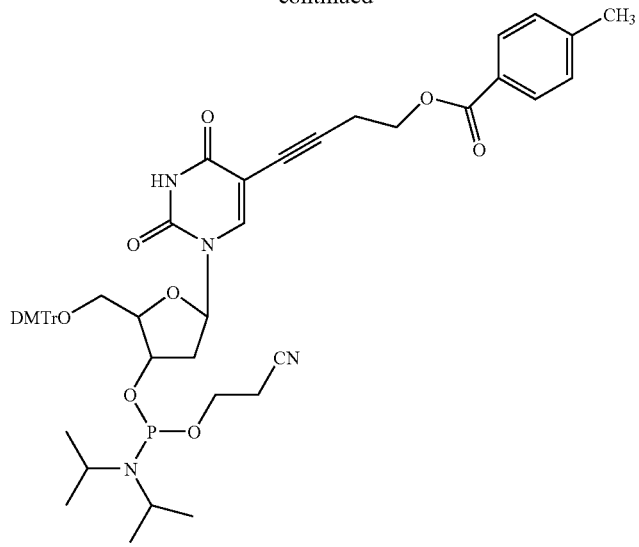

42

Reaction Scheme 10 provides one synthesis route to a hydroxy-protected HOBU-phosphoramidite. In this scheme, 3-butyn-1-ol is converted to its p-toluoyl ester (40) with p-toluoyl chloride in the presence of pyridine. The protected butynol is combined with 5-iodo-2'-deoxyuridine in the presence of tetrakis(triphenylphosphine)palladium(0) and copper iodide, then protected (as a DMT ether) to form 41, which can then be converted to its corresponding phosphoramidite derivative 42. Reagent 42 can be used directly in the preparation of modified oligonucleotides. Removal of the p-toluoyl protected group can be accomplished according to standard methods.

In each of the above schemes, one of skill in the art will understand that other protecting groups and/or activating groups can be used. Additionally, different non-natural base-containing monomers, with different functional groups, can require different blocking groups for successful synthesis of the modified, oligonucleotides. A variety of useful protection groups, their synthesis and de-protection methods are described in, for example, Beaucage & Iyer, *Tetrahedron* 48:2223-2311 (1992).

The synthesis of oligonucleotides, and modified oligonucleotides can be initiated from a solid support containing a cleavable linker to which is attached the first base. The oligonucleotides of the invention can be synthesized containing a substituted pyrazolo[3,4-d]pyrimidine as the first nucleotide at the 3'-end, using an appropriate 3-substituted pyrazolo[3,4-d]pyrimidine. Alternatively, a 5-substituted pyrimidine can be attached initially to a solid support. Reaction Scheme 11 illustrates a general approach to the synthesis of a protected 3-substituted pyrazolo[3,4-d]pyrimidine dA CPG derivative (C). Intermediate (A) can be prepared using procedures described in Reaction Scheme 3, while (B) and (C) can be synthesized as described in co-pending U.S. application Ser. No. 09/457,616.

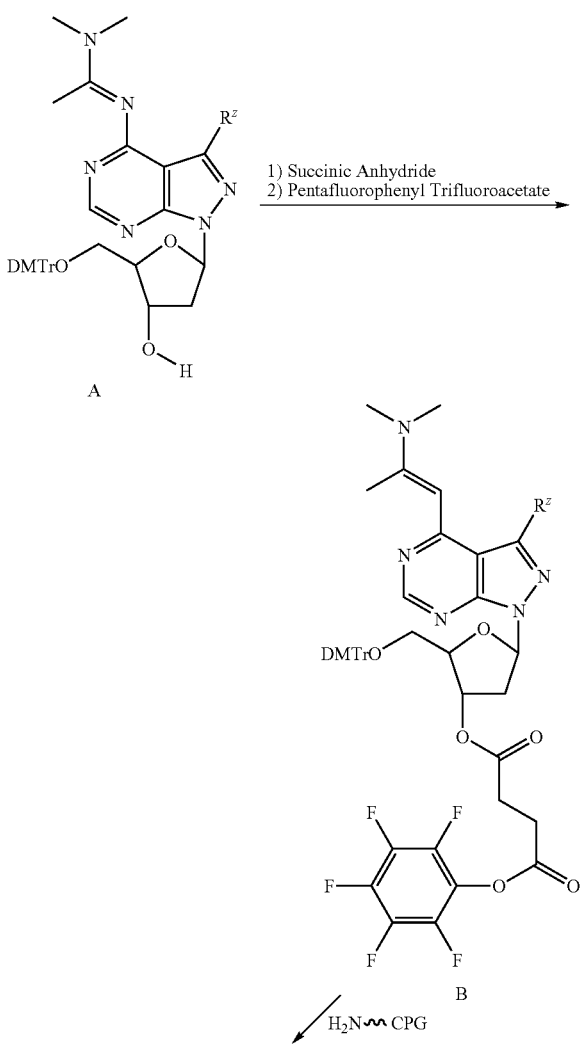

Reaction Scheme 11

-continued

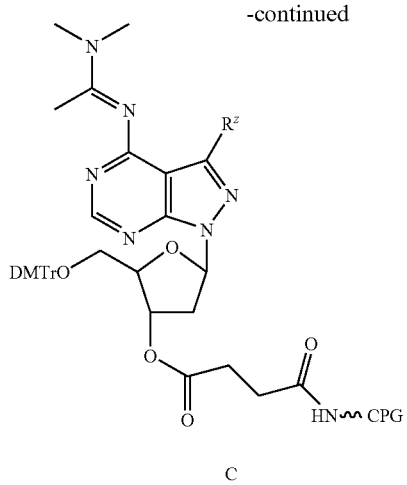

C

In this aspect of the invention, a variety of solid supports are useful, provided the support is compatible with automated oligonucleotide techniques and include, glass, polystyrene, nylon, plastic and the like. Additionally, the present invention provides in a related aspect, a solid support (e.g., controlled pore glass (CPG)) having an attached modified base, preferably those of formulae Ic, Id, Ie, If, IIb, IIc, IId, IIe. More preferably, the attached modified base is a 3-substituted pyrazolo[3,4-d]pyrimidine or a 5-substituted pyrimidine moiety wherein the substituents are selected from the preferred groups described above, and further including the novel bases described in more detail below.

The present invention further includes those compositions and methods wherein any of the unsubstituted and/or 3-substituted pyrazolo[3,4-d]pyrimidines and/or 5-substituted pyrimidines are combined or used in combination with other modified bases known in the art. Other modified monomeric units have been disclosed Scheit, NUCLEOTIDE ANALOGS, John Wiley, New York, 1980; Uhlman and Meyman, *Chemical Reviews*, 90:543-584 (1990), Seela and Debelak, *Nucl. Acids Res.*, 28:3224-3232 (2000); Balow et al, *Nucl. Acids Res.*, 26:3350-3357 (1998); Bolli et al *Nucl. Acids Res.*, 24:4660-4667 (1996).

Modified Oligonucleotide Arrays

In another embodiment of the present invention, modified oligonucleotides are used in procedures which utilize arrays of oligonucleotides, such as sequencing by hybridization and array-based analysis of gene expression. A variety of arrays are contemplated by the present invention including, for example, chip or platform arrays, bead arrays, liquid phase arrays, 'zip-code' arrays and the like. In sequencing by hybridization, an ordered array of oligonucleotides of different known sequences is used as a platform for hybridization to one or more test polynucleotides, nucleic acids or nucleic acid populations. Determination of the oligonucleotides which are hybridized and alignment of their known sequences allows reconstruction of the sequence of the test polynucleotide. Alternatively, oligonucleotides comprising the wild-type sequence and all possible mutant sequences for a given region of a gene of interest can be placed on an array. Exposure of the array to DNA or RNA from a subject or biological specimen, under hybridization conditions, allows determination of wild-type or mutant status for the gene of interest. See, for example, U.S. Pat. Nos. 5,492,806; 5,525,464; 5,556,752; and PCT Publications WO 92/10588 and WO 96/17957. Both of these techniques require discrimination between related sequences, especially at the single-nucleotide level; hence, the enhanced discriminatory properties of the modified oligonucleotides of the invention will provide improvements in these techniques. Materials for construction of arrays include, but are not limited to, nitrocellulose, glass, silicon wafers, optical fibers and other materials suitable for construction of arrays such as are known to those of skill in the art. The synthesis of oligonucleotides arrays has been described in co-pending U.S. application Ser. No. 09/364,320, and suitable modifications can be made to the methods therein for preparing the arrays of the present invention.

An additional application of the present invention to array technology is in the examination of patterns of gene expression in a particular cell or tissue. In this case, oligonucleotides or polynucleotides corresponding to different genes are arrayed on a surface, and a nucleic acid sample from a particular cell or tissue type, for example, is incubated with the array under hybridization conditions. Detection of the sites on the array at which hybridization occurs allows one to determine which oligonucleotides have hybridized, and hence which genes are active in the particular cell or tissue from which the sample was derived.

Array methods can also be used for identification of mutations or polymorphisms, where wild-type and mutant sequences are placed in an ordered array on a surface. Hybridization of a polynucleotide sample to the array under stringent conditions, and determination of which oligonucleotides in the array hybridize to the polynucleotide, allows determination of whether the polynucleotide possesses the wild-type or the mutant sequence. Since many mutant sequences of clinically-relevant genes differ from their wild-type counterpart at only one or a few nucleotide positions, the enhanced discriminatory powers of the modified oligonucleotides of the invention will provide improvements in mutation detection.

In all of the above-mentioned applications of array technology, the increased discriminatory abilities of modified oligonucleotide provide significant improvements in sensitivity and resolving power.

Figure 2:
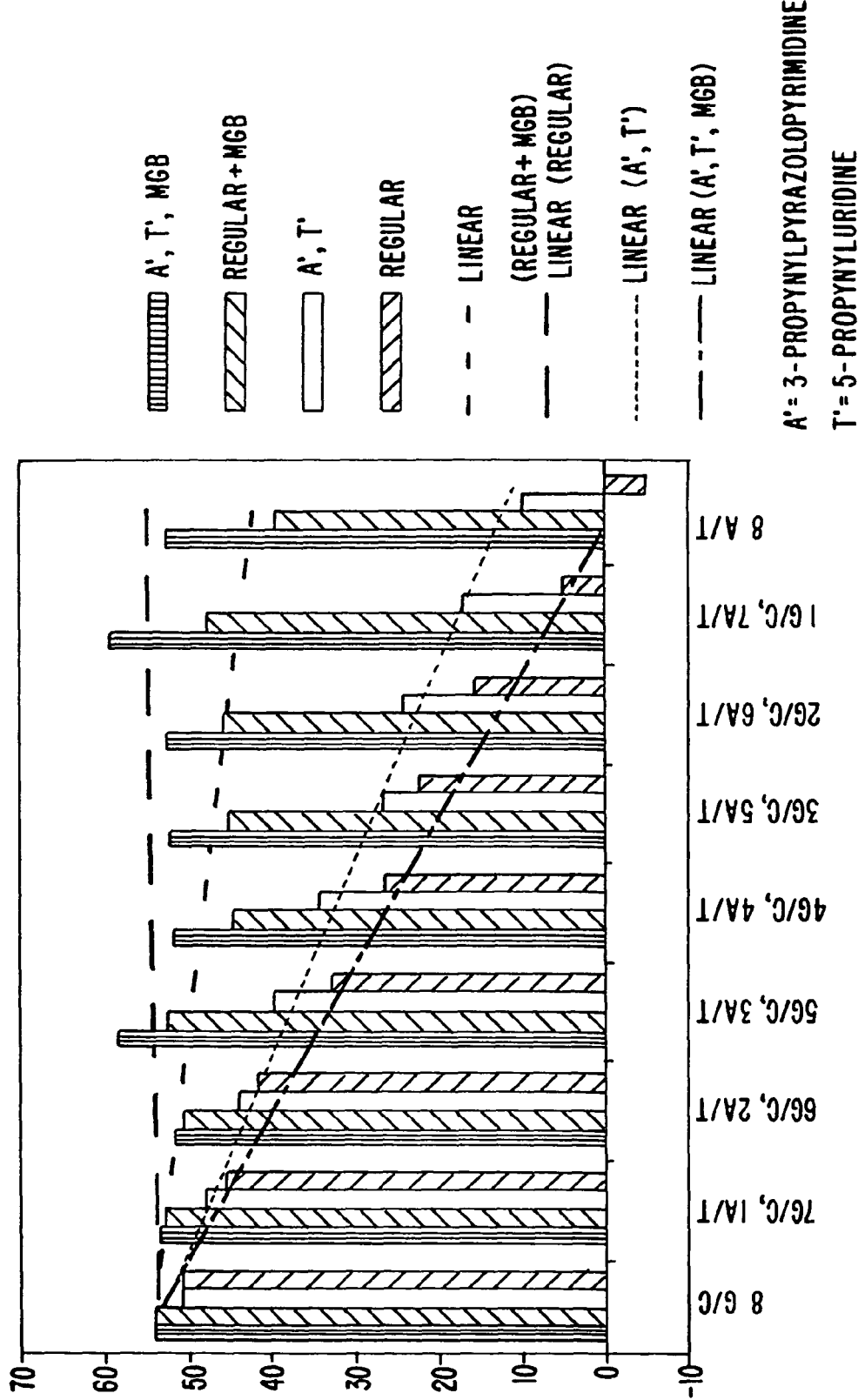
FIG. 2 is a graph illustrating the balancing of the $T_m$ of 8-mer GC-rich and AT-rich probes with different combinations of MGB, PPPA and PU.

Efficient hybridization, for example in arrays, requires that the capture probes contain $T_m$'s in a narrow temperature range. In one embodiment of the invention the $T_m$ of capture oligonucleotides for use in arrays is balanced, eliminating the problem associated with GC and AT-rich sequences, by using a combination of 3'-MGBs and modified bases (e.g., PPPA and PPPU). Table 1 and FIG. 2 illustrate the balancing of the $T_m$ of pyrimidine rich probes with different G/C and A/T base pairs. To balance the $T_m$ of the different probes, PPPA, PU and MGB were used in combination. The purine and pyrimidine-rich probes and complementary targets are shown in Table 1 and the $T_m$s of these probes are shown in FIG. 2. As shown in FIG. 2 the $T_m$ difference between a GC-rich and an AT-rich probe can be more than 50° C.

TABLE 1

Sequences of Oligonucleotide Probes and Complementary Targets

| Complementary Targets | SEQ ID NO: | Py/Pu-rich probes | base pairs |
|---|---|---|---|
| 1* TCGGCGGCGT | 8 | 1*. MGB-Q-CGCCGCCG 8 | G/C |
| 2* ACAGCGGCGT | 9 | 2* MGB-Q-CGCCGCTG 7 | G/C, 1 A/T |
| 3* ACAGCGACGT | 10 | 3*. MGB-Q-CGTCGCTG 6 | G/C, 2 A/T |
| 4* TCAGTGACGA | 11 | 4*. MGB-Q-CGTCACTG 5 | G/C, 3 A/T |

TABLE 1-continued

Sequences of Oligonucleotide Probes and Complementary Targets

| Complementary Targets | SEQ ID NO: | Py/Pu-rich probes | base pairs | |
|---|---|---|---|---|
| 5* TCAGTGACAA | 12 | 5*. MGB-Q-TGTCACTG | 4 G/C, | 4 A/T |
| 6* TCAATGACAG | 13 | 6*. MGB-Q-TGTCATTG | 3 G/C, | 5 A/T |
| 7* ACAATGATAA | 14 | 7*. MGB-Q-TATCATTG | 2 G/C, | 6 A/T |
| 8* CCAATAATAA | 15 | 8*. MGB-Q-TATTATTG | 1 G/C, | 7 A/T |
| 9* GTAATAATAA | 16 | 9*. MGB-Q-TATTATTA | 8 A/T | |

As can be seen in FIG. 2, modification with PPPA, PU and a MGB provides a probe set having balanced $T_m$s.

Efficient hybridization for example in arrays, requires that the probes contain $T_m$'s in a narrow temperature range. Thus, in related embodiments, the modified oligonucleotides described herein can comprise any combination of normal bases, unsubstituted pyrazolo[3,4-d]pyrimidine bases (e.g., PPG and PPA), 3-substituted pyrazolo[3,4-d]pyrimidines, modified purine, modified pyrimidine, 5-substituted pyrimidines, universal bases and a minor groove binder to balance the $T_m$ of the oligonucleotide.

The ability to predict and "level" the $T_m$s of multiple modified oligonucleotides is particularly useful for the development of oligonucleotide arrays or for compositions having a plurality of oligonucleotides. Still further, the ability to predict $T_m$s for modified oligonucleotides is useful for establishing appropriate conditions for hybridization, renaturation, mapping variations of base compositions of sequences, determination of sequence complexity and divergence. A $T_m$ prediction algorithm can be developed using models that assign thermodynamic contributions to duplex formation for all possible individual base pair nearest neighbors. Thermodynamic parameters for 10 independent nearest-neighbors of base pairs are available from published sources for DNA:RNA hybrids (see Sugimoto et al., Biochem. 34:11211-11216 (1995)) and dsDNA (SantaLucia et al, Biochem. 36:10581-10595 (1997)). The use of the nearest neighbor parameters to develop programs to calculate oligonucleotide duplex stability in terms of $T_m$ have been described (see, Schutz & von Ahsen, Biotechniques, 27:1218-22 (1999); Owczarzy et al, Biopolymers, 44:217-239 (1997); for PNA/DNA, see Geisen et al, Nucl. Acids Res., 26:5004-5006 (1998); Blake et al, Bioinformatics, 15:370-5 (1999) and U.S. Pat. No. 5,556,749.

The basic principles of thermodynamic and kinetic description of mismatch discrimination are well known and are summarized below.

A probe-target interaction is an equilibrium reaction that can be described as $$A+B \Leftrightarrow AB$$

where A=probe, B=DNA target

At the temperature T equilibrium of forward (association) and reverse (dissociation) reactions can be described by equilibrium constant K where:

$$K = \frac{[AB]}{[A][B]};$$

in terms of equilibrium thermodynamics $$K = \exp(-\Delta H^o{}_{AB}/RT + \Delta S^o{}_{AB}/R);$$

$$\Delta G^o{}_{AB} = \Delta H^o{}_{AB} - T\Delta S^o{}_{AB};$$

$$\Delta G^o{}_{AB} = -RTLn(K)$$

where: $\Delta H^o{}_{AB}$, $\Delta S^o{}_{AB}$ and $\Delta G^o{}_{AB}$—enthalpy, entropy and free energy changes for duplex AB formation.

The duplex AB has N base pairs (N−1 nearest neighbors) and the nearest-neighbor approximation assumes $$\Delta H^o{}_{AB} = \Delta H^o{}_1 + \Delta H^o{}_2 + \ldots \Delta H^o{}_{n-1} + \Delta H^o{}_{init} = \Sigma(\Delta H^o{}_i + \Delta H^o{}_{init})$$

$$\Delta S^o{}_{AB} = \Delta S^o{}_1 + \Delta S^o{}_2 + \ldots \Delta S^o{}_{n-1} + \Delta S^o{}_{init} = \Sigma(\Delta S^o{}_i + \Delta S^o{}_{init})$$

$$\Delta G^o{}_{AB} = \Delta G^o{}_1 + \Delta G^o{}_2 + \ldots \Delta G^o{}_{n-1} + \Delta G^o{}_{init} = \Sigma(\Delta G^o{}_i + \Delta G^o{}_{init})$$

where: $\Delta H^o{}_i$, $\Delta S^o{}_i$ and $\Delta G^o{}_i$—enthalpy, entropy and free energy changes for each nearest-neighbor base pairs increment for duplex AB formation, $\Delta H^o{}_{init}$, $\Delta S^o{}_{init}$ and $\Delta G^o{}_{init}$—thermodynamic parameters of initiation of duplex AB formation.

In the case of total concentration equality, $C_{probe} = C_{target}$, an equation for Tm in terms of free energy, enthalpy and entropy can be arrived at as shown below:

$$TM = \frac{\sum(\Delta H^o_i + \Delta H^o_{init})}{\sum(\Delta S^o_i + \Delta S^o_{init}) + RLn[(C_{probe} + C_{target})/4]}$$

Similarly as shown above relationships can be developed when the probe hybridizes to a target that contains a mismatch, as shown below:

$$A+B^* \Leftrightarrow AB^*$$

A=probe, B*=mismatched DNA target

Thermodynamic parameters for mismatched duplex AB* are: K*, $\Delta H^o{}_{AB*}$, $\Delta S^o{}_{AB*}$ and $\Delta G^o{}_{AB*}$. In terms of nearest-neighbor parameters for a mismatched base pair at position "4", for example, involving nearest-neighbor "3" and "4" the discrimination parameters $\Delta\Delta H^o$, $\Delta\Delta S^o$, $\Delta\Delta G^o$ can be expressed as:

$$\Delta\Delta H^o = \Delta H^o{}_{AB} - \Delta H^o{}_{AB*} = (\Delta H^o{}_3 - \Delta H^{o*}{}_3) + (\Delta H^o{}_4 - \Delta H^{o*}{}_4) = \Delta\Delta H^o{}_3 + \Delta\Delta H^o{}_4.$$

$$\Delta\Delta S^o = \Delta S^o{}_{AB} - \Delta S^o{}_{AB*} = (\Delta S^o{}_3 - \Delta S^{o*}{}_3) + (\Delta S^o{}_4 - \Delta S^{o*}{}_4) = \Delta\Delta S^o{}_3 + \Delta\Delta S^o{}_4.$$

$$\Delta\Delta G^o = \Delta G^o{}_{AB} - \Delta G^o{}_{AB*} = (\Delta G^o{}_3 - \Delta G^{o*}{}_3) + (\Delta G^o{}_4 - \Delta G^{o*}{}_4) = \Delta\Delta G^o{}_3 + \Delta\Delta G^o{}_4.$$

In one embodiment of the invention, probe sequences are designed to determine the thermodynamic nearest-neighbor parameters for oligonucleotides containing normal purines, pyrimidines and a minor groove binder $CDPI_3$ attached to the 3'-end of an oligonucleotide. In another embodiment thermodynamic nearest-neighbor parameters for oligonucleotide containing normal pyrimidines, purines, a 3'-end attached $CDPI_3$, but wherein the guanine is replaced with 5-hydropyrazolo[3,4-d]pyrimin-4-one. These nearest-neighbor thermodynamic parameters are used in these two embodiments to calculate the $T_m$s of these types of oligonucleotides with and without $CDPI_3$. In the case where the $CDPI_3$ was attached at base 1 at the 3'-end the new $T_m$ prediction algorithm and formula were used as derived below.

$$T_M = \frac{\sum(\Delta H_i^o + \Delta H_{init}^o)}{\sum(\Delta S_i^o + \Delta S_{init}^o) + RLn[(C_{probe} + C_{target})/4] + \Delta\Delta S_{MGB}^o}$$

The model assumes that a MGB attached to an oligonucleotide has an additional pure entropic factor $\Delta\Delta S^o_{MGB}$. This value can be calculated according to algorithm: 6 bases (5 nearest-neighbor) from 3'-prime end are covered by the MGB from starting base "1" or "2". Each nearest-neighbors covered has unique value $\Delta\Delta S^o_{iMGB}$. Correction factor "A" are introduced in the case when adenosine can be found in base positions 6, 7 or 8. Statistical factor "n" is introduced additionally to factor "A" were n=3 for -AAA-; n=2 for -AA-, -ANA-; n=1 for -A-; n=0 for -AN— and —NA- (N is any base other than A). A final value $\Delta\Delta S^o_{MGB}$ can be determined by the equation $\Delta\Delta S^o_{MGB} = \Sigma\Delta\Delta S^o_{iMGB} + A\text{(optional)} + R*Ln(N)\text{(optional)}$ Tables 2a and 2b contain the nearest-neighbor thermodynamic parameters for oligonucleotides containing PPG alone and the entropic contribution of the MGB, respectively. In the latter case the contribution of fluorescein and a dark quencher is incorporated in the thermodynamic treatment and has generally been shown to be negligible. [The quencher is part of the linker between the MGB and the oligonulceotide]

TABLES 2a and 2b a) Nearest-neighbor parameters for PPG containing oligonucleotides
b) The entropic contribution of the CDPI₃.

a)

| Number | 5'-3' | ΔH° | ΔS° | ΔG°(65) |
|---|---|---|---|---|
| 1 | AA | −7850 | −22.3 | −324 |
| 2 | AT | −8180 | −23.0 | −411 |
| 3 | AC | −8450 | −22.6 | −795 |
| 4 | AG | −6560 | −17.2 | −730 |
| 5 | TA | −7230 | −21.8 | 129 |
| 6 | TT | −7850 | −22.3 | −324 |
| 7 | TC | −8720 | −24.0 | −614 |
| 8 | TG | −6900 | −18.3 | −715 |
| 9 | CA | 7530 | −20.3 | −652 |
| 10 | CT | −6390 | −17.3 | −548 |
| 11 | CC | −7860 | −20.1 | −1071 |
| 12 | CG | −6030 | −14.0 | −1288 |
| 13 | GA | −10070 | −27.4 | −795 |
| 14 | GT | −9110 | −23.5 | −1175 |
| 15 | GC | −13170 | −34.0 | −1665 |
| 16 | GG | −8080 | −20.2 | −1258 |
| 17 | GCinit | −48440 | −17.6 | 1116 |
| 18 | ATinit | −1060 | −7.1 | 1341 | b)

| Number | 5'-3' | ΔΔS° |
|---|---|---|
| 1 | AA | 3.408 |
| 2 | AT | 3.060 |
| 3 | AC | 1.442 |
| 4 | AG | 0.750 |
| 5 | TA | 2.463 |
| 6 | TT | 3.313 |
| 7 | TC | 2.870 |
| 8 | TG | 0.893 |
| 9 | CA | 0.607 |
| 10 | CT | 2.253 |
| 11 | CC | 0.905 |
| 12 | CG | −0.721 |
| 13 | GA | 1.282 |
| 14 | GT | 2.397 |

TABLES 2a and 2b-continued a) Nearest-neighbor parameters for PPG containing oligonucleotides
b) The entropic contribution of the CDPI₃.

| 15 | GC | 2.172 |
|---|---|---|
| 16 | GG | 1.298 |

In one preferred embodiment $T_m$s of multiple modified oligonucleotides containing the same number of bases are leveled using an algorithm to select nearest neighbor parameters from any combination of normal bases, universal bases, PPA, PPG, PPPA, PPPG, PU, PC, HOPU, HOBuU, HOBuC, $(NH_2)_2$PPPA, $(NH_2)_2$PPPAOH, $(NH_2)_2$BuPPAOH, $(NH_2)_2$PPAI, HOBuPPG, minor groove binder, fluorophore, quencher and a chemilumenescer.

Alternatively the $T_m$s of multiple modified oligonucleotides are substantially leveled for containing the same number of bases plus or minus 1 or 2 bases, with a Tm range of about ±2° C.

In some instances, modified bases are used that improve duplex stability in addition to those modified bases that decrease duplex stability. Modified bases that decrease duplex stability are well known, e.g. 7-deazaadenine and 7-deazaguanine.

Use of Modified Oligonucleotides

The modified oligonucleotides of the present invention provides numerous advantages over unmodified oligonucleotides, including superior mismatch discrimination. The modified oligonucleotides of the invention are particularly useful as probes, wherein the hybridization to a target sequence is detected, or as primers, wherein their hybridization to a target sequence is followed by polynucleotide synthesis initiated from the 3' terminus of the modified oligonucleotide, and the synthesized product (i.e., the extension product) is detected.

The modified oligonucleotides of the present invention are useful in other techniques in which hybridization of an oligonucleotide to another nucleic acid is involved. These include, but are not limited to, techniques in which hybridization of an oligonucleotide to a target nucleic acid is the endpoint; techniques in which hybridization of one or more oligonucleotides to a target nucleic acid precedes one or more polymerase-mediated elongation steps which use the oligonucleotide as a primer and the target nucleic acid as a template; techniques in which hybridization of an oligonucleotide to a target nucleic acid is used to block extension of another primer; techniques in which hybridization of an oligonucleotide to a target nucleic acid is followed by hydrolysis of the oligonucleotide to release an attached label; and techniques in which two or more oligonucleotides are hybridized to a target nucleic acid and interactions between the multiple oligonucleotides are measured. Conditions for hybridization of oligonucleotides, and factors which influence the degree and specificity of hybridization, such as temperature, ionic strength and solvent composition, are well-known to those of skill in the art. See, for example, Sambrook et al., supra; Ausubel, et al., supra; M. A. Innis et al. (eds.) PCR Protocols, Academic Press, San Diego, 1990; B. D. Hames et al. (eds.) Nucleic Acid Hybridisation: A Practical Approach, IRL Press, Oxford, 1985; and van Ness et al. (1991) *Nucleic Acids Res.* 19:5143-5151.

Hybridization of probes and/or primers to target sequences proceeds according to well-known and art-recognized base-pairing properties, such that adenine base-pairs with thymine or uracil, and guanine base-pairs with cytosine. The property of a nucleotide that allows it to base-pair with a second nucleotide is called complementarity. Thus, adenine is complementary to both thymine and uracil, and vice versa; similarly, guanine is complementary to cytosine and vice versa. An oligonucleotide which is complementary along its entire length with a target sequence is said to be perfectly complementary, perfectly matched, or fully complementary to the target sequence, and vice versa. An oligonucleotide and its target sequence can have related sequences, wherein the majority of bases in the two sequences are complementary, but one or more bases are noncomplementary, or mismatched. In such a case, the sequences can be said to be substantially complementary to one another. If the sequences of an oligonucleotide and a target sequence are such that they are complementary at all nucleotide positions except one, the oligonucleotide and the target sequence have a single nucleotide mismatch with respect to each other.

The modified pyrazolo[3,4-d]pyrimidine nucleotides of the invention retain the base-pairing specificity of their naturally-occurring analogues; PPPG analogues are complementary to cytosine, while PPPA analogues are complementary to thymine and uracil. The PPPG and PPPA analogues not only have a reduced tendency for so-called "wobble" pairing with non-complementary bases, compared to guanine and adenine, but the 3-substituted groups increase binding affinity in duplexes. Similarly, modified pyrimidines hybridize specifically to their naturally occurring counter partners.

Conditions for hybridization are well-known to those of skill in the art and can be varied within relatively wide limits. Hybridization stringency refers to the degree to which hybridization conditions disfavor the formation of hybrids containing mismatched nucleotides, thereby promoting the formation of perfectly matched hybrids or hybrids containing fewer mismatches; with higher stringency correlated with a lower tolerance for mismatched hybrids. Factors that affect the stringency of hybridization include, but are not limited to, temperature, pH, ionic strength, concentration of organic solvents such as formamide and dimethylsulfoxide and chaotropes. As is well known to those of skill in the art, hybridization stringency is increased by higher temperatures, lower ionic strengths, and lower solvent concentrations. See, for example, Ausubel et al., supra; Sambrook et al., supra; M. A. Innis et al. (eds.) PCR Protocols, Academic Press, San Diego, 1990; B. D. Hames et al. (eds.) Nucleic Acid Hybridisation: A Practical Approach, IRL Press, Oxford, 1985; and van Ness et al., (1991) *Nucleic Acids Res.* 19:5143-5151.

Thus, in the formation of hybrids (duplexes) between an oligonucleotide and its target sequence, the oligonucleotide is incubated in solution, together with a polynucleotide containing the target sequence, under conditions of temperature, ionic strength, pH, etc, that are favorable to hybridization, i.e., under hybridization conditions. Hybridization conditions are chosen, in some circumstances, to favor hybridization between two nucleic acids having perfectly-matched sequences, as compared to a pair of nucleic acids having one or more mismatches in the hybridizing sequence. In other circumstances, hybridization conditions are chosen to allow hybridization between mismatched sequences, favoring hybridization between nucleic acids having fewer mismatches.

The degree of hybridization of an oligonucleotide to a target sequence, also known as hybridization strength, is determined by methods that are well-known in the art. A preferred method is to determine the $T_m$ of the hybrid duplex. This is accomplished, as described supra, by subjecting a duplex in solution to gradually increasing temperature and monitoring the denaturation of the duplex, for example, by absorbance of ultraviolet light, which increases with the unstacking of base pairs that accompanies denaturation. $T_m$ is generally defined as the temperature midpoint of the transition in ultraviolet absorbance that accompanies denaturation. Alternatively, if $T_m$s are known, a hybridization temperature (at fixed ionic strength, pH and solvent concentration) can be chosen that it is below the $T_m$ of the desired duplex and above the $T_m$ of an undesired duplex. In this case, determination of the degree of hybridization is accomplished simply by testing for the presence of hybridized probe.

If a probe comprises a detectable label, assays for hybridized probe are usually designed to detect the presence of label in duplex material. This can be accomplished, for example, by specifically selecting duplex material, specifically destroying single-stranded material, or utilizing some combination of these methods. For example, hybridization reaction mixtures can be subjected to high-stringency conditions and/or single strand-specific nucleases; or duplexes can be purified by affinity techniques specific for double-stranded, as opposed to single-stranded, nucleic acids. In a preferred embodiment of the invention, duplexes are detected by release of label from a probe under conditions in which label is released only when the probe is in a duplex. Another embodiment requires the separation of the label and quenchers when hybridized to the target.

Detectable labels or tags suitable for use with nucleic acid probes are well-known to those of skill in the art and include, but are not limited to, radioactive isotopes, chromophores, fluorophores, chemiluminescent and electrochemiluminescent agents, magnetic labels, microspheres, colloidal metal (Taton et al, *Science* 289:1757-1760 (2000)), immunologic labels, ligands and enzymatic labels. Suitable labels also include mass labels and those used in deconvolution of combinatorial chemistry libraries, for example, tags that can be recognized by high performance liquid chromatography (HPLC), gas chromatography, mass spectrometry, optical imaging fibers, surface plasmon resonance, correlation spectroscopy, nanotechnology (Guetence et al, *J. Chromatogr. B. Biomed. Sci. Appl.* 739:139-150 (2000)) and the like.

Methods for labeling of oligonucleotides are well-known to those of skill in the art and include, for example, chemical and enzymatic methods. By way of example, methods for incorporation of reactive chemical groups into oligonucleotides, at specific sites, are well-known to those of skill in the art. Oligonucleotides containing a reactive chemical group, located at a specific site, can be combined with a label attached to a complementary reactive group (e.g., an oligonucleotide containing a nucleophilic reactive group can be reacted with a label attached to an electrophilic reactive group) to couple a label to a probe by chemical techniques. Exemplary labels and methods for attachment of a label to an oligonucleotide are described, for example, in U.S. Pat. No. 5,824,796; U.S. Pat. No. 5,210,015; Kessler (ed.), *Nonradioactive Labeling and Detection of Biomolecules*, Springer-Verlag, Berlin, 1992; Kricka (ed.) *Nonisotopic DNA Probe Techniques*, Academic Press, San Diego, 1992; Howard (ed.) *Methods in Nonradioactive Detection*, Appleton & Lange, Norwalk, 1993. Non-specific chemical labeling of an oligonucleotide can be achieved by combining the oligonucleotide with a chemical that reacts, for example, with a particular functional group of a nucleotide base, and simultaneously or subsequently reacting the oligonucleotide with a label. See, for example, Draper et al. (1980) *Biochemistry* 19:1774-1781. Enzymatic incorporation of label into an oligonucleotide can be achieved by conducting enzymatic modification or polymerization of an oligonucleotide using labeled precursors, or by enzymatically adding label to an already-existing oligonucleotide. See, for example, U.S. Pat. No. 5,449,767. Examples of modifying enzymes include, but are not limited to, DNA polymerases, reverse transcriptases, RNA polymerases, etc. Examples of enzymes which are able to add label to an already-existing oligonucleotide include, but are not limited to, kinases, terminal transferases, ligases, glycosylases, etc.

If an oligonucleotide is capable of acting as a primer, the degree of hybridization of the oligonucleotide can also be determined by measuring the levels of the extension product of the primer. In the case, either the primer can be labeled, or one or more of the precursors for polymerization (normally nucleoside triphosphates) can be labeled. Extension product can be detected, for example, by size (e.g., gel electrophoresis), affinity methods, or any other technique known to those of skill in the art.

Primer extension ("minisequencing", "genetic bit analysis") assays are commonly used for SNP typing and have the potential to be used in other genotyping and mutation screening applications (Pastinen T. et al., *Genome Res.*, 10:1031-42 (2000)). In certain embodiments modified bases and minor groove binders improve primer extension assays in several ways. The added duplex stability provided by MGB, or 5-substituted pyrimidine or 3-substituted pyrazolo[3,4-d]pyrimidine enables extensions to be performed at elevated temperatures. This is advantageous because problematic secondary structures in target molecules are eliminated at elevated temperatures. Also, hybridization of target to primer is faster at higher temperature. Thermostable polymerases such as Taq polymerase and Bst DNA polymerase may be used in such reactions.

Furthermore, MGBs and modified bases improve the specificity of assays by eliminating one class of false positive signals. Primer sequences that form hairpin structures or homodimers are prone to template-independent extension (the 5' end of the primer functions as template), resulting in false positive signal. MGBs and modified bases on "templates" inhibit extension by DNA polymerases. Thus, MGBs on the 5' end, or modified bases on the 5' end or middle of a primer, can prevent extension (false positives) from primer hairpins or primer dimers. Finally, PPG can be used to eliminate non-canonical structures formed by G-rich oligonucleotides, enabling primer extension assays in such sequences.

Other assays in which the present modified oligonucleotides are particularly useful are described in co-pending application Ser. No. 09/054,832.

Still other amplification assays in which modified oligonucleotides are useful include the amplification assays based on the invasive cleavage of oligonucleotide probes by flap endonucleases (Lyamichev et al., *Nature Biotechnol.*, 17:292-296 (1999) and Olson, et al., High-Throughput Gene Expression Monitoring with the Invader® Assay, Poster, Society for Biomolecular Screening Conference, Vancouver, British Columbia, Canada, 2000); self-sustained sequence replication type assays (Mueller et al, *Histochem. Cell Biol.*, 108:431-437 (1997)) and the like. Surprisingly, non-natural bases can be substituted in both the invader and genomic probes of a cleavase-based assay. These modifications include but are not limited to pyrazolo[3,4-d]pyrimidines, 3-substituted pyrazolo[3,4-d]pyrimidines and 5-substituted pyrimidines. Non-natural backbones are also included such as monomers used in peptide nucleic acids, locked nucleic acids etc. Still further, the modified oligonucleotides can have attached minor groove binders, fluorophores, quenchers, and the like. One of skill in the art will appreciate that chimeras can also be used to allow optimal enzyme activity and performance.

In the present invention, marked improvements are unexpectedly shown in cleavase-based assays, when modified bases were substituted for normal bases in both the invader and genomic probes. Thus, the use of the modified bases such as hydoxypropynylPPA (HOPPPA), $(NH_2)_2$PPPAOH and 3-iododiaminoPPA allowed one to decrease the length of both the invader and genomic probes, yet provide improved assay performance. In another embodiment non-natural bases are also incorporated in the cassette probe.

In view of the above, the present invention provides in one aspect, a method for distinguishing polynucleotides with related sequences, the method comprising:

(a) contacting a modified oligonucleotide having a defined sequence comprising at least one 3-substituted pyrazolo[3,4-d]pyrimidine or 5-substituted pyrimidine in place of a purine or pyrimidine base with at least two polynucleotides, wherein one of the polynucleotides has a target sequence that is perfectly complementary to the modified oligonucleotide and at least one of the other polynucleotides has a target sequence with at least one base mismatch; and (b) determining the degree of hybridization between the modified oligonucleotide and each of the polynucleotides.

Preferably, at least one of the other polynucleotides has a target sequence with one or two base mismatches, more preferably only one base mismatch.

As noted above, a target sequence refers to a nucleotide sequence which comprises a site of hybridization for a probe or a primer. Target sequences can be found in any nucleic acid including, but not limited to, genomic DNA, cDNA, RNA and any amplified product thereof, and can comprise a wild-type gene sequence, a mutant gene sequence, a non-coding sequence, a regulatory sequence, etc. A target sequence will generally be less than 100 nucleotides, preferably less than 50 nucleotides, and most preferably, less than 21 nucleotides in length.

The modified oligonucleotides used in this aspect of the invention are essentially modified probes and the polynucleotides can be distinguished by determining which polynucleotides hybridizes to the modified probe. The modified probes can be labeled with any detectable label, or the probe can have the capacity to become labeled either before or after hybridization, such as by containing a reactive group capable of association with a label or by being capable of hybridizing to a secondary labeled probe, either before or after hybridization to the target. Conditions for hybridization of nucleic acid probes are well-known to those of skill in the art. See, for example, Sambrook et al., supra; Ausubel et al., supra; Innis et al., supra; Hames et al. supra; and van Ness et al., supra.

Hybridization can be assayed (i.e., hybridized nucleic acids can be identified) by distinguishing hybridized probe from free probe by one of several methods that are well-known to those of skill in the art. These include, but are not limited to, attachment of target nucleic acid to a solid support, either directly or indirectly (by hybridization to a second, support-bound probe or interaction between surface-bound and probe-conjugated ligands) followed by direct or indirect hybridization with probe, and washing to remove unhybridized probe; determination of nuclease resistance; buoyant density determination; affinity methods specific for nucleic acid duplexes (e.g., hydroxyapatite chromatography); interactions between multiple probes hybridized to the same target nucleic acid; etc. See, for example, Falkow et al., U.S. Pat. No. 4,358,535; Urdea et al., U.S. Pat. Nos. 4,868,105 and 5,124,246; Freifelder, *Physical Biochemistry*, Second Edition, W. H. Freeman & Co., San Francisco, 1982; Sambrook, et al., supra; Ausubel et al., supra; Hames et al., supra; and other related references. The duplex-stabilizing capability of MGB-modified oligonucleotide conjugates makes hybridization possible under more stringent conditions, wherein potentially occluding secondary structure in the target nucleic acid can be minimized. Accordingly, such MGB-modified oligonucleotides are particularly preferred in this aspect of the invention.

In a related aspect, the present invention provides a method for detecting the presence of a target sequence in a polynucleotide, the method comprising:

(a) incubating a polynucleotide to be tested for the presence of the target sequence with a modified oligonucleotide having a sequence that is substantially complementary to the target sequence under hybridization conditions; and (b) identifying hybridized nucleic acids;

wherein the modified oligonucleotide comprises at least one 3-substituted pyrazolo[3,4-d]pyrimidine in place of a purine residue.

Preferably, the modified oligonucleotide is a labeled probe and has at least two 3-substituted pyrazolo[3,4-d]pyrimidine bases. In this group of embodiments, a labeled probe is hybridized to a target and/or an extension product of a target, and a change in the physical state of the label is effected as a consequence of hybridization. As used herein, a "probe" is a nucleic acid molecule that is capable of hybridizing to a target sequence in a second nucleic acid molecule. By way of example, one assay of this type, the hydrolyzable probe assay, takes advantage of the fact that many polymerizing enzymes, such as DNA polymerases, possess intrinsic 5'-3' exonucleolytic activities. Accordingly, if a probe is hybridized to a sequence that can serve as a template for polymerization (for instance, if a probe is hybridized to a region of DNA located between two amplification primers, during the course of an amplification reaction), a polymerizing enzyme that has initiated polymerization at an upstream amplification primer is capable of exonucleolytically digesting the probe. Any label attached to such a probe will be released, if the probe is hybridized to its target and if amplification is occurring across the region to which the probe is hybridized. Released label is separated from labeled probe and detected by methods well-known to those of skill in the art, depending on the nature of the label. For example, radioactively labeled fragments can be separated by thin-layer chromatography and detected by autoradiography; while fluorescently-labeled fragments can be detected by irradiation at the appropriate excitation wavelengths with observation at the appropriate emission wavelengths. See, e.g., U.S. Pat. No. 5,210,015.

In a variation of this technique, a probe contains both a fluorescent label and a quenching agent, which quenches the fluorescence emission of the fluorescent label. In this case, the fluorescent label is not detectable until its spatial relationship to the quenching agent has been altered, for example by exonucleolytic release of the fluorescent label from the probe. Thus, prior to hybridization to its target sequence, the dual fluorophore/quencher labeled probe does not emit fluorescence. Subsequent to hybridization of the fluorophore/quencher-labeled probe to its target, it becomes a substrate for the exonucleolytic activity of a polymerizing enzyme which has initiated polymerization at an upstream primer. Exonucleolytic degradation of the probe releases the fluorescent label from the probe, and hence from the vicinity of the quenching agent, allowing detection of a fluorescent signal upon irradiation at the appropriate excitation wavelengths. This method has the advantage that released label does not have to be separated from intact probe. Multiplex approaches utilize multiple probes, each of which is complementary to a different target sequence and carries a distinguishable label, allowing the assay of several target sequences simultaneously.

The use of MGB-modified oligonucleotide conjugates in this and related methods allows greater speed, sensitivity and discriminatory power to be applied to these assays. In particular, the enhanced ability of MGB-modified oligonucleotide conjugates to allow discrimination between a perfect hybrid and a hybrid containing a single-base mismatch will facilitate the use of hydrolyzable probe assays in the identification of single-nucleotide polymorphisms and the like. One of skill in the art will appreciate that compositions and methods, such as those of the invention, that are capable of discriminating single-nucleotide mismatches will also be capable of discriminating between sequences that have 2, 3, 4, 5, or even 6 or more mismatches with respect to one another.

In yet another related aspect, the present invention provides a method for primer extension, the method comprising incubating a polynucleotide containing a target sequence with one or more oligonucleotide primers complementary to the target sequence, in the presence of a polymerizing enzyme and nucleotide substrates under conditions favorable for polymerization; wherein at least one of the oligonucleotide primers contains a 3-substituted pyrazolo[3,4-d]pyrimidine or a 5-substituted pyrimidine base in place of a purine or pyrimidine base.

Amplification procedures are those in which many copies of a target nucleic acid sequence are generated, usually in an exponential fashion, by sequential polymerization and/or ligation reactions. In addition to the more traditional amplification reactions discussed below, the present invention is useful in amplifications involving three-way junctures (see, WO 99/37085), signal amplification (see Capaldi, et al., *Nuc. Acids Res.*, 28:E21 (2000)), T7 polymerases, reverse transcriptase, RNase H, RT-PCR, Rolling Circles, cleavase and the like.

Many amplification reactions, such as PCR, utilize reiterative primer-dependent polymerization reactions. A primer is a nucleic acid that is capable of hybridizing to a second, template nucleic acid and that, once hybridized, is capable of being extended by a polymerizing enzyme (in the presence of nucleotide substrates), using the second nucleic acid as a template. Polymerizing enzymes include, but are not limited to, DNA and RNA polymerases and reverse transcriptases, etc. Conditions favorable for polymerization by different polymerizing enzymes are well-known to those of skill in the art. See, for example, Sambrook et al., supra; Ausubel, et al., supra; Innis et al., supra. Generally, in order to be extendible by a polymerizing enzyme, a primer must have an unblocked 3'-end, preferably a free 3' hydroxyl group. The product of an amplification reaction is an extended primer, wherein the primer has been extended by a polymerizing enzyme.

Thus, in one embodiment of the invention, the methods and compositions disclosed and claimed herein are useful in improved amplification reactions such as PCR. See, e.g., U.S. Pat. Nos. 4,683,202; 4,683,195 and 4,800,159; Mullis and Faloona, supra; and Saiki et al., supra. The polymerization step of PCR is most often catalyzed by a thermostable polymerizing enzyme, such as a DNA polymerase isolated from a thermophilic bacterium, because of the elevated temperatures required for the denaturation step of PCR. As discussed supra, one of the problems heretofore associated with the practice of PCR is the requirement for relatively long oligonucleotide primers, having sufficient hybrid stability to serve as primers at the elevated temperatures under which PCR is conducted. Modified oligonucleotides and especially MGB-modified oligonucleotide conjugates are useful as primers in amplification reactions such as PCR, as the modified bases and MGBs increase hybrid stability, thereby significantly extending the lower limit of useful primer length. In addition, MGB-modified oligonucleotide conjugates are useful in specialized PCR protocols wherein reduced primer length is desirable. These include, but are not limited to, differential display, in which optimal primer length is below 10 nucleotides, random amplification of polymorphism in DNA (RAPD) techniques, and amplification length polymorphism analyses. Liang et al, supra; Williams et al., supra.

The modified oligonucleotides of the present invention are applicable to any type of assay or procedure in which PCR or a related amplification technique is used, including, but not limited to, hydrolyzable probe assays, priming with allele-specific oligonucleotides (ASOs), fragment length polymorphism analysis, single nucleotide polymorphism (SNP) analysis and microsatellite analysis, for example. These and other techniques are useful in gene mapping, in the identification and screening of disease-related genes, and in pharmacogenetics, to name just a few applications.

In still another related aspect, the present invention provides a method for determining the nucleotide sequence of a polynucleotide, the method comprising:

(a) incubating the polynucleotide with a modified oligonucleotide array under hybridization conditions; and (b) determining to which of the modified oligonucleotides in the array the polynucleotide hybridizes;

wherein the modified oligonucleotides comprise at least one 3-substituted pyrazolo[3,4-d]pyrimidine in place of a purine base.

In these procedures, an ordered array comprising a plurality of modified oligonucleotides of different known sequences is used as a platform for hybridization to one or more test polynucleotides, nucleic acids or nucleic acid populations. Determination of the oligonucleotides which are hybridized and alignment of their known sequences allows reconstruction of the sequence of the test polynucleotide. See, for example, U.S. Pat. Nos. 5,492,806; 5,525,464; 5,556,752; and PCT Publications WO 92/10588 and WO 96/17957. Materials for construction of arrays include, but are not limited to, nitrocellulose, glass, silicon wafers, optical fibers and other materials suitable for construction of arrays such as are known to those of skill in the art.

A major problem with current array-based sequencing and analysis methods is that the different oligonucleotides in an array will each have a different $T_m$. Hence, it is difficult to determine the stringency conditions that will provide maximum sensitivity, while retaining the ability to distinguish single-base mismatches. This is a particularly important consideration for most, if not all, applications of array technology. Use of modified oligonucleotides and/or MGB-modified oligonucleotide conjugates in array-based sequencing and analysis techniques provides a solution to this problem. Surprisingly, conjugation of a MGB to a modified oligonucleotide makes its $T_m$ relatively independent of base composition. Thus, for a population of modified oligonucleotides and MGB-modified oligonucleotide conjugates of a given length, the $T_m$ for a perfect hybrid falls within a relatively narrow temperature range regardless of sequence. At the same time, the $T_m$ for a single nucleotide mismatch is well below the $T_m$ of the perfect match. Thus, arrays designed such that all modified oligonucleotides are the same length and are optionally present as their MGB conjugates exhibit minimal variation in $T_m$ among the different oligonucleotides in the array, enabling more uniform hybridization conditions for the entire array. A further advantage to the use of modified oligonucleotides and MGB-modified oligonucleotide conjugates in these techniques is that it provides greater sensitivity, by allowing the use of shorter oligonucleotides, at higher temperatures (and hence higher stringency), while retaining single-nucleotide resolution.

An additional application of the present invention to array technology is in the examination of patterns of gene expression in a particular cell or tissue (see, generally, Eisen, et al., METHODS IN ENZYMOLOGY, 303:179-205 (1999)). In this case, modified oligonucleotides or polynucleotides corresponding to different genes are arrayed on a surface, and a nucleic acid sample from a particular cell or tissue type, for example, is incubated with the array under hybridization conditions. Detection of the sites on the array at which hybridization occurs allows one to determine which modified oligonucleotides have hybridized, and hence which genes are active in the particular cell or tissue from which the sample was derived.

Array methods can also be used for identification of mutations or polymorphisms, where wild-type and mutant sequences are placed in an ordered array on a surface (see, Hacia, et al., *J. Mol. Genet.*, 36:730-736 (1999)). Hybridization of a polynucleotide sample to the array under stringent conditions, and determination of which oligonucleotides in the array hybridize to the polynucleotide, allows determination of whether the polynucleotide possesses the wild-type or the mutant sequence. The increased discriminatory abilities of MGB-oligonucleotide conjugates are especially useful in this application of array technology.

Accordingly, the present invention provides a method for identifying a mutation in a target sequence of a gene of interest, the method comprising:

(a) incubating a polynucleotide comprising the target sequence with an array of oligonucleotides of different sequences, wherein the different sequences include the wild-type target sequence and different mutant target sequences, under hybridization conditions; and (b) determining which of the oligonucleotides in the array become hybridized to the polynucleotide;

wherein one or more purine residues in a plurality of the oligonucleotides are replaced with a 3-substituted pyrazolo [3,4-d]pyrimidine.

In yet another related aspect, the present invention provides a method determining the nucleotide sequence of a target sequence in a polynucleotide, the method comprising:

(a) contacting a polynucleotide comprising the target sequence with at least two oligonucleotides of known sequence wherein one or more purine residues of the oligonucleotides are replaced by a 3-substituted pyrazolo[3,4-d] pyrimidine, and wherein one of the at least two oligonucleotides has a sequence that is perfectly complementary to the target sequence and at least one other of the oligonucleotides has a related target sequence and incubating each of the oligonucleotides with the polynucleotide under hybridization conditions; and (b) determining the degree of hybridization between each of the oligonucleotides and the polynucleotide.

In one embodiment, a collection of all possible n-mer oligonucleotides (where n is an integer less than about 10) are used in a hydrolyzable probe assay to determine a nucleotide sequence. Each oligonucleotide is uniquely labeled (and preferably modified) and analysis of released label indicates which of the oligonucleotides has hybridized to the target sequence. Alignment of the sequences of the oligonucleotides which have hybridized provides the nucleotide sequence.

Modified oligonucleotides, and more preferably modified oligonucleotide-MGB conjugates are also useful in primer-dependent methods of DNA sequencing, such as the chain-termination method and its derivatives, originally described by Sanger et al., supra. Use of MGB-modified oligonucleotide conjugates in chain-termination sequencing allows the use of shorter primers at higher stringency, and enables a greater degree of mismatch discrimination during sequencing. Examples include, but are not limited to, a search for genes-sharing a short region of homology (on the order of a few amino acids) and sequencing in a region in which very little existing sequence information is available. MGB-oligonucleotide conjugates are useful in such short primer sequencing techniques.

In still another embodiment, the present invention provides a method for examining gene expression in a cell, the method comprising:

(a) incubating a population of polynucleotides representative of the genes expressed in the cell with an oligonucleotide array comprising a plurality of modified oligonucleotides of different sequences under hybridization conditions, and (b) determining which of the modified oligonucleotides in the array become hybridized to polynucleotides;

wherein said modified oligonucleotides comprise at least one 3-substituted pyrazolo[3,4-d]pyrimidine in place of a purine.

In one group of embodiments, the method is carried out with a plurality of expressed genes from multiple cell-types or tissues. The genes are preferably labeled with different detection labels, then hybridized to an array at the same time and monitored via the label to determine each gene's expression pattern.

In addition to the assays and diagnostic methods described above, the modified oligonucleotides and modified bases described herein will have utility in antisense technologies. Antisense oligonucleotides are known to selectively inhibit gene expression and provide a genetic approach for disease treatment and prevention (Smith et al, *Int. J. Oncol.*, 17:841-850 (2000)). Other modified oligonucleotides have been used to improve the performance of antisense oligonucleotides (Zhang et al, *Nat. Biotechnol.*, 18:862-867 (2000); Flanagan et al, *Nat. Biotechnol.*, 14:1139-1145 (1996)). Accordingly, another embodiment of the present invention is the use of the 5-substituted pyrimidines, unsubstituted pyrazolo[3,4-d]pyrimidines and 3-substituted pyrazolo[3,4-d]pyrimidine as monomers, either alone or in any combination, in the synthesis of antisense oligomers. In another embodiment the modified bases described herein can be used as monomers in an oligonucleotide to decrease enzymatic degradation of the antisense oligomers.

New Modified Bases

In another aspect, the present invention provides a number of new modified bases. These bases have the general formula:

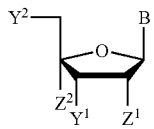

wherein $Z^1$ is a member selected from the group consisting of H, F and $OR^a$ wherein $R^a$ is a member selected from the group consisting of H, $(C_1-C_8)$alkyl and a hydroxy protecting group; $Z^2$ is a member selected from the group of H, $(C_1-C_8)$ alkyl, or is optionally combined with $Z^1$ to form a five- to seven-membered ring, having from one to three heteroatoms selected from the group consisting of O, S and N; $Y^1$ is a member selected from the group consisting of OH, a protected hydroxy group and $O-P^1$, wherein $P^1$ is a phosphoramidite or H-phosphonate group; $Y^2$ is a member selected from the group consisting of OH, a protected hydroxy group and $O-P^2$, wherein $P^2$ is a phosphoramidite, H-phosphonate, monophosphate, diphosphate or triphosphate; and B is a modified nucleotide selected from the group consisting of:

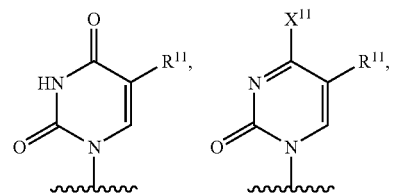

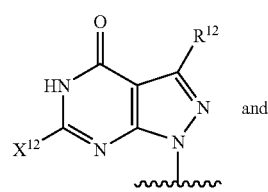

and

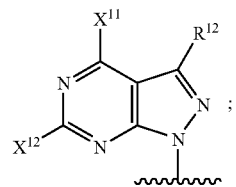

wherein $X^{11}$ and $X^{12}$ are each independently selected from the group consisting of H, $NH_2$ and a protected amino group; each $R^{11}$ is independently selected from the group consisting of protected or unprotected forms of 3-hydroxyprop-1-ynyl, 3-aminoprop-1-ynyl, 3-methoxyprop-1-ynyl, 4-hydroxy-1-butynyl, 4-amino-1-butynyl and 3-(hydroxymethyl)-4-hydroxy-1-butynyl; and each $R^{12}$ is independently selected from the group consisting of heterocyclyl$(C_1-C_{12})$alkyl, heterocyclyl$(C_2-C_{12})$alkenyl, heterocyclyl$(C_2-C_{12})$alkynyl, heterocyclyl, 3-hydroxyprop-1-ynyl, 3-aminoprop-1-ynyl, 3-methoxyprop-1-ynyl, 4-hydroxy-1-butynyl, 4-amino-1-butynyl and 3-(hydroxymethyl)-4-hydroxy-1-butynyl, with the proviso that $R^{12}$ is other than 2-pyridylethynyl.

In one group of embodiments, B is

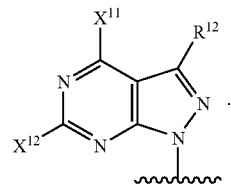

Preferably, $X^{11}$ is $NH_2$ and $X^{12}$ is H. More preferably, $X^{11}$ is $NH_2$, $X^{12}$ is H, $Y^1$ is O—$P^1$, $Y^2$ is a protected hydroxy, $Z^1$ is H, and $R^{12}$ is selected from 3-hydroxyprop-1-ynyl, 3-aminoprop-1-ynyl, 4-hydroxy-1-butynyl, 4-amino-1-butynyl, 3-(hydroxymethyl)-4-hydroxy-1-butynyl, 3-methoxyprop-1-ynyl, 2-furanyl, 3-furanyl, 2-thienyl, 3-thienyl, 2-pyrrolyl, 3-pyrrolyl, 1,3-isoxazol-4-yl, 1,3-isoxazol-5-yl, 1,3-isoxazol-2-yl, 2-imidazolyl, 4-imidazolyl, 2-pyridyl, 3-pyridyl and 4-pyridyl. In particularly preferred embodiments, $Y^1$ is —O—[(2-cyanoethyl) N,N-diisopropylphosphoramidite] and $Y^2$ is —O—(4,4'-dimethoxytrityl).

In another group of embodiments, B is

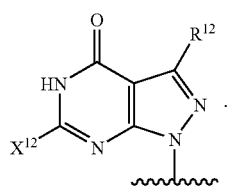

Preferably, $X^{12}$ is $NH_2$ or H. More preferably, $X^{12}$ is $NH_2$ or H, $Y^1$ is O—$P^1$, $Y^2$ is a protected hydroxy, $Z^1$ is H, and $R^{12}$ is selected from 3-hydroxyprop-1-ynyl, 3-aminoprop-1-ynyl, 3-(hydroxymethyl)-4-hydroxy-1-butynyl, 3-methoxyprop-1-ynyl, 2-furanyl, 3-furanyl, 2-thienyl, 3-thienyl, 2-pyrrolyl, 3-pyrrolyl, 1,3-isoxazol-4-yl, 1,3-isoxazol-5-yl, 1,3-isoxazol-2-yl, 2-imidazolyl, 4-imidazolyl, 2-pyridyl, 3-pyridyl and 4-pyridyl. In particularly preferred embodiments, $Y^1$ is —O-[(2-cyanoethyl)N,N-diisopropylphosphoramidite] and $Y^2$ is —O-(4,4'-dimethoxytrityl).

In still other preferred embodiments, the modified oligonucleotides of the invention have at least one base of formula III (including those in which the acetyl protecting groups are removed, and including other protected forms and activated forms thereof).

III

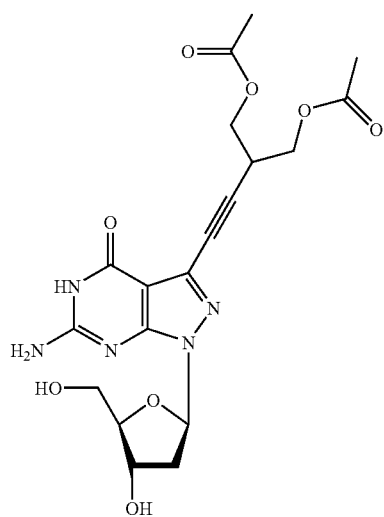

Preparation of compounds of formula III (including compounds wherein the 6-amino group is protected and the hydroxy groups of the sugar are either protected or activated as a phosphoramidite) are provided in Reaction Scheme 6, above.

In the most preferred embodiments of the invention, the modified bases are selected from formulae IVa, IVb or IVc.

IVa

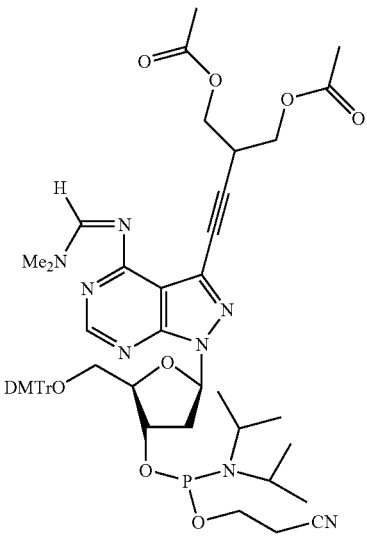

IVb

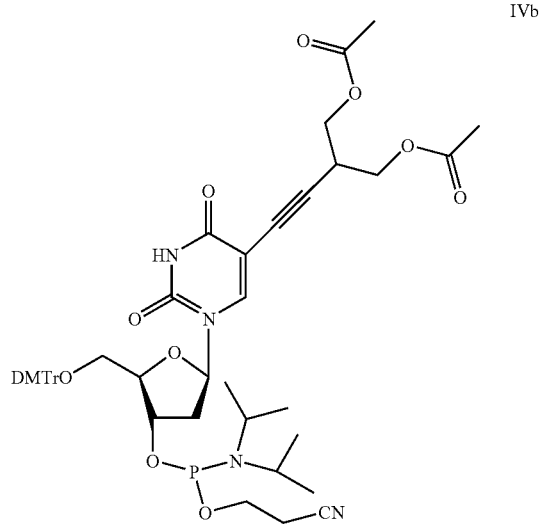

IVc

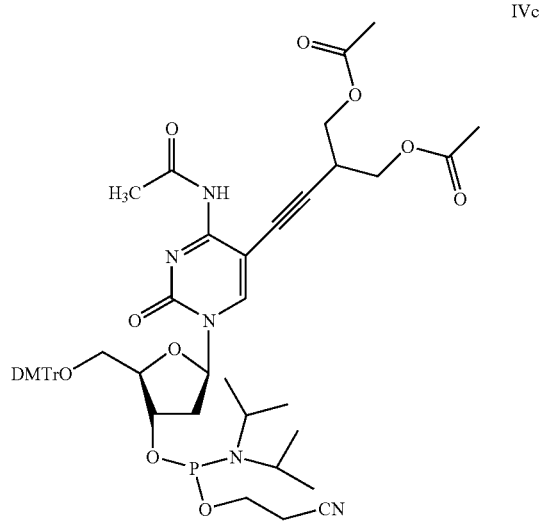

These compounds are particularly well-suited for use in automatic oligonucleotide synthesizers, and in preparing certain modified oligonucleotides described herein.

Other modified bases that are useful in the present invention include those represented by formulae Va and Vb:

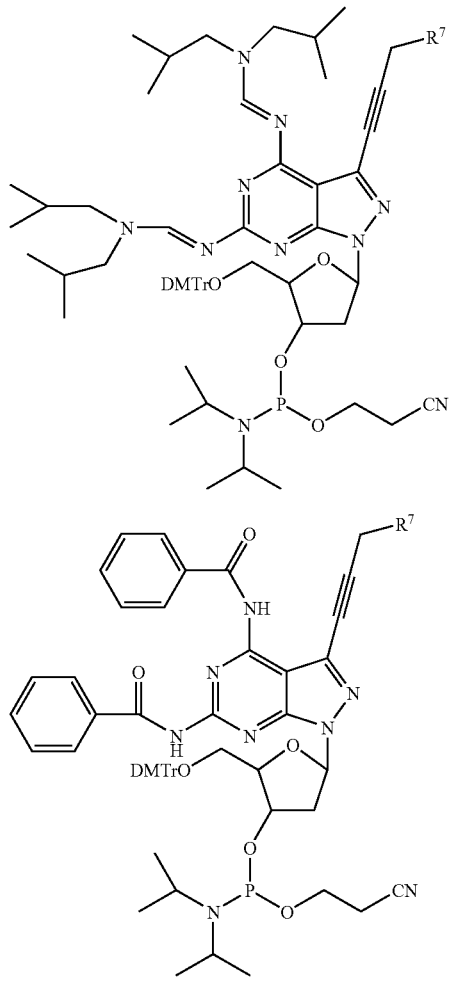

wherein $R^7$ is selected from OH, SH or $NH_2$. These compounds can be synthesized by methods described herein.

In another group of embodiments, B is

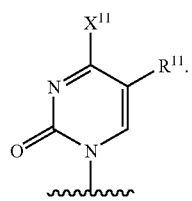

Preferably, $X^{11}$ is $NH_2$. More preferably, $X^{11}$ is $NH_2$, $Y^1$ is $O-P^1$, $Y^2$ is a protected hydroxy, $Z^1$ is H, and $R^{11}$ is selected from 3-hydroxyprop-1-ynyl, 3-aminoprop-1-ynyl, 4-hydroxy-1-butynyl, 4-amino-1-butynyl, 3-(hydroxymethyl)-4-hydroxy-1-butynyl, and 3-methoxyprop-1-ynyl. In particularly preferred embodiments, $Y^1$ is —O-[(2-cyanoethyl)N,N-diisopropylphosphoramidite] and $Y^2$ is —O-(4,4'-dimethoxytrityl).

In another group of embodiments, B is

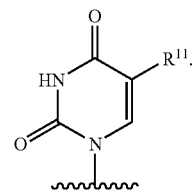

Preferably, $Y^1$ is $O-P^1$, $Y^2$ is a protected hydroxy, $Z^1$ is H, and $R^{11}$ is selected from 3-hydroxyprop-1-ynyl, 3-aminoprop-1-ynyl, 4-hydroxy-1-butynyl, 4-amino-1-butynyl, 3-(hydroxymethyl)-4-hydroxy-1-butynyl, and 3-methoxyprop-1-ynyl. In particularly preferred embodiments, $Y^1$ is —O-[(2-cyanoethyl)N,N-diisopropylphosphoramidite] and $Y^2$ is —O-(4,4'-dimethoxytrityl).

In a related aspect, the present invention provides modified oligonucleotides having the formula:

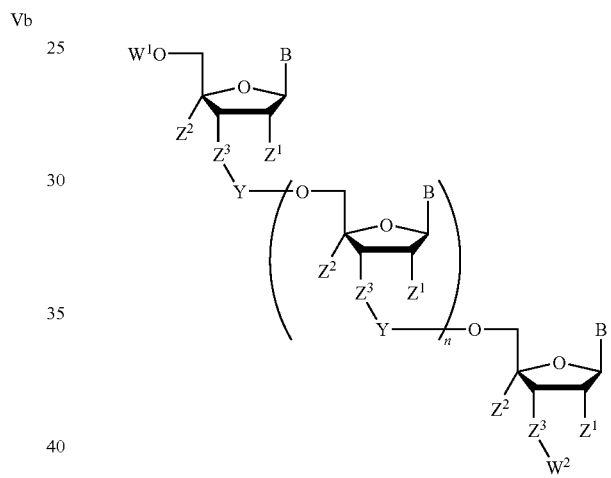

wherein each $Z^1$ is independently selected from H, F and $OR^a$ wherein $R^a$ is a member selected from H, $(C_1-C_8)$alkyl and a hydroxy protecting group; each $Z^2$ is H or $(C_1-C_8)$alkyl, or is optionally combined with $Z^1$ to form a five- to seven-membered ring; each $Z^3$ is selected from O, S or NM; each Y is independently selected from P(O)OH, P(S)OH and P(O)$CH_3$; the subscript n is an integer of from 1 to 98; $W^1$ and $W^2$ are each independently selected from H, a monophosphate, a diphosphate, a triphosphate and a minor groove binder-linking group moiety having an optionally attached reporter group or quencher; and each B is independently selected from the group consisting of adenine, guanine, cytosine, uridine and modified bases of the formula:

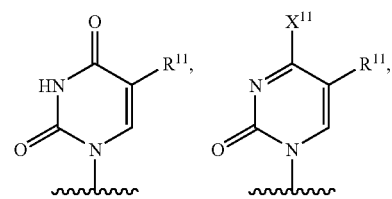

-continued

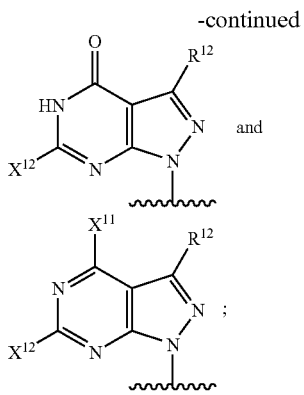

and wherein $X^{11}$ and $X^{12}$ are each independently selected from H, $NH_2$ and a protected amino group; each $R^{11}$ is independently selected from protected or unprotected forms of 3-hydroxyprop-1-ynyl, 3-aminoprop-1-ynyl, 3-methoxyprop-1-ynyl, 4-hydroxy-1-butynyl, 4-amino-1-butynyl, and 3-(hydroxymethyl)-4-hydroxy-1-butynyl; and each $R^{12}$ is independently selected from the group consisting of protected or unprotected forms of 3-hydroxyprop-1-ynyl, 3-aminoprop-1-ynyl, 3-methoxyprop-1-ynyl, 4-hydroxy-1-butynyl, 4-amino-1-butynyl, 3-(hydroxymethyl)-4-hydroxy-1-butynyl, heterocyclyl($C_1$-$C_{12}$)alkyl, heterocyclyl($C_2$-$C_{12}$)alkenyl, heterocyclyl($C_2$-$C_{12}$)alkynyl and heterocyclyl, with the provsio that $R^{12}$ is other than 2-pyridylethynyl; and with the further proviso that at least one of the Bs is selected from the modified bases, and optionally, one or more of the Bs has an attached minor groove binder-linking group moiety, reporter group or a combination thereof.

Particularly preferred modified bases are those that have been described above.

EXAMPLES

In the hydrolyzable probe assay, a labeled probe is added to a PCR reaction. The probe is complementary to a region between the two PCR primers and is labeled with two fluorophores, one of which quenches the fluorescence of the other. The probe is designed to hybridize to its complementary target sequence on ogle of the PCR product strands at or above the strand extension temperature typically used in PCR (55-75° C.). The polymerizing enzymes normally used in PCR (Taq polymerase in particular) possess an intrinsic 5'-exonuclease activity. During synthesis of new strands in the extension stage of the PCR reaction, this 5'-exonuclease activity will act on complementary strands bound to the template. If a probe, labeled as described above, is bound to the template, the 5'-exonuclease activity associated with the polymerizing enzyme will liberate the bound fluorophore. Once liberated, its fluorescence will no longer be quenched, and a fluorescent signal will be obtained. See, for example, U.S. Pat. No. 5,210,015; Livak et al. (1995) *PCR Meth. App.* 4:357-362; and Heid et al. (1996) *Genome Res.* 6:986-994.

Thin-layer chromatography was run on silica gel 60 F-254 (EM Reagents) aluminum-backed plates. $^1$H NMR were obtained at 300 MHz on a VARIAN VXR-300 spectrometer. Two-dimensional (Cosy) and NOE experiments assisted in the assignment of proton resonances. Elemental analyses were performed by Quantitative Technologies Inc. (Boundbrook, N.J.).

Example 1

This example illustrates the synthesis of 5-(Prop-2-ynyl-4-methylbenzoate)-5'-O-(4,4'-dimethoxytriphenylmethyl)-2'-deoxyuridine 3'-[(2-cyanoethyl)N,N-diisopropylphosphoramidite] (3).

5-(Prop-2-ynyl-4-methylbenzoate)-2'-deoxyuridine (1)

To a mixture of 5-iodo-2'-deoxyuridine (5.0 g, 14.12 mmol), CuI (270 mg, 1.42 mmol), Pd(PPh$_3$)$_4$ (0.82 g, 0.714 mmol), and triethylamine (2.4 mL) in 30 mL of anhydrous DMF was added prop-2-ynyl 4-methylbenzoate (6.10 g, 35.06 mmol). The mixture was stirred under argon for 4 h. and then evaporated to dryness. The residue was triturated in methanol and the excess prop-2-ynyl 4-methylbenzoate that precipitated was filtered away. The filtrate was evaporated and the residue was purified by silica gel chromatography eluting with 10% methanol in ethyl acetate. The pure product fractions were evaporated to dryness and the residue was precipitated from ethyl acetate-ether: 3.14 g (56%) yield; TLC (10% methanol in ethyl acetate), $R_f$=0.50; $^1$H NMR (DMSO-d$_6$) δ 11.68 (1H, s, uracil N—H), 8.29 (1H, s, 6-H), 7.89 and 7.35 (4H, 2×d, J=8.2 Hz, toluoyl Hs), 6.10 (1H, t, J=6.4 Hz, 1'-H), 5.24 (1H, d, J=4.4 Hz, 3'-OH), 5.15 (2H, s, alkynyl-CH$_2$), 5.12 (1H, t, J=5.2 Hz, 5'-OH), 4.24 (1H, m, 3'-H), 3.79 (1H, q, 4'-H), 3.59 (2H, m, 5'-Hs), 2.39 (3H, s, toluoyl-CH$_3$), 2.13 (2H, m, 2'-H).

5-(Prop-2-ynyl-4-methylbenzoate)-5'-O-(4,4'-dimethoxytriphenylmethyl)-2'-deoxyuridine (2)

To a solution of 1 (3.0 g, 7.50 mmol) in 45 mL of anhydrous pyridine was added dimethoxytrityl chloride (3.0 g). The resulting solution was stirred for 4 h. at room temperature and then poured into 400 mL of 5% sodium bicarbonate solution. The mixture was extracted with ethyl acetate (2×300 mL) and the extract was dried over sodium sulfate, filtered and evaporated. The residue was purified by silica gel chromatography eluting with 5% methanol in the ethyl acetate. The pure product fractions were pooled and evaporated affording 2 as a foam: 4.16 g (79%) yield.

5-(Prop-2-ynyl-4-methylbenzoate)-5'-O-(4,4'-dimethoxytriphenylmethyl)-2'-deoxyuridine 3'-[(2-cyanoethyl)N,N-diisopropylphosphoramidite] (3)

To a solution of 2 (4.0 g, 5.70 mmol) in 130 mL of anhydrous methylene chloride, containing 3.0 mL of N,N-diisopropylethylamine was added chloro(2-cyanoethoxy)(N,N-diisopropylamino)phosphine (2.22 mL) under argon. The solution was stirred for 30 min at room temperature and then treated with 3.0 mL of methanol. The solution was diluted with 300 mL of ethyl acetate and washed with 300 mL of 5% sodium bicarbonate solution. The aqueous phase was extracted with 300 mL of ethyl acetate and the combined organic phases were dried over sodium sulfate, filtered and evaporated. The residue was purified by silica gel chromatography eluting with a gradient of 30 to 0% hexane in ethyl acetate (2% triethylamine). The pure fractions were pooled and evaporated and the residue was precipitated from ethyl acetate-hexanes: 3.35 g (65%) yield; TLC (20% hexane in ethyl acetate), R$_f$=0.82 and 0.71 (diasteromers); $^{31}$P NMR (DMSO-d$_6$) δ 147.82 and 147.45.

Example 2

Phase 1 Preparation of (2R,5R)-5-(4-amino-3-io-dopyrazolo[3,4-d]pyrimidinyl)-2-(hydroxymethyl) oxolan-3-ol (9)

3-Iodo-1,5-dihydropyrazolo[3,4-d]pyrimidin-4-one (4)

The synthesis of this compound was previously reported by Taylor et. al (*Tetrahedron*, 48(37):8089-8100 (1992)) using a N-iodosuccinimide. Our synthesis, employing iodine monochloride as the iodinating agent is described below.

To a 1.0 L solution of 1.2 M sodium acetate was added 4-hydroxypyrazolo[3,4-d]pyrimidine (25 g, 184 mmol) followed by iodine monochloride (46 g, 284 mmol). The mixture was stirred in a sealed container for 4 h. at 110° C. The completed reaction was cooled to room temperature and treated with a solution of 30 g of sodium metabisulfite in 200 mL of water. The white precipitate that formed was filtered and rinsed with cold water. The solid was then dissolved in 200 mL of 3.2 M potassium hydroxide solution. Hydrazine monohydrate (5 mL) was added and the solution was stirred for 15 min. The solution was then acidified to ca. pH 7 by addition of 50 mL of concentrated HCl followed by a fine pH adjustment with acetic acid. The solid that formed was filtered, rinsed with cold water and dried: 55.1 g (114% yield). Note—it is difficult to remove residual water by drying the solid under vacuum. The residual water will be removed by a pyridine evaporation process in the next step.

3-Iodo-1,5-dihydropyrazolo[3,4-d]pyrimidin-4-thione (5)

Compound 4 (21.5 g, 82.1 mmol) was suspended in 150 mL of anhydrous pyridine and the mixture was evaporated to dryness. The solid was re-suspended in 170 mL of dry pyridine (under argon) and P$_2$S$_5$ (26.8 g) was added. The mixture was stirred for 10 min at 65° C. and then for 2-6 hours at 95° C. The resulting solution was cooled to room temperature and degassed by bubbling a stream of argon into the solution (sulfide gas is passed into a trap containing sodium hydroxide solution). The reaction solution was then reduced in volume until a thick syrup formed. Excess P$_2$S$_5$ was decomposed by addition of 1 mL aliquots of water, until the vigorous reaction ceased, followed by addition of 500 mL of water and 10 mL of acetic acid. The mixture was warmed to 70° C. for 1 h to expedite expulsion of hydrogen sulfide gas and then diluted with 500 mL of water and cooled in an ice-bath. The solid was filtered, washed with water and dried: 19.8 g (87%) yield.

4-Ethylthio-3-iodopyrazolo[3,4-d]pyrimidine (6)

Compound 5 (43.5 g, 157 mmol) was stirred in potassium hydroxide solution (38.6 g KOH in 350 mL of water) for 30 min. The mixture was filtered and the filtrate was acidified to pH 10 by addition of acetic acid and then diluted with 350 mL of absolute ethanol. Iodoethane (10 mL) was added and the solution was stirred at room temperature. Additional 10 mL aliquots of iodoethane were added after 30 min. and 1.0 h. The reaction was complete after a total of 90 min. Other runs required further addition of iodoethane to complete the reaction. The reaction solution was diluted with 700 mL of water and 20 mL of acetic acid. The mixture was cooled in an ice-bath and the solid was filtered, rinsed with water and dried. This crude product was dissolved in 300 of DMF and stirred at 90° C. for 15 min. Insoluble material was filtered away and the filtrate was diluted with 1 L of water and cooled in an ice-water bath. The solid was filtered, rinsed with water and dried: 19 g (40%) yield.

[(2R,5-R)-5-(4-Ethylthio-3-iodopyrazolo[3,4-d]pyrimidinyl)-3-(4-methylphenylcarbonyloxy)oxolan-2-yl]methyl 4-methylbenzonate (7)

Compound 6 was converted to the corresponding potassium salt by reaction with 1 molar equivalent of potassium hydroxide in water. The resulting solution was evaporated to dryness and the residue was evaporated from dry acetonitrile. The potassium salt of 6 (29.0 g, 94.73 mmol) was dissolved in 80 mL of anhydrous DMF and then diluted with 830 mL of anhydrous acetonitrile. The chlorosugar derivative (48 g, 123 mmol) was added in one portion and the mixture was stirred for 3 h and then diluted with 1.5 L of 25% aqueous methanol. The mixture was allow to sit at 5° C. overnight. The crystals were filtered, rinsed with 25% aqueous methanol and dried: 32.2 g (52%) yield.

(2R,5R)-2-(hydroxymethyl)-5-(3-iodo-4-methylpyrazolo[3,4-d]pyrimidinyl)oxolan-3-ol (8)

To a suspension of 7 (10.97 g, 16.66 mmol) in 250 mL of methanol was added 22 mL of 1N sodium methoxide in methanol. The mixture was stirred at reflux and the reaction progress was monitored as soon as the mixture turned to a clear solution Note—formation of side products are observed if refluxing is continued after complete conversion to 5. The reaction was quenched by addition of 1.34 mL of acetic acid as soon as one component, corresponding to the desired product, is observed by TLC. The solution was evaporated and the residue was precipitated from methanol-ether-hexane. The solid was filtered and dried: 6.8 g (104%) yield crude product (contains sodium acetate).

(2R,5R)-5-(4-amino-3-iodopyrazolo[3,4-d]pyrimidinyl)-2-(hydroxymethyl)oxolan-3-ol (9)

Compound 8 (6.8 g, 17.35 mmol) was stirred in 200 mL of concentrated ammonium hydroxide (sealed container) at room temperature for 36 h. The mixture was evaporated and the residue was precipitated from acetonitrile-ether. The solid was filtered and dried: 5.36 g (82%) yield. NMR and spectral data on this compound is identical to.

Phase 2 Preparation of 3-{4-((1E)-1-aza-2-methyl-prop-1-enyl)-1-((2R,5R)-5-{[Bis(4-methoxyphenyl) phenylmethoxy]methyl}-4-{[bis(methylethyl)amino] (2-cyanoethoxy)phosphinooxy}oxolan-2-yl)pyrazolo [3,4-d]pyrimidin-3-yl]prop-2-ynyl 4-methoxybenzoate (13; R1=—OCOPhCH$_3$).

3-{1-{(2R,5R)-4-hydroxy-5-(hydroxymethyl)ox-olan-2-yl]-4-aminopyrazolo[3,4-d]pyrimidin-3-yl}prop-2-ynyl}4-methylbenzoate (10; R$^1$=— OCOPhCH$_3$)

To a mixture of 9 (2.40 g, 6.37 mmol), CuI (124 mg, 0.648 mmol), Pd(PPh$_3$)$_4$ (380 mg, 0.331 mmol), and triethylamine (1.32 mL) in 12 mL of anhydrous DMF was added prop-2-ynyl 4-methylbenzoate (1.87 g, 11.85 mmol). The mixture was stirred under argon for 12 h. and then evaporated to dryness. The residue was purified by silica gel chromatography eluting with 5% methanol in ethyl acetate. The pure product fractions were evaporated affording a foam: 2.29 g (85%) yield; TLC (10% methanol in ethyl acetate), $R_f$=0.43; $^1$H NMR (DMSO-$d_6$) δ 8.26 (1H, s, 6-H), 7.92 and 7.37 (4H, 2×d, J=8.5 Hz, toluoyl-Hs), 6.55 (1H, t, J=6.3 Hz, 1'-H), 5.29 (2H, s, alkynl-$CH_2$), 5.28 (1H, d, J=4.7 Hz, 3'-OH), 4.76 (1H, t, J=5.7 Hz, 5'-OH), 4.41 (1H, m, 3'-H), 3.81 (1H, m, 4'-H), 3.49 and 3.56 (2H, 2×m, 5'-Hs), 2.76 and 2.24 (2H, 2×m, 2'-Hs), 2.39 (3H, s, toluoyl-$CH_3$).

3-{4-((1E)-1-aza-2-methylprop-1-enyl)-1-((2R,5R)-4-hydroxy-5-(hydroxymethyl)oxolan-2-yl]pyrazolo[3,4-d]pyrimidin-3-yl}prop-2-ynyl 4-methylbenzoate (11; $R^1$=—OCOPhCH$_3$)

Compound 10 (1.76 g, 4.16 mmol) was stirred in a solution of 5.0 mL of N,N-dimethylacetamide, 1.9 mL of N,N-dimethylacetamide dimethyl acetal and 2.0 mL of anhydrous triethylamine for 15 h. at room temperature. The solvents were evaporated and the residue was evaporated twice from xylenes affording 11 as a foam. TLC (10% methanol in ethyl acetate), $R_f$=0.29; $^1$H NMR (DMSO-$d_6$) δ 8.51 (1H, s, 6-H), 7.90 and 7.37 (4H, 2×d, J=8.3 Hz, toluoyl protons), 7.28, 7.14 and 6.74 (13H, d and 2 m, J=7.1 Hz for the doublet), trityl protons), 6.63 (1H, m, 1'-H), 5.32 (1H, d, J=5.0 Hz, 3'-OH), 5.24 (2H, s, alkynl-$CH_2$), 4.56 (1H, m, 3'-H), 3.93 (1H, m, 4'-H), 3.68 (6H, s, methoxy Hs), 3.32 and 3.11 (6H, 2×s, N-methyls), 3.09-2.95 (2H, m, 5'-Hs), 2.81 and 2.32 (2H, 2×m, 2'-Hs), 2.40 (3H, s,=-Me), 2.19 (3H, s, toluoyl-Me).

3-{4-((1E)-1-aza-2-methylprop-1-enyl)-1-((2R,5R)-5-{[Bis(4-methoxyphenyl)phenylmethoxy]methyl}-4-hydroxyoxolan-2-yl)pyrazolo[3,4-d]primidin-3-yl]prop-2-ynyl 4-methylbenzoate (12; $R^1$=—OCOPhCH$_3$)

To a solution of 11 in 25 mL of anhydrous pyridine was added dimethoxytrityl chloride (1.67 g). The resulting solution was stirred for 4 h. at room temperature and then poured into 250 mL of 5% sodium bicarbonate solution. The mixture was extracted with ethyl acetate and the extract was dried over sodium sulfate, filtered and evaporated. The residue was purified by silica gel chromatography eluting with 5% methanol in the ethyl acetate. The pure product fractions were pooled and evaporated affording 12 as a foam: 2.06 g (62%) yield for the two-step process.

3-{4-((1E)-1-aza-2-methylprop-1-enyl)-1-((2R,5R)-5-{[Bis(4-methoxyphenyl)phenylmethoxy]methyl}-4-{[bis(methylethyl)amino](2-cyanoethoxy)phosphinooxy}oxolan-2-yl)pyrazolo[3,4-d]pyrimidin-3-yl]prop-2-ynyl 4-methoxybenzoate (13; $R^1$=—OCOPhCH$_3$) or, 1-[2-Deoxy-5-O-(4,4'-dimethoxytriphenylmethyl)-β-D-erythro-pentofuranosyl]-4-[(dimethylamino)prop-1-enyl]-3-(prop-2-ynyl-4-methylbenzoate) 1H-pyrazolo[3,4-d]pyrimidine 3'-[(2-cyanoethyl)N,N-diisopropylphosphoramidite] (13).

To a solution of 12 (2.03 g, 2.56 mmol) in 60 mL of anhydrous methylene chloride, containing 1.33 mL of N,N-diisopropylethylamine was added chloro(2-cyanoethoxy)(N,N-diisopropylamino)phosphine (1.0 mL) under argon. The solution was stirred for 1.0 h at room temperature and then treated with 2.0 mL of methanol. The solution was diluted with 250 mL of ethyl acetate and washed with 200 mL of 5% sodium bicarbonate solution. The organic phase was dried over sodium sulfate, filtered and evaporated. The residue was purified by silica gel chromatography eluting with 2% triethylamine in ethyl acetate. The pure fractions were pooled and evaporated. The phosphoramidite (13) was precipitated from ether-hexanes: 1.82 g (71%) yield; TLC (5% methanol in ethyl acetate), $R_f$=0.32; $^{31}$P NMR (DMSO-$d_6$) δ 147.90 and 147.22.

Example 3

This example illustrates the preparation of N-{3-[1-((2R,5R)-5{[bis(4-methoxyphenyl)phenylmethoxy]methyl}-4-{[bis(methylethyl)amino](2-cyanoethoxy)phosphinooxy}oxolan-2-yl)-6-amino-4-oxo(5-hydropyrazolo[3,4-d]pyrimidin-3-yl)]propyl}-2,2,2-trifluoroacetamide (22).

3-Iodo-4-methoxypyrazolo[3,4-d]pyrimidine-6-ylamine (14)

4-Methoxy-pyrazolo[3,4-d]pyrimidin-6-ylamine (6.75 g, 40.87 mmol) was suspended in an aqueous solution containing sodium acetate (6.0 g, 44.09 mmol) and iodine monochloride (9.12 g, 56.17 mmol) and stirred at 100° C. in a sealed reaction vessel for 24 h. The resulting mixture was cooled to room temperature and treated with a solution of sodium metabisulfite (3.6 g, 18.94 mmol) in 24 mL of water. The solid that formed was filtered, rinsed with water and dried: 6.93 g (58%) yield; TLC (10% methanol in ethyl acetate), $R_f$=0.57; $^1$H NMR (DMSO-$d_6$) δ 13.08 (1H, br s, N–1 proton), 10.58 (1H, s, N–5 proton), 6.60 (2H, br s, 6-amino).

[(2R,5R)-5-(6-Amino-3-Iodo-4-methoxypyrazolo[3,4-d]pyrimidinyl)-3-(4-methylphenylcarbonyloxy)oxolan-2-yl]methyl 4-methylbenzoate (15)

To a suspension of (14) (6.68 g, 22.95 mmol) in 150 mL of methanol was added 8.05 mL of a 2.85 M methanolic potassium hydroxide. The mixture was stirred for one minute and then diluted with 100 mL of toluene and evaporated. The solid potassium salt of 1 was dried under vacuum. The potassium salt was suspended in 75 mL of anhydrous DMF and then diluted with 420 mL of anhydrous acetonitrile. 1-Chloro-1,2-dideoxy-3,5-di-O-toluoylribofuranose (8.95 g, 22.95 mmol) was immediately added and the reaction mixture was stirred at room temperature under argon for 1 h. and then filtered. The filtrate was evaporated and the residual foam was recrystallized twice from methanol: 6.59 g (45%) yield; TLC (1:1, ethyl acetate/hexane), $R_f$=0.52; $^1$H NMR (DMSO-$d_6$) δ 7.93 and 7.37 (8H, m and d, J=7.9 Hz for the d, aromatic), 7.10 (2H, br s, 6-amino), 6.51 (1H, t, J=6.6 Hz, 1'-H), 5.69 (1H, m, 3'-H), 4.44 (3H, m, 4'- and 5'-Hs), 3.99 (3H, s, 4-methoxy), 3.19 and 2.63 (2H, 2×m, 2'-Hs), 2.40 and 2.38 (6H, 2×s, toluoyl methyl protons).

[(2R,5R)-5-(6-Amino-3-Iodo-4-methoxypyrazolo[3,4-d]pyrimidinyl)-2-(hydroxymethyl)oxolan-3-ol (16)

To a suspension of 15 (32.4 g, 50.40 mmol) in 600 mL of methanol was added 12.5 mL of 1M sodium methoxide in methanol. The reaction mixture was stirred at reflux for 18 h. and then cooled in a freezer (–10° C.). The crystals of 3 that formed were filtered and rinsed with ice-cold methanol: 10.95 g yield. Acetic acid (12.5 mL) was added to the filtrate and the volume was reduced to about 300 mL. The solution was allowed to sit in the freezer overnight and another crop of crystals (3.95 g) was collected. The filtrate was evaporated to dryness and the residual oil was triturated in ether. The solid that formed was filtered, dried and recrystallized from boiling water: 2.03 g. Total yield=16.93 g (83%); TLC (10% methanol in ethyl acetate), $R_f$=0.23; $^1$H NMR (DMSO-$d_6$) δ 7.02 (2H, br s, 6-amino), 6.33 (1H, t, J=6.1 Hz), 5.24 (1H, d, J=4.4 Hz, 3'-OH), 4.73 (1H, t, J=5.6 Hz, 5'-OH), 4.36 (1H, m, 3'-H), 3.99 (3H, s, 4-methoxy), 3.75 (1H, m, 4'-H), 3.51-3.32 (2H, m, 5'-Hs), 2.79 and 2.17 (2H, 2×m, 2'-Hs). Anal. Calcd. For $C_{11}H_{14}IN_5O_4.0.3H_2O$; C, 32.02; H, 3.57; N, 16.98. Found C, 32.13; H, 3.35; N, 16.77.

1-[(2R,5R)-(5-hydroxymethyl)oxolan-2-yl]-6-amino-3-iodo-5-hydropyrazolo[3,4-d]pyrimidin-4-one (17)

A suspension of (16) (16.84 g, 41.36 mmol) in 1.5 L of 1 N sodium hydroxide solution was heated to reflux. The mixture turned into a homogenous solution and was cooled to 25° C. using an ice-water bath. Acetic acid (90 mL) was added and the solution was stored at 5° C. overnight. The crystals that formed were filtered, rinsed with ice-cold water and dried: 7.47 g yield of 4. The filtrate was evaporated to a volume of about 500 mL and stored at 5° C. overnight. A second crop of crystals was collected (3.75 g). The filtrate was evaporated to about 200 mL. The sodium acetate that formed was filtered off and the filtrate was stored at 5° C. overnight. Another crop of crystal was collected (2.25 g). Total yield: 13.47 g (83%); TLC (5:3:2, n-butanol/water/acetic acid), $R_f$=0.74; $^1$H NMR (DMSO-$d_6$) δ 6.22 (1H, t, J=6.3 Hz, 1'-H), 4.33 (1H, m, 3'-H), 3.73 (1H, m, 4'-H), 3.47 and 3.36 (2H, 2×m, 5'-Hs), 2.63 and 2.12 (2H, 2×m, 2'-Hs). Anal. Calcd. For $C_{10}H_{12}IN_5O_4.0.7H_2O$; C, 29.60; H, 3.33; N, 17.26. Found C, 29.81; H, 3.02; N, 17.00.

N-(3-{1-[(2R,5R)-4-(hydroxymethyl)oxalan-2-yl]-6-amino-4-oxo(5-hydropyrazolo[3,4-d]pyrimidin-3-yl)}prop-2-ynyl)-2,2,2-trifluoroacetamide (18)

To a mixture of 17 (6.00 g, 15.26 mmol), CuI (297 mg, 1.56 mmol) and tetrakis[triphenylphosphine]palladium[0] in 30 mL of anhydrous DMF was added anhydrous triethylamine (3.14 mL) followed by propargyl trifluoroacetimide (4.29 g, 28.41 mmol). The reaction solution was stirred under argon for 40 h. The DMF was evaporated off and the residual oil was triturated in chloroform. The solid of crude 5 that formed was filtered, rinsed with chloroform and dried. The solid was dissolved in a minimum volume of DMF, absorbed onto silica gel and evaporated. The dry mixture was loaded onto a silica gel column and eluted with 10% methanol in ethyl acetate. The product fractions were pooled and evaporated. The residue was precipitated from ethyl acetate/ether: 4.0 g (63%) yield; TLC (20% methanol in ethyl acetate), $R_f$=0.59; $^1$H NMR (DMSO-$d_6$) δ 10.79 (1H, s, $N_5$—H), 10.16 (1H, t, J=5.2 Hz, trifluoroacetimido N—H), 6.77 (2H, br s, 6-amino), 6.28 (1H, t, J=6.3 Hz, 1'-H), 5.23 (1H, d, J=4.1 Hz, 3'-OH), 4.72 (1H, t, J=5.1 Hz, 5'-OH), 4.32 (3H, m, —CONH—$CH_2$— and 3'-H), 3.75 (1H, m, 4'-H), 3.50-3.29 (2H, 2×m, 5'-Hs), 2.65 and 2.15 (2H, 2×m, 2'-Hs). Anal. Calcd. For $C_{15}H_{15}F_3N_6O_5.0.74H_2O$; C, 41.93; H, 3.87; N, 19.56. Found C, 42.33; H, 3.64; N, 19.13.

N-(3-{1-[(2R,5R)-4-(hydroxymethyl)oxalan-2-yl]-6-amino-4-oxo(5-hydropyrazolo[5-4-d]pyriminin-3-yl)}propyl)-2,2,2-trifluoroacetamide (19)

To a solution of (18) (1.0 g, 2.40 mmol) in 100 mL of methanol, containing 0.12 g of 20% palladium hydroxide (preactivated with formic acid), was added 2.0 mL of 4 M triethylammonium formate buffer (pH 6.5). The mixture was shaken under 35 psi of hydrogen gas for 18 h (during some runs it was necessary to add additional catalyst for complete reduction). The mixture was filtered through Celite and the filtrate was evaporated. The residual oil was crystallized from water: 0.79 g (78%) yield; TLC (20% methanol in ethyl acetate), $R_f$=0.52; $^1$H NMR (DMSO-$d_6$) δ 10.59 (1H, s, $N_5$—H), 9.47 (1H, br t, trifluoroacetimido N—H), 6.64 (2H, br s, 6-amino), 6.27 (1H, t, J=6.3 Hz, 1'-H), 5.18 (1H, d, J=4.4 Hz, 3'-OH), 4.75 (1H, t, J=5.9 Hz, 5'-OH), 4.36 (1H, m, 3'-H), 3.75 (1H, m, 4'-H), 3.48 and 3.61 (2H, 2×m, 5'-Hs), 3.22, 2.68 and 1.87 (6H, 3×m, propyl methylene protons), 2.68 and 2.12 (2H, 2×m, 2'-Hs). Anal. Calcd. For $C_{15}H_{19}F_3N_6O_5.0.90H_2O$; C, 41.27; H, 4.80; N, 19.25. Found C, 41.57; H, 4.50; N, 19.11.

N-(3-[(1E)-1-aza-2-(dimethylamino)prop-1-enyl]-[(2R,5R)-4-(hydroxymethyl)oxalan-2-yl]-6-amino-4-oxo(5-hydropyrazolo[5-4-d]pyriminin-3-yl)}propyl)-2,2,2-trifluoroacetamide (20)

To a solution of (19) (0.80 g, 1.98 mmol) in 5.0 mL of anhydrous DMF was added N,N-dimethylformamide dimethylacetal (3.1 mL). The solution was stirred for 2.0 h. under argon and then evaporated. The residue was evaporated twice from xylenes and then placed under vacuum. The amorphous solid (20) that formed was triturated with ether and collected: 773-mg (82%) yield; TLC (20% methanol in ethyl acetate), $R_f$=0.47; $^1$H NMR (DMSO-$d_6$) δ 11.22 (1H, br s, $N_5$—H), 9.47 (1H, t, J=5.5 Hz, trifluoroacetimido N—H), 8.67 (1H, s, N=CH—N), 6.42 (1H, t, J=6.5 Hz, 1'-H), 5.22 (1H, d, J=4.3 Hz, 3'-OH), 4.75 (1H, t, J=6.1 Hz, 5'-OH), 4.40 (1H, m, 3'-H), 3.77 (1H, m, 4'-H), 3.50 and 3.38 (2H, 2×s, 5'-Hs), 3.18 and 3.05 (6H, 2×s, N,N-dimethyl Hs), 3.22, 2.72 and 1.89 (6H, 3×m, propyl methylene Hs), 2.72 and 2.15 (2H, 2×m, 2'-Hs). Anal. Calcd. For $C_{18}H_{24}F_3N_7O_5.0.40H_2O$; C, 44.80; H, 5.18; N, 20.32. Found C, 45.02; H, 4.96; N, 19.94.

N-{3-[1-((2R,5R)-5-{[bis(4-methoxyphenyl)phenylmethoxy]methyl}-4-hydroxyoxolan-2-yl)-6-amino-4-oxo(5-hydropyrazolo[3,4-d]pyrimidin-3-yl)]propyl}-2,2,2-trifluoroacetamide (21)

To a solution of (20) (723-mg, 1.52 mmol) in 9.0 mL of anhydrous pyridine was added 4,4'-dimethoxytrityl chloride (0.61 g, 1.80 mmol). The reaction solution was stirred for 3.0 h. under argon and then poured into 100 mL of 5% sodium bicarbonate solution. The aqueous solution was extracted with ethyl acetate (2×200 mL) and the dried extracts (sodium sulfate) were evaporated. The crude product was purified by silica gel chromatography eluting with a solvent gradient of 0-5% methanol in ethyl acetate (2% triethylamine). The product fractions were evaporated affording 21 as an amorphous solid: 724-mg (61%) yield; TLC (5% methanol in ethyl acetate), $R_f$=0.39; $^1$H NMR (DMSO-$d_6$) δ 11.27 (1H, s, $N_5$—H), 9.43 (1H, t, J=5.3 Hz, trifluoroacetimido N—H), 8.71 (1H, s, N=CH—N), 7.32, 7.17 and 6.76 (13H, 3×m, aromatic), 6.45 (1H, t, J=6.3 Hz, 1'-H), 5.26 (1H, d, J=5.3 Hz, 3'-OH), 4.45 (1H, m, 3'-H), 3.90 (1H, m, 4'-H), 3.70 (6H, s, OMe Hs), 3.18 and 3.05 (10H, 2×s, N,N-dimethyl, 5'-Hs and CONH—$CH_2$), 2.62 and 1.65 (4H, 2×m, methylene Hs), 2.62 and 2.20 (2H, 2×m, 2'-Hs). Anal. Calcd. For $C_{39}H_{42}F_3N_7O_7.0.30H_2O$; C, 59.81; H, 5.48; N, 12.52. Found C, 59.80; H, 5.39; N, 12.63.

N-{3-[1-((2R,5R)-5{[bis(4-methoxyphenyl)phenyl-methoxy]methyl}-4-{[bis(methylethyl)amino](2-cyanoethoxy)phosphinooxy}oxolan-2-yl)-6-amino-4-oxo(5-hydropyrazolo[3,4-d]pyrimidin-3-yl)]propyl}-2,2,2-trifluoroacetamide (22.)

To a solution of (21) (700-mg, 0.900 mmol) in 22 mL of anhydrous methylene chloride, containing 0.47 mL of diisopropylethylamine, was added 2-cyanoethyl N,N-diisopropylchlorophosphoramidite (0.34 mL, 1.52 mmol). After stirring for 30 minutes under argon at 25° C. the solution was treated with 3.0 mL of methanol and diluted with 200 mL of ethyl acetate. The solution was washed with 100 mL of 5% sodium bicarbonate solution and dried over sodium sulfate and evaporated. The crude product was purified by silica gel chromatography eluting with 2% triethylamine in ethyl acetate. The product fractions were evaporated and the residue was precipitated from ether-hexane: 583-mg (66%) yield; TLC (ethyl acetate), $R_f$=0.38; $^{31}$P NMR (DMSO-$d_6$, reference to 85% phosphoric acid) δ 145.50 and 144.72.

Example 4

This example illustrates the preparation of 3-{[5-(4,6-bis{(1E)-1-aza-2-[bis(2-methylpropyl)amino]vinyl}-3-prop-1-ynylpyrazolo[3,4-d]pyrimidinyl)-2-{[bis(4-methoxyphenyl)phenylmethoxy]-methyl}oxolan-3-yloxy][ethyl(methylethyl)amino]-phosphino}propanenitrile (26).

5-(4,6-bis{(1E)-1-aza-2-[bis(2-methylpropyl)amino]vinyl}-3-prop-1-ynylpyrazolo[3,4-d]pyrimidinyl)-2(hydroxymethyl)oxolan-3-ol (24)

Compound (23) (1 mmol) can be stirred for 5 hr at room temperature with (dimethoxymethyl)bis(2-methylpropyl) amine (0.5 mL, 3.37 mmol). The reaction mixture can be reduced in vacuo, and the protected compound can be purified on silica gel to yield (24) (Vincent et al).

5-(4,6-bis{(1E)-1-aza-2-[bis(2-methylpropyl)amino] vinyl}-3-prop-1-ynylpyrazolo[3,4-d]pyrimidinyl)-2-{[bis(4-methoxyphenyl)phenylmethoxy]-methyl}oxolan-3-ol (25)

To a solution of (24) (1.50 mmol) in 9.0 mL of anhydrous pyridine 4,4'-dimethoxytrityl chloride (0.61 g, 1.80 mmol) can be added. The reaction solution can be stirred for 3.0 h. under argon and then can be poured into 100 mL of 5% sodium bicarbonate solution. The aqueous solution can be extracted with ethyl acetate (2×200 mL) and the extracts can be dried (sodium sulfate) and evaporated. The crude product can be purified by silica gel chromatography with an appropriate gradient to yield (25).

3-{[5-(4,6-bis{(1E)-1-aza-2-[bis(2-methylpropyl) amino]vinyl}-3-prop-1-ynylpyrazolo[3,4-d]pyrimidinyl)-2-{[bis(4-methoxyphenyl)phenylmethoxy]methyl}-oxolan-3-yloxy][ethyl(methylethyl) amino}phosphino}propanenitrile (26)

To a solution of (25) (0.900 mmol) in 22 mL of anhydrous methylene chloride, containing 0.47 mL of diisopropylethylamine, 2-cyanoethyl N,N-diisopropylchlorophosphoramidite (0.34 mL, 1.52 mmol) can be added. The solution can be stirred for 30 minutes under argon at 25° C. and the can be treated with 3.0 mL of methanol and diluted with 200 mL of ethyl acetate. The solution can then be washed with 100 mL of 5% sodium bicarbonate solution and dried over sodium sulfate and evaporated. The crude product can be purified by silica gel chromatography with an appropriate gradient to yield (26).

Example 5

This example illustrates the synthesis of 5-[4,6-diamino-3-(2-methoxyethynyl)pyrazolo[3,4-d]pyrimidinyl]-2-(hydroxymethyl)oxolan-3-ol (27).

5-[4,6-diamino-3-(2-methoxyethynyl)pyrazolo[3,4-d]pyrimidinyl]-2-(hydroxymethyl)oxolan-3-ol (27)

To a mixture of 4,6-diamino-1-(2-deoxy-β-D-erythro-pentofuranosyl)-3-iodo-1H-pyrazolo[3,4-d]pyrimidine (4.2 g, 10.71 mmol), CuI (211 mg, 1.10 mmol), Pd(PPh$_3$)$_4$ (635 mg, 0.553 mmol), and triethylamine (2.2 mL) in 20 mL of anhydrous DMF was added methyl propargyl ether (1.82 mL). The mixture was stirred under argon for 16 h. and then evaporated to dryness. The residue was crystallized from methanol: 3.20 g (89%) yield; TLC (30% methanol in ethyl acetate), $R_f$=0.63; $^1$H NMR (DMSO-$d_6$) δ 7.44 (2H, br d, amino), 6.32 (1H, t, J=6.6 Hz, 1'-H), 6.33 (2H, br s, amino), 5.20 (1H, d, J=4.1 Hz, 3'-OH), 4.75 (1H, br t, 5'-OH), 4.40 (2H, s, methylene), 4.36 (1H, m, 3'-H), 3.76 (1H, m, 4'-H), 3.47 & 3.32 (2H, 2×m, 5'-Hs), 3.32 (3H, s, methoxy), 2.68 & 2.14 (2H, 2×m, 2'-Hs).

Synthesis of 5-{6-[(1E)-1-aza-2-(dimethylamino) vinyl]-4-[(1Z)-1-aza-2-(dimethylamino)vinyl]pyrazolo[3,4-d]pyrimidinyl}-2-(hydroxymethyl)oxolan-3-ol, 1-methoxyprop-1-yne (28)

Compound 27 (3.1 g, 9.28 mmol) was stirred in a solution of 30 mL of N,N-dimethylformamide and 15 mL of N,N-dimethylformamide dimethyl acetal for 14 h at 45° C. The solvents were evaporated and the residue was evaporated twice from xylenes affording 28 as a foam which was precipitated from ethyl acetate-ether: 2.8 g (68%) yield; TLC (50% methanol in ethyl acetate), $R_f$=0.36.

Synthesis of 3-[(5-{6-[(1E)-1-aza-2-(dimethylamino) vinyl]-4-[(1Z)-1-aza-2-(dimethylamino)vinyl]pyrazolo[3,4-d]pyrimidinyl}-2-{[bis(4-methoxyphenyl) phenylmethoxy]methyl}oxolan-3-yloxy)[bis (methylethyl)amino]phosphinooxy]propanenitrile (29)

To a solution of 28 (2.7 g, 6.08 mmol) in 45 mL of anhydrous pyridine was added dimethoxytrityl chloride (2.4 g). The resulting solution was stirred for 3 h. at room temperature and then poured into 200 mL of 5% sodium bicarbonate solution. The mixture was extracted with ethyl acetate and the extract was dried over sodium sulfate, filtered and evaporated. The residue was purified by silica gel chromatography eluting with a gradient of 0-40% methanol in ethyl acetate. The pure 5'-O-DMT derivative fractions were pooled and evaporated affording a foam: 1.0 g (22%) yield.

To a solution of DMT derivative (0.98 g, 1.31 mmol) in 16 mL of anhydrous methylene chloride, containing 0.70 mL of N,N-diisopropylethylamine was added 2-cyanoethyl diisopropylchlorophosphoramidite (0.50 mL) under argon. The solution was stirred for 30 min at room temperature and then treated with 1.0 mL of methanol. The solution was loaded directly on to a silica gel column and eluted with a gradient of 0-20% methanol in ethyl acetate (2% triethylamine). The pure fractions were pooled and evaporated affording a foam: 0.25 g (20%) yield.

Example 6

This example illustrates the preparation of 3-[(5-{4-[(1Z)-1-aza-2-(methylamino)vinyl]-3-(2-furyl)pyrazolo[3,4-d]pyrimidinyl}-2-{[bis(4-methoxyphenyl)phenylmethoxy]methyl}oxolan-3-yloxy)[bis(methylethyl)amino]-phosphinooxy]propanenitrile (35) (See Reaction Scheme 8).

(2-Furylmethoxymethylene)methane-1,1-dicarbonitrile (30)

To an ice-cold solution containing anhydrous methylene chloride (500 mL), triethylamine (100 mL), and malononitrile (30 g, 454 mmol) was added 2-furanyl chloride (50 g, 383 mmol) by dropwise addition over a 20 min period. Stirring was then continued for an additional hour at ambient temperature. The reaction solution was washed with 1.5 L of ice-cold 2N HCl solution and then with 1.5 L of water. The organic phase was evaporated affording an oil.

A portion of the product oil (4.6 g, 28.75 mmol) was dissolved in a solution consisting of 40 mL of dioxane and 4.0 mL of water. Dimethyl sulfate (15 mL) and sodium bicarbonate (15 g) were added and the reaction solution was stirred for 2.5 h at 80° C. The mixture was then dissolved in 100 mL of water and the product was extracted with 200 mL of ethyl acetate. The organic solution was washed with 100 mL of 5% sodium bicarbonate solution followed by 100 mL of water. The solution was dried over sodium sulfate, filtered and evaporated affording an oil which solidified under vacuum: 2.72 g yield; TLC (1:1, ethyl acetate/hexane), $R_f$=0.42; $^1$H NMR ((DMSO-$d_6$) δ 8.25 (1H, m, aromatic), 7.63 (1H, m, aromatic), 6.92 (1H, m, aromatic), 4.23 (3H, s, methoxy).

2-Amino-4-(2-furyl)furan-3-carbonitrile (31)

Hydrazine monohydrate (3.4 mL, 80 mmol) was added dropwise to an ice-cold solution of 30 (2.72 g, 15.63 mmol) in 75 mL of methanol over a period of 15 min. The solution was then evaporated to dryness affording an oil which solidified under vacuum. The solid was triturated with ether, filtered and dried: 2.2 g (81%) yield; TLC (ethyl acetate), $R_f$=0.81; $^1$H NMR (DMSO-$d_6$) δ 7.77 (1H, s, furanyl), 6.80 (1H, m, furanyl), 6.61 (1H, m, furanyl), 6.41 (2H, br s, amine).

3-(2-furyl)pyrazolo[3,4-d]pyrimidine-4-ylamine (32)

Compound 31 (25.7 g, 148 mmol) was stirred in 250 mL of formamide at 190° C. for 4 h. The solution was then cooled to room temperature, diluted with 1.2 L of water and chilled in an ice-bath. The solid that formed was filtered and dried: 22 g (74%) yield; TLC (5% methanol in ethyl acetate), $R_f$=0.25.

[5-(4-Amino-3-(2-furyl)pyrazolo[3,4-d]pyrimidinyl)-3-(4-methylphenylcarbonyloxy)-2-oxoethyl]oxolan-2-yl]methyl 4-methylbenzoate (33)

Compound 32 (10 g, 49.7 mmol) was stirred in 200 mL of 0.29 M methanolic KOH solution for 5 min. The mixture was evaporated to dryness and the residue was then dissolved in 40 mL of hot anhydrous DMF. The solution was cooled to room temperature and then diluted with 230 mL of anhydrous acetonitrile. The chlorosugar derivative (23 g, 59.14 mmol) was added immediately and the mixture was stirred for 45 min and then evaporated to dryness. The residue was dissolved in 800 mL of ethyl acetate and washed with water (2×800 mL). The organic solution was dried over sodium sulfate, filtered and evaporated. The crude product was purified by silica-gel chromatography eluting with a gradient of 30-0% hexane in ethyl acetate. The pure product fractions were evaporated and the residue was crystallized from hot methanol: 3.4 g (12%) yield; TLC (ethyl acetate), $R_f$=0.47; $^1$H NMR ((DMSO-$d_6$) δ 8.27 (1H, s, 6-H), 7.96 (1H, m, furanyl), 7.95, 7.84, 7.36 & 7.23 (8H, 4×d, toluoyl aromatic), 6.83 (1H, m, furanyl), 6.80 (1H, t, J=6.3 Hz, 1'-H), 6.70 (1H, m, furanyl), 5.86 (1H, m, 3'-H), 4.64-4.42 (3H, m, 4'-H and 5'-Hs), 3.28 & 2.76 (2H, 2×m, 2'-Hs), 2.39 & 2.36 (6H, 2×s, toluoyl methyls).

5-{4-[(1Z)-1-aza-2-(dimethylamino)vinyl]-3-(2-furyl)pyrazolo[3,4-d]pyrimidinyl}-2-(hydroxymethyl)oxolan-3-ol (34)

A suspension of 33 (3.36 g, 6.08 mmol) in 17 mL of 0.12 M methanolic sodium methoxide solution was refluxed for 30 min. The resulting solution was cooled to room temperature and neutralized by addition of 0.12 mL of acetic acid. The solution was evaporated to dryness and the product was precipitated from methanol-ether and then recrystallized from boiling water: 1.63 g (85%) yield of the deprotected nucleoside.

All of the nucleoside product from above was stirred in a solution consisting of 30 mL of anhydrous DMF and 15 mL of N,N-dimethylformamide dimethylacetal for 5 h. The solution was evaporated to dryness and the residue was then evaporated twice from xylenes affording a foam: 1.89 g (99%) yield; TLC (20% methanol in ethyl acetate), $R_f$=0.45; $^1$H NMR ((DMSO-$d_6$) δ 8.98 & 8.46 (2H, 2×s, formamidine C—H and 6-H), 7.97 (1H, m, furanyl), 7.81 (1H, m, furanyl), 6.65 (2H, m, 1'-H and furanyl), 5.30 (1H, d, J=4.5 Hz, 3'-OH), 4.79 (1H, t, J=5.5 Hz, 5'-OH), 4.51 (1H, m, 3'-H), 3.85 (1H, m, 4'-H), 3.57 & 3.40 (2H, 2×m, 5'-Hs), 3.26 & 3.21 (6H, 2×s, N-Me protons), 2.88 & 2.30 (2H, 2×m, 2'-Hs).

3-[(5-{4-[(1Z)-1-aza-2-(methylamino)vinyl]-3-(2-furyl)pyrazolo[3,4-d]pyrimidinyl}-2-{[bis(4-methoxyphenyl)phenylmethoxy]methyl}oxolan-3-yloxy)[bis(methylethyl)amino]-phosphinooxy]propanenitrile (35)

Dimethoxytrityl chloride (2.01 g) was added to a solution of 34 (1.84 g, 4.95 mmol) dissolved in 30 mL of dry pyridine. The reaction solution was stirred for 3 h at room temperature and then poured into 200 mL of 5% sodium bicarbonate solution. The product was extracted with 300 mL of ethyl acetate and the organic phase was dried over sodium sulfate and evaporated. The residue was purified using silica gel chromatography eluting with a gradient of 0-5% methanol in ethyl acetate. The pure product fractions were evaporated affording a foam: 2.26 g (68%) yield of the 5'-O-DMT derivative.

To a solution of the DMT derivative (2.18 g, 3.23 mmol) dissolved in 40 mL of dry methylene chloride, containing 1.75 mL of N,N-diisopropylethylamine, was added 1.25 mL of 2-cyanoethyl diisopropylchlorophosphoramidite. The solution was stirred under argon for 15 min at room temperature and then treated with 5 mL of methanol. The resulting solution was diluted with 500 mL of ethyl acetate and washed with 400 mL of 5% sodium bicarbonate solution. The organic solution was dried over sodium sulfate, filtered and evaporated. The residue was purified by silica gel chromatography eluting with a gradient of 5-10% methanol in ethyl acetate (2% triethylamine). The pure product fractions were evaporated affording a foam: 1.62 g (57%) yield; $^{31}$P NMR (DMSO-d$_6$) δ 147.81 and 147.16.

Example 7

This example illustrates the preparation of 3-[(5-{6-[(1E)-1-aza-2-(dimethylamino)vinyl]-4-[(1Z)-1-aza-2-(dimethylamino)vinyl]-3-(2-furyl)pyrazolo[3,4-d]pyrimidinyl}-2-{[bis(4-methoxyphenyl)phenylmethoxy]methyl}oxolan-3-yloxy)[bis(methylethyl)amino]phosphinooxy]propanenitrile (39, See Reaction Scheme 9).

3-(2-furyl)pyrazolo[3,4-d]pyrimidine-4,6-diamine (36)

A mixture of finely ground 31 (10.0 g, 57.47 mmol) and guanidine carbonate (16.6 g, 91.95 mmol) was heated at 230° C. for 45 min. The mixture was cooled to room temperature and the solid was triturated in 100 mL of boiling water. The solid (pure 36) was filtered, rinsed with water and dried: 11.1 g (89%) yield; TLC (40% methanol in ethyl acetate), R$_f$=0.66; $^1$H NMR ((DMSO-d$_6$) δ 12.68 (1H, br s, N—H), 7.86 (1H, m, furanyl), 6.93 (2H, br s, —NH$_2$), 6.85 (1H, d, J=3.5 Hz, furanyl), 6.65 (1H, m, furanyl), 6.10 (2H, br s, —NH$_2$).

5-(4,6-diamino-3-(2-furyl)pyrazolo[3,4-d]pyrimidinyl)-2-(hydroxymethyl)oxolan-3-ol (37)

Compound 36 (10.5 g, 48.61 mmol) was stirred in 200 mL of 0.29 M methanolic KOH solution for 5 min. The mixture was evaporated to dryness and the residue was then dissolved in 105 mL of hot anhydrous DMF. The solution was cooled to room temperature and then diluted with 620 mL of anhydrous acetonitrile. The chlorosugar derivative (23 g, 59.14 mmol) was added immediately and the mixture was stirred for 40 min and then filtered. The filtrate was evaporated to dryness and the residue was chromatographed through a silica gel column eluting with ethyl acetate. The nucleoside fractions were evaporated affording 2.8 g (10% yield) of the toluoyl protected nucleoside as a mixture of alpha- and beta-anomers. This mixture was refluxed in 40 mL of 0.19 M methanolic sodium methoxide for 45 min. The reaction solution was placed in a freezer overnight producing a crop of crystals corresponding to the pure beta-anomer 37: 690 mg yield; TLC (20% methanol in ethyl acetate), R$_f$=0.32; $^1$H NMR (DMSO-d$_6$) δ 7.90 (1H, m, furanyl), 6.99 (2H, br s, amino), 6.86 (1H, d, J=4.1 Hz, furanyl), 6.68 (1H, m, furanyl), 6.41 (1H, t, J=6.6 Hz, 1'-H), 6.26 (2H, br s, amino), 5.21 (1H, d, J=4.4 Hz, 3'-OH), 4.82 (1H, t, J=5.8 Hz, 5'-OH), 4.42 (1H, m, 3'-H), 3.79 (1H, m, 4'-H), 3.52 & 3.41 (2H, 2×m, 5'-Hs), 2.75 & 2.18 (2H, 2×m, 2'-Hs).

5-{6-[(1E)-1-aza-2-(dimethylamino)vinyl]-4-[(1Z)-1-aza-2-(dimethylamino)vinyl]-3-(2-furyl)pyrazolo[3,4-d]pyrimidinyl}-2-(hydroxymethyl)oxolan-3-ol (38)

A solution of 37 (0.68 g, 2.05 mmol) in 30 mL of anhydrous DMF and 15 mL of N,N-dimethylformamide dimethylacetal was stirred at room temperature for 24 h. The solution was evaporated to dryness and the residue was evaporated twice from xylenes affording a foam: 0.90 g (99%) yield; TLC (50% methanol in ethyl acetate), R$_f$=0.38; $^1$H NMR (DMSO-d$_6$) δ 8.93 & 8.77 (2H, 2×s, formamidine C-Hs), 7.94 (1H, m, furanyl), 7.76 (1H, m, furanyl), 6.62 (1H, m, furanyl), 6.60 (1H, t, J=6.6 Hz, 1'-H), 5.25 (1H, d, J=4.4 Hz, 3'-OH), 4.84 (1H, t, J=5.9 Hz, 5'-OH), 4.47 (1H, m, 3'-H), 3.83 (1H, m, 4'-H), 3.56 & 3.41 (2H, 2×m, 5'-Hs), 3.25, 3.18, 3.16 & 3.03 (12H, 4×s, N-methyls), 2.82 & 2.22 (2H, 2×m, 2'-Hs).]

3-[(5-{6-[(1E)-1-aza-2-(dimethylamino)vinyl]-4-[(1Z)-1-aza-2-(dimethylamino)vinyl]-3-(2-furyl)pyrazolo[3,4-d]pyrimidinyl}-2-{[bis(4-methoxyphenyl)phenylmethoxy]methyl}oxolan-3-yloxy)[bis(methylethyl)amino]phosphinooxy]propanenitrile (39)

Dimethoxytrityl chloride (0.85 g) was added to a solution of 38 (0.90 g, 2.04 mmol) in 12 mL of dry pyridine. The reaction solution was stirred for 2 h at room temperature and then poured into 200 mL of 5% sodium bicarbonate solution. The product was extracted with ethyl acetate (3×300 mL) and the pooled organic extracts were dried over sodium sulfate and evaporated. The residue was purified using silica gel chromatography eluting with a gradient of 20-30% methanol in ethyl acetate. The pure product fractions were evaporated affording a foam: 286-mg yield of the 5'-O-DMT derivative.

To a solution of the DMT derivative (286 mg, 0.384 mmol) dissolved in 5 mL of dry methylene chloride, containing 0.23 mL of N,N-diisopropylethylamine, was added 0.17 mL of 2-cyanoethyl diisopropylchlorophosphoramidite. The solution was stirred under argon for 15 min at room temperature and then treated with 0.5 mL of methanol. The resulting solution was diluted with 100 mL of ethyl acetate and washed with 75 mL of 5% sodium bicarbonate solution. The organic solution was dried over sodium sulfate, filtered and evaporated. The residue was purified by silica gel chromatography eluting with a gradient of 0-30% methanol in ethyl acetate (2% triethylamine). The pure product fractions were evaporated affording a foam: 230 mg (12%) yield; $^{31}$P NMR (DMSO-d$_6$) δ 147.77 and 147.08.

Example 8

This example illustrates the preparation of 4-[1-(5-{[bis(4-methoxyphenyl)phenylmethoxy]methyl}-4-{[bis(methylethyl)amino](2-cyanoethoxy)phosphinooxy}oxolan-2-yl)-2,4-dioxo-1,3-dihydropyrimidin-5-yl]but-3-ynyl 4-methylbenzoate (see, 42 Reaction Scheme 10).

Synthesis of 3-Butyn-1-yl p-Toluate (40)

In a 500 mL round bottom flask equipped with a magnetic stirring bar and under inert atmosphere, 3-butyn-1-ol (50.3 g, 0.718 mol) was dissolved with anhydrous pyridine (200 mL) and the solution was cooled in an ice water bath. To the cold solution, using an addition funnel, p-toluyl chloride (136.6 g, 0.86 mol, 1.2 eq) was added dropwise and the reaction mixture was stirred at room temperature overnight.

To the mixture were added diethyl ether (350 mL) and water (100 mL). The organic layer was separated, and the aqueous solution was washed with diethyl ether (150 mL). The organic fractions were combined and washed with 10% HCl (3×100 mL), saturated NaHCO$_3$ solution (2×100 mL) and water (1×50 mL). The resulting solution was dried over anhydrous Na$_2$SO$_4$, filtered and the solvent was removed to give 142 g (quantitative yield) of (40) as an off-white solid. The product can be recrystallized form hexane or methanol, but was sufficiently pure to proceed to the next step.

$^1$H NMR (CDCl$_3$, 300 MHz) δ (ppm) 7.95 (d, 2H, J=8.1 Hz), 7.24 (d, 2H, J=8.1 Hz), 4.41 (t, 2H, J=6.8 Hz), 2.67 (dd, 2H, J$_1$=2.6 J$_2$=6.8 Hz), 2.40 (s, 3H), 2.03 (t, 1H, J=2.4 Hz).

5'-DMT-5-[4-(p-toluyloxy)butynyl]-2'-deoxyurdine (41)

A mixture of 5-iodo-2'-deoxyuridine (4.0 g, 11.30 mmol), 4-(p-toluyloxy)butyne (40) (5.7 g, 30.3 mmol), CuI (222 mg, 1.16 mmol), tetrakis[triphenylphosphine]palladium[0] (0.67 g, 0.583 mmol) and triethylamine (2.0 mL) was stirred in 30 mL of anhydrous DMF under argon for 16 h. The mixture was evaporated to dryness and the residual oil solidified after stirring in 100 mL of ether. This solid was filtered and dried under vacuum.

A portion of the crude product (1.5 g) was dissolved in 20 mL of anhydrous pyridine and treated with dimethoxytrityl chloride (1.3 g). The solution was stirred for 2.0 h. under argon and then poured into 150 mL of 5% sodium bicarbonate solution. The product was extracted with 200 mL of ethyl acetate. The extract was dried over sodium sulfate, filtered and the solvent evaporated. The residue was purified by silica gel chromatography eluting with a gradient of 30-0% hexane in ethyl acetate). The product fractions were evaporated, affording a foam: 957-mg yield. TLC (30% hexane in ethyl acetate), $R_f$=0.37; $^1$H NMR (DMSO-$d_6$) δ 11.66 (1H, s, N—H), 7.9-6.8 (18H, aromatic protons), 6.11 (1H, t, J=6.6 Hz, 1'-H), 5.35 (1H, br s, 3'-OH), 4.29 (1H, m, 3'-H), 4.15 (2H, t, J=6.8 Hz, butyne methylene), 3.92 (1H, m, 4'-H), 3.71 (6H, s, methoxy groups), 3.24 & 3.07 (2H, 2×m, 5'-Hs), 2.64 (2H, t, J=6.8 Hz, butyne methylene), 2.37 (3H, s, toluyl methyl), 2.23 (2H, m, 2'-Hs).

4-[1-(5-{[bis(4-methoxyphenyl)phenylmethoxy]methyl}-4-{[bis(methylethyl)amino](2-cyanoethoxy)phosphinooxy}oxolan-2-yl)-2,4-dioxo-1,3-dihydropyrimidin-5-yl]but-3-ynyl 4-methylbenzoate (42)

To a solution of the DMT derivative from above (0.92 g, 1.28 mmol) in 15 mL of anhydrous methylene chloride, containing 0.75 mL of N,N-diisopropylethylamine, was added 2-cyanoethyl diisopropylchlorophosphoramidite (0.56 mL). The solution was stirred for 30 min at room temperature under argon and then treated with 1.0 mL of methanol. The solution was evaporated down to about a 5 mL volume and loaded directly on to a silica gel column and eluted with 40% hexane in ethyl acetate (2% triethylamine). The pure fractions were pooled and evaporated, affording a foam: 0.91 g of (42) (78%) yield; $^{31}$P NMR (DMSO-$d_6$) δ 147.72 & 147.39.

Example 9

This example illustrates the enhanced ability of modified oligonucleotides to discriminate between related target sequences.

Figure 3:
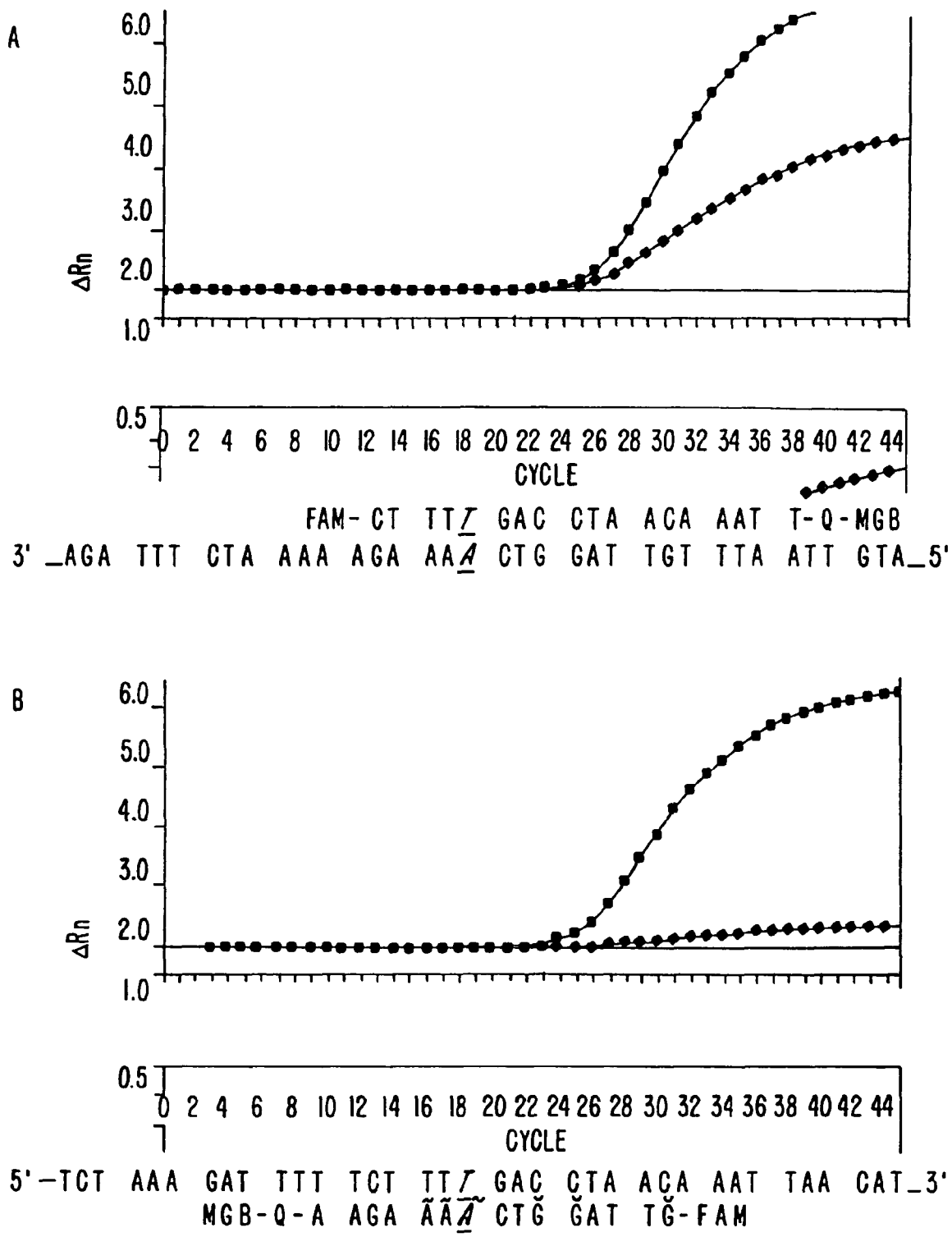
FIG. 3 is a chart which illustrates one advantage achieved through the use of PPPA and PPG in MGB-modified oligonucleotide probes. As seen in the figure, the modified bases allow shortening of the probe that shows increased mismatch discrimination in real-time PCR. Ã is PPPA and G̃ is PPG. MGB-modified FAM probe=SEQ ID NO:1; MGB-modified FAM probe complement=SEQ ID NO:2; PPPA and PPG containing MGB-modified FAM probe complement=SEQ ID NO:3; PPPA and PPG containing MGB-modified FAM probe=SEQ ID NO:4.

In this example, modified oligonucleotides were prepared containing PPPA, PPG and a minor groove binder. As FIG. 3 illustrates, the use of a MGB in combination with PPPA and PPG increases the $T_m$ and allows the design of shorter probes compatible with PCR extension temperatures. These modified oligonucleotides also yield increased mismatch discrimination. In a first design of a 18-mer fluorescein-ODN-Red 13quencher-MGB real-time PCR probe, poor discrimination of an A/T mismatch was observed as shown in FIG. 3A. Re-design of the probe against the opposite strand, putting the mismatch under the MGB and substituting PPPA for A and PPG for G as indicated, allows shortening of the probe to a 15-mer. This probe now gives good mismatch discrimination as shown in FIG. 3B.

A thermodynamic investigation of mismatch discrimination was performed on a set of oligonucleotides hybridized to a set of targets perfectly match or containing a single mismatch. The target sequences contain a) normal As, b) PPPA, c) normal As and a 3'-MGB and d) PPPA and a 3'-MGB, respectively. The sequences for the probes and targets are shown below in Table 3a and 3b. The determination of $T_m$s and the calculation of TABLE 3a and 3b Probe and target sequences

| Number | Mismatch | Probe Sequence | SEQ ID NO: |
|---|---|---|---|
| A. Probe Sequences - Mismatch Underlined |||||
| 1 | Complement | AAAGTTATGTCTACTTACAGAAA | 17 |
| 2 | A/C | AAAGCTATGTCTACTTACAGAAA | 18 |
| 3 | A/C | AAAGTCATGTCTACTTACAGAAA | 19 |
| 4 | T/G | AAAGTTGTGTCTACTTACAGAAA | 20 |
| 5 | A/C | AAAGTTACGTCTACTTACAGAAA | 21 |
| 6 | C/A | AAAGTTATATCTACTTACAGAAA | 22 |
| 7 | A/C | AAAGTTATGCCTACTTACAGAAA | 23 |
| 8 | G/T | AAAGTTATGTTTACTTACAGAAA | 24 |
| 9 | A/C | AAAGTTATGTCCACTTACAGAAA | 25 |
| 10 | T/G | AAAGTTATGTCTGCTTACAGAAA | 26 |
| 11 | G/T | AAAGTTATGTCTATTTACAGAAA | 27 |
| 12 | A/C | AAAGTTATGTCTACCTACAGNAA | 28 |
| 13 | A/C | AAAGTTATGTCTACTCACAGAAA | 29 |
| 14 | T/G | AAAGTTATGTCTACTTGCAGAAA | 30 |
| B. Target Sequences - A' = PPPA |||||
| 1 | | GTAAGTAGACATAAC | 31 |
| 2 | | GTA'A'GTA'GA'CA'TA'A'C | 32 |
| 3 | | GTAAGTAGACATAAC-MGB | 33 |
| 4 | | GTA'A'GTA'GA'CA'TA'A'C-MGB | 34 |

TABLE 3c

Thermodynamic comparison of mismatch discrimination in terms of free energy increment at 50° C. where $\Delta\Delta G°_{50}$ = $R°\ln(K_{match}/K_{mismatch})$

| Number | Mismatch | A | PPPA | MGB | MGB + PPPA |
|---|---|---|---|---|---|
| 2 | A/C | 2340 | 2930 | 2870 | 5320 |
| 3 | A/C | 2560 | 3280 | 4100 | 6320 |
| 4 | T/G | 1950 | 1810 | 4200 | 5900 |
| 5 | A/C | 3520 | 3760 | 3830 | 4980 |
| 6 | C/A | 5030 | 5340 | 4190 | 5970 |
| 7 | A/C | 3000 | 3370 | 4310 | 5260 |
| 8 | G/T | 3040 | 3260 | 3070 | 4820 |
| 9 | A/C | 3290 | 3440 | 3810 | 5630 |
| 10 | T/G | 1800 | 1950 | 2090 | 3350 |
| 11 | G/T | 3340 | 3120 | 3630 | 5070 |

TABLE 3c-continued

Thermodynamic comparison of mismatch discrimination in terms of free energy increment at 50° C. where $\Delta\Delta G°_{50}$ = $R°\ln(K_{match}/K_{mismatch})$

| Number | Mismatch | A | PPPA | MGB | MGB + PPPA |
|---|---|---|---|---|---|
| 12 | A/C | 2940 | 3620 | 2550 | 4490 |
| 13 | A/C | 2360 | 3210 | 1820 | 3980 |
| 14 | T/G | 1600 | 2010 | 2000 | 2480 |

$\Delta\Delta G°_{50}$ is described in Example 9. Table 3c clearly shows increased mismatch discrimination when PPPA is substituted for A and even larger discrimination when PPPA is combined with a MGB.

Comparison of the thermodynamic discrimination of mismatched base pairs formed in MGB-ODNs containing HO-PPPA/HO-PU with PPPA/PU at 37° C. is shown in Table 4. The ODNs containing the modified bases in combination with MGB were hybridized to their complements. Mismatches are underlined in the sequences shown in Table 4. As shown in this table, HO-PPPA and HO-PU substitution compared to PPPA and PU, shown for the most part increased mismatch discrimination.

TABLE 4

Comparison of thermodynamic discrimination of mismatched base pairs formed by HOPPPA or HOPU vs PPPA and PU in the 8-mer duplexes (+MGB).

| | Sequence of Duplex | SEQ ID NO: | PPPA/PU $\Delta\Delta G$ cal/mol | HOPPPA/HOPU $\Delta\Delta G$ cal/mol |
|---|---|---|---|---|
| Match | CGUCACUG-MGB AGCTGTGACT | 35 | | |
| 1 | CGUCACUG-MGB AGCTGTGACT | 36 | 4250 | 4350 |
| 2 | CGUCACUG-MGB AGCGGTGACT | 37 | 3450 | 3540 |
| 3 | CGUCACUG-MGB AGCCGTGACT | 38 | 4860 | 4530 |
| 4 | CGUCACUG-MGB AGCAGAGACT | 39 | 4870 | 4850 |
| 5 | CGUCACUG-MGB AGCAGGGACT | 40 | 4190 | 4360 |
| 6 | CGUCACUG-MGB AGCAGCGACT | 41 | 3930 | 3940 |
| 7 | CGUCACUG-MGB AGCAATGACT | 42 | 2600 | 2300 |
| 8 | CGUCACUG-MGB AGCATTGACT | 43 | 4360 | 4210 |
| 9 | CGUCACUG-MGB AGCACTGACT | 44 | 4420 | 4610 |
| Match | UAUUAUUG-MGB AATAATAACC | 45 | | |
| 10 | UAUUAUUG-MGB AATTATAACC | 46 | 4400 | 5000 |
| 11 | UAUUAUUG-MGB AATGATAACC | 47 | 3740 | 3760 |
| 12 | UAUUAUUG-MGB AATCATAACC | 48 | 6630 | 6840 |
| 13 | UAUUAUUG-MGB AATAAAACC | 49 | 5090 | 5730 |
| 14 | UAUUAUUG-MGB AATAAGAACC | 50 | 5920 | 6520 |
| 15 | UAUUAUUG-MGB AATAACAACC | 51 | 4120 | 4530 |

$\Delta\Delta G$ was calculated at 37° C.

Example 10

This example illustrates the UV melting studies carried out using oligonucleotides of the present invention.

Hybrids formed between unmodified ODNs or MGB-probes and their complements were melted at a rate of 0.5° C./min, on a Lambda 2S (Perkin-Elmer) spectrophotometer with a PTP-6 automatic multicell temperature programmer. $T_m$ data was prepared using 0.5×SSPE buffer (Sigma, pH 7.4). Each ODN (1 µM of each strand) was mixed with its complement to give a 1:1 ratio. Prior to melting, samples were denatured at 100° C. and then cooled to 10° C. over a 10 min period. Mismatch discrimination for each type of duplex was calculated in terms of $\Delta\Delta G$ at 50° C. using the equation:

$$\Delta\Delta G°_{50} = R° \ln(K_{match}/K_{mismatch}).$$

The term $K_{match}/K_{mismatch}$ can be determined using the relative fractions of duplex and single strands calculated from the melting curves at 50° C. (see Lohkov, S. G. & Pyshnyi, *FEBS Letters* 420:134-138 (1997)).

Example 11

This example illustrates the hybridization of DNA to oligonucleotide glass microarrays prepared as described in co-pending application Ser. No. 09/364,320 and further optimized for 8-10 mer MGB probes.

DNA (oligonucleotide or PCR amplicon) at $1-5\times10^{-7}$ M in 5×SSPE, 0.1% Trition X-100, 10% formamide was hybridized to the microarray in Frame-Seal Chambers (MJ Research) under the following conditions: 5 minutes at 55° C., slow cooling at 0.1° C./sec to 35° C., 60 minutes at 55° C. The slides were then washed in 0.5×SSPE for 5 minutes at 45° C. Slides were dried under a stream of air and scanned using an Array Works Fluorescent scanner (Applied Precision). The washing procedure can be repeated under more stringent conditions if required.

Example 12

This example illustrates a single base primer extension assay.

Single stranded template DNA and 6-mer primer (20 µM each), 1× Thermopol buffer (New England Biolabs), 10 mM manganese chloride (USB), were combined and incubated 5 minutes at 50° C. Then 5 µCi $\alpha^{32}$P ddATP and 8 units Bst polymerase (NEB) were added, bringing total volume to 10 µl, and incubated 15 minutes at 50° C. After incubation, 6 µl stop solution (95% formamide, 20 mM EDTA) was added and reactions were cooled to room temperature. Samples were diluted 1:10 in denaturing dye (35% formamide, 0.05% xylene cyanol, 0.05% bromophenol blue, 1 mM EDTA), and aliquots were analyzed by electrophoresis on a denaturing 10% polyacrylamide gel.

The use of modified bases in primer extension assays for SNP typing is illustrated in Table 5. Primer extension with Bst polymerase (NEB) was evaluated with a primer substituted with different modified bases and the amount of product was measured based on the incorporated radioactivity using gel electrophoresis.

TABLE 5

Comparison of $^{32}$P-incorporation in primer extension product by polyacrylamide gel electrophoresis using AAC CAC TCT GTC CTA (SEQ ID NO: 52) template

| Primer | Relative Signal |
|---|---|
| TGAGAC | ++ |
| U$^{prop}$GAGAC | + |
| U$^{prop}$G$^{prop}$AGAC | +++ |
| U$^{prop}$G$^{prop}$A$^{prop}$GAC | +++++ |
| U$^{prop}$G$^{prop}$A$^{prop}$G$^{prop}$AC | +++++ |
| U$^{prop}$G$^{prop}$A$^{prop}$G$^{prop}$A$^{prop}$C | + |
| U$^{prop}$G$^{prop}$A$^{prop}$G$^{prop}$A$^{prop}$C$^{prop}$ | 0.5+ |

Example 13

This example illustrates the use of the algorithm described in the specification to predict the $T_m$ of modified oligonucleotides containing PPG both with and without a minor groove binder (CDPI$_3$).

Using thermodynamic parameters in Tables 2a/2b and the correction formula for the MGBs contribution, $T_m$ of PPG oligonucleotides with and without a MGB can be calculated with algorithm procedures as described above. The thermodynamic parameters of the nearest neighbor pairs that are not G-containing do not change when the oligonucleotides are substituted with PPG. Similarly the thermodynamic parameters of the nearest-neighbor pairs do not change when MGB containing oligonucleotides are substituted with PPG. Table 6 illustrates the ability of the algorithm to predict the $T_m$ of oligonucleotides containing PPG alone or in combination with a minor groove binder (CDPI$_3$). In Table 6, all Gs are substituted with PPGs.

TABLE 6

Comparison of experimental $T_m$S with that of predicted $T_m$s using the nearest-neighbor thermodynamic parameters for PPG containing oligonucleotides and PPG containing oligonucleotides attached to a MGB

| 5'-Probe Sequence-3' | SEQ ID NO: | ODN Duplex Stability ° C. | | | MGB-ODN Duplex Stability ° C. | | |
|---|---|---|---|---|---|---|---|
| | | $Tm_{exp}$ | $Tm_{calc}$ | Err | $Tm_{exp}$ | $Tm_{calc}$ | Err |
| CTGTAAGTAGATATAAC | 53 | 51.84 | 53.23 | 1.39 | 65.88 | 66.69 | 0.81 |
| GGCAAGATATATAG | 54 | 50.21 | 49.81 | -0.40 | 66.37 | 65.56 | -0.81 |
| GTGACGCAGATTCC | 55 | 61.27 | 61.06 | -0.21 | 76.97 | 75.19 | -1.78 |
| GTAAGTAGACATAAC | 56 | 52.12 | 51.78 | -0.34 | 64.64 | 63.31 | -1.33 |
| CAGGGAGCTTTGGA | 57 | 59.9 | 60.22 | 0.32 | 74.39 | 71.47 | -2.92 |
| CACTCGTGAAGCTG | 58 | 60.85 | 59.49 | -1.36 | 74.04 | 72.26 | -1.78 |
| GTAAGTAGGCATAAC | 59 | 55.74 | 55.47 | -0.27 | 66.91 | 66.00 | -0.91 |
| CCGGATGTAGGATC | 60 | 57.52 | 59.05 | 1.53 | 69.3 | 70.03 | 0.73 |
| GATTACCTGGATTT | 61 | 50.64 | 50.32 | -0.32 | 62.29 | 62.33 | 0.04 |
| CCGTCAATGGTCAC | 62 | 58.66 | 60.01 | 1.35 | 70.13 | 69.91 | -0.22 |
| CAGCACGTAGCC | 63 | 57.31 | 58.07 | 0.76 | 69.29 | 67.60 | -1.69 |
| CGGCTACGTGCTGG | 64 | 65.19 | 66.01 | 0.82 | 76.12 | 74.79 | -1.33 |
| CGGCTACATGCTGG | 65 | 61.14 | 61.95 | 0.81 | 71.56 | 72.99 | 1.43 |
| CTAAATCTGCCG | 66 | 50.4 | 48.09 | -2.31 | 62.08 | 60.19 | -1.89 |
| TCTGGATGATGGGCA | 67 | 61.74 | 61.95 | 0.21 | 71.65 | 72.13 | 0.48 |
| GTTCATGGGTGTAAT | 68 | 57.51 | 57.77 | 0.26 | 66.94 | 68.79 | 1.85 |
| CGGAGGTAGGATCA | 69 | 59.24 | 59.46 | 0.22 | 69.46 | 70.93 | 1.47 |

TABLE 6-continued

Comparison of experimental $T_m$s with that of predicted $T_m$s using the nearest-neighbor thermodynamic parameters for PPG containing oligonucleotides and PPG containing oligonucleotides attached to a MGB

| 5'-Probe Sequence-3' | SEQ ID NO: | ODN Duplex Stability ° C. | | | MGB-ODN Duplex Stability ° C. | | |
|---|---|---|---|---|---|---|---|
| | | $Tm_{exp}$ | $Tm_{calc}$ | Err | $Tm_{exp}$ | $Tm_{calc}$ | Err |
| CCACCCGCCTCAG | 70 | 60.73 | 61.14 | 0.41 | 71.43 | 70.74 | -0.69 |
| CACAGGAGTGGTTGG | 71 | 63.07 | 64.40 | 1.33 | 72.28 | 72.92 | 0.64 |
| CGGACCAGTGCGTG | 72 | 68.1 | 67.58 | -0.52 | 77.92 | 76.80 | -1.12 |
| TCGGACCAGTGCGT | 73 | 65.04 | 66.00 | 0.96 | 74.94 | 75.62 | 0.68 |
| AACGGGTACGATA | 74 | 57.93 | 57.11 | -0.82 | 67.79 | 67.08 | -0.71 |
| CAGTTGAGATTCTAAGAC | 75 | 60.06 | 60.15 | 0.09 | 67.15 | 67.43 | 0.28 |
| AGGGGCGTCTTG | 76 | 60.78 | 58.57 | -2.21 | 71.62 | 72.76 | 1.14 |
| GTAAGTAGGCATAGC | 77 | 58.34 | 58.95 | 0.61 | 65.95 | 66.99 | 1.04 |
| TGCCCAGCCCCAG | 78 | 63.13 | 63.40 | 0.27 | 71.28 | 71.32 | 0.04 |
| CCAACACTCGTGAA | 79 | 54.87 | 56.14 | 1.27 | 62.07 | 63.54 | 1.47 |
| GTAAGTAGACACAGC | 80 | 59.48 | 58.41 | -1.07 | 65.79 | 66.27 | 0.48 |
| TCGGACCAGTGC | 81 | 58.02 | 58.55 | 0.53 | 65.99 | 66.35 | 0.36 |
| CGATCACGCTGGC | 82 | 62.12 | 62.75 | 0.63 | 69.18 | 71.81 | 2.63 |
| GTCCTGGGGGTGG | 83 | 65.19 | 64.54 | -0.65 | 72.78 | 72.53 | -0.25 |
| GTAAGTAGGTGTGAC | 84 | 60.7 | 59.70 | -1.00 | 66.92 | 67.00 | 0.08 |
| GGTTGTACGGGTTCACG | 85 | 68.38 | 68.81 | 0.43 | 74.16 | 75.38 | 1.22 |
| CGACCAGTCCGTGA | 86 | 66.84 | 65.46 | -1.38 | 73.38 | 71.53 | -1.85 |
| GTAAGTAGACGCAGC | 87 | 62.91 | 62.44 | -0.47 | 68 | 67.82 | -0.18 |
| GTAAGTAGGCGCAGC | 88 | 65.52 | 65.91 | 0.39 | 69.8 | 70.34 | 0.54 |
| GTAAGTAGGCGCGGC | 89 | 68.71 | 68.96 | 0.25 | 72.26 | 72.76 | 0.50 |
| GGTTCCCGAGCG | 90 | 62.15 | 61.14 | -1.01 | 65.75 | 64.22 | -1.53 |

The accuracy of the prediction algorithm is about +/-1 and +/-2° C. for PPG containing oligonucleotides and PPG containing MGB-oligonucleotides, respectively. Accordingly, a sequence of interest can be obtained from a source such as GENBANK, and a $T_m$ window can then be set as a requirement for a set of probes or primers. Using the algorithm above, and information from the nearest-neighbor parameters, a collection of probe or primer sequences with the desired $T_m$s can be calculated.

Alternatively, the algorithm can be used to select nearest-neighbor parameters from a selection of modified bases and to calculate the stability of more than one sequence of the same length to give the same predetermined thermodynamic stability, with the selected modified bases.

Still further, the algorithm can be used to select one or more modified bases that allow the design of oligonucleotides of the same base pair length and substantially the same stability ($T_m$). These modified bases can be selected from a database containing predetermined thermodynamic nearest neighbor parameters from an collection of modified purines and/or modified pyrimidines. Preferably, the database contains nearest-neighbor parameters of 3-substituted pyrazolo[3,4-d]pyrimidines and/or 5-substituted pyrimidines.

Example 14

This example illustrates the use of modified oligonucleotides in an Invader™ assay.

Figure 4:
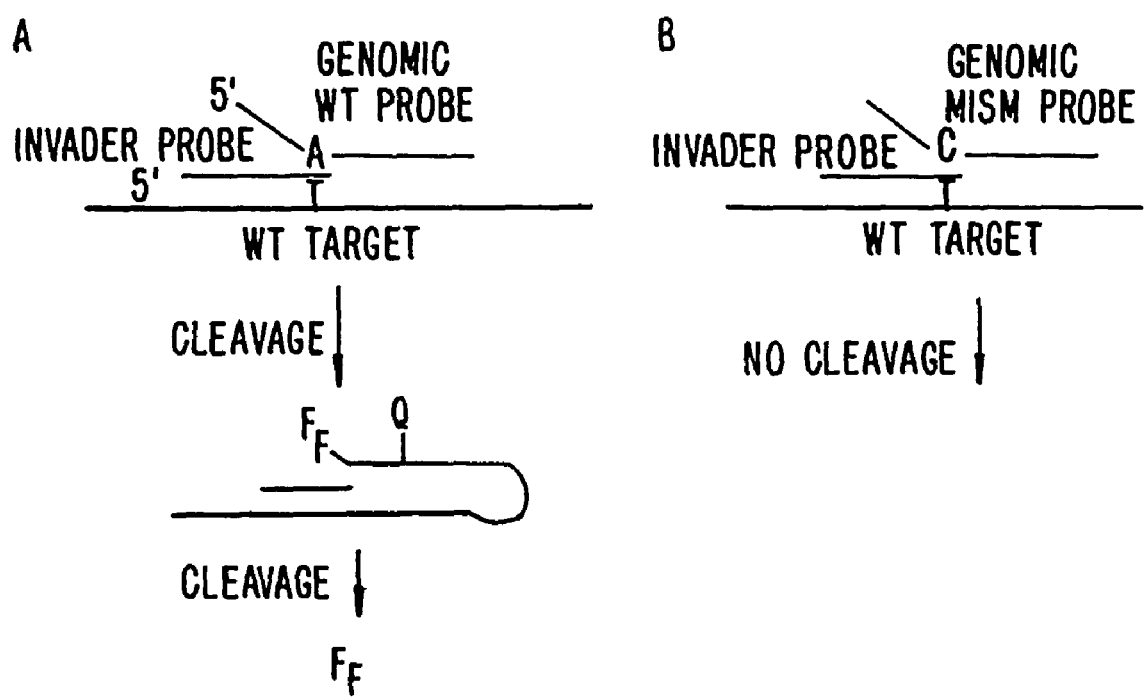
FIG. 4 illustrates an Invader™ assay in which the modified oligonucleotides of the invention can be used.
Figure 5:
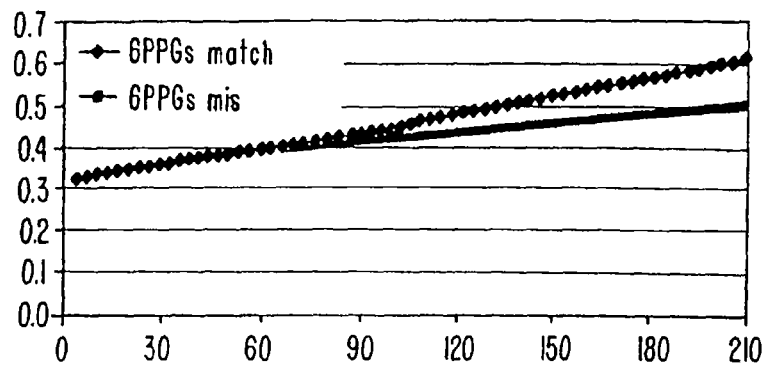
FIG. 5 illustrates a comparison of Invader™ probe performance with different numbers of PPGs (SEQ ID NOS:5-7).
Figure 5:
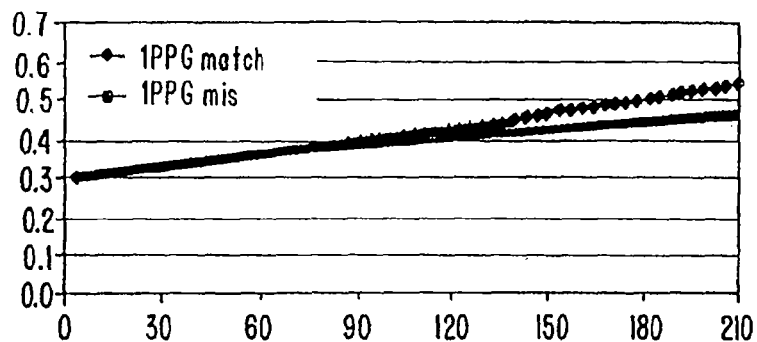
Figure 5:
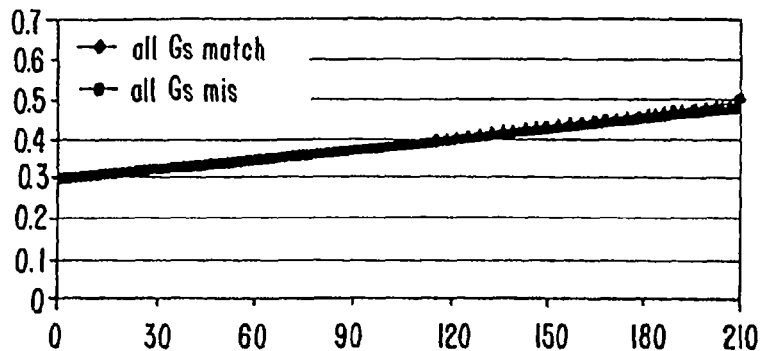

The cleavase-based assay is shown in FIG. 4 detects specific DNA and RNA sequences to cleave a complex formed by the hybridization of two overlapping oligonucleotides to a target. The enzyme cleaves the overhanging "flap", which serves as an invader probe in the detection cassette probe where cleavage releases a fluorescence signal. The first cleavage takes places only when the single base mismatch in the invader is a perfect match. No reaction takes place with a mismatch target B. The cleaved "flap" serves as an invader in the detection cassette, leading to the release of fluorescence in the second cleavage step.

Table 7a and 7b

Comparison of Cleavase-Bases Amplification System with Different Modified Bases Substituted in the Genomic and Invader Probes

TABLE 7a

| # | Probe[1] | Modified Bases Substituted in Probe Sequence[2] | Length |
|---|---|---|---|
| 1 | Cassette | None | 41 |
| 2 | Invader T | None | 59 |
| 3 | Invader M1 | Five A24 bases | 32 |
| 4 | Genomic T | None | 43 |
| 5 | Genomic M1 | Six A14 bases | 35 |
| 6 | Genomic M2 | Five A24 bases | 31 |

[1]Unmodified Probes and assay conditions are similar to those described by Hall et al, PNAS 97: 8272-77 (2000)
[2]A14 is hydroxypropynylPPA and A24 is 3-iododiaminoPPA

TABLE 7b

| Genomic probe | Endpoint Match/Mismatch Signal Ratio | ΔF RFU[3] |
|---|---|---|
| 4 | 5 | 4100 |
| 5 | 10 | 8000 |
| 6 | 7 | 11900 |

[3]ΔF is end point fluorescence difference between match and mismatch in relative fluorescence units Table 7a shows a comparison of the effect of different modified bases when substituted in the Invader and genomic probes. The traditional invaderT (2) was substituted with 3-iododiaminoPPPA to give invader M1 which now has a length of 32 with a similar $T_m$ as the 59-mer (2). Similarly the traditional genomic probe (4) was substituted 3-hydroxypropynylPPPA and 3-iododiaminoPPPA to give (5) and (6) respectively. Both of these probes are substantially shorter than the traditional (4). Using invaderM1 (3) in combination with the genomic probes 4-6 individually results in (Table 7b) improved performance of both genomic probes containing the modified bases (5 and 6) compared to the traditional genomic probe (4). As shown both the endpoint match/mismatch signal ratios and the end point fluorescence show increases compared to the unmodified genomic probe.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A method for designing a preferred oligonucleotide sequence having a selected duplex stability comprising:
   a) providing an oligonucleotide sequence having N bases and N−1 neighboring base pairs,
   b) modifying the oligonucleotide sequence to provide modified oligonucleotide sequences wherein said modified oligonucleotide sequences comprise at least one modified base selected from the group consisting of unsubstituted pyrazolo[3,4-d]pyrimidines, 3-substituted pyrazolo[3,4-d]pyrimidines, and 5-substituted pyrimidines;
   c) calculating the duplex stabilities of said modified oligonucleotide sequences using an algorithm applying a nearest-neighbor model for duplex formation thermodynamics for each of the N−1 neighboring base pairs, each nearest neighbor thermodynamic parameter defining a thermodynamic contribution of two corresponding neighboring bases;
   d) selecting a preferred oligonucleotide sequence from the modified oligonucleotide sequences having a selected duplex stability; and
   e) creating an oligonucleotide comprising the preferred oligonucleotide sequence.

2. A method for designing a preferred oligonucleotide sequence having a selected duplex stability comprising:
   a) providing an oligonucleotide sequence having N bases and N−1 neighboring base pairs,
   b) modifying the oligonucleotide sequence to provide modified oligonucleotide sequences wherein said modified oligonucleotide sequences comprises comprise at least one modified base selected from the group consisting of unsubstituted pyrazolo[3,4-d]pyrimidines, 3-substituted pyrazolo[3,4-d]pyrimidines, and 5-substituted pyrimidines, and a minor groove binder;
   c) calculating a melting temperature ($T_m$) of said modified oligonucleotide sequences using an algorithm applying nearest neighbor thermodynamic parameters for each of the N−1 neighboring base pairs, each nearest neighbor thermodynamic parameter defining a thermodynamic contribution of two corresponding neighboring bases;
   d) selecting a preferred oligonucleotide sequence from the modified oligonucleotide sequences having the selected melting temperature; and
   e) creating an oligonucleotide comprising the preferred oligonucleotide sequence.

3. The method of any one of claim 1 or 2, wherein said oligonucleotide sequence is derived from a database source.

4. The method of claim 3, wherein said database source is GENBANK.

5. The method of any one of claim 1 or 2, wherein said at least one modified base is a member selected from the group consisting of a base attached to an amino acid, a polyamide nucleic acid (PNA), and a locked nucleic acid sugar.

6. The method of claim 5, wherein said modified base is attached to PNA.

7. The method of claim 5, wherein said modified base is attached to a locked nucleic acid sugar.

8. The method of any one of claim 1 or 2, wherein said oligonucleotide has an enhanced ability of mismatch discrimination, in comparison to unmodified nucleotides.

9. The method of any one of claims 1 or 2, wherein said at least one modified base is a member selected from the group consisting of PPA, PPG, PPPA, PPPG, PU, PC, HOPU, HOBuU, HOBuC, $(NH_2)_2$PPPA, $(NH_2)_2$PPPAOH, $(NH_2)_2$BuPPAOH, $(NH_2)_2$PPAI, and HOBuPPG.

10. The method of claim 1, wherein said oligonucleotide has attached to it one or more members selected from the group consisting of a minor groove binder, a fluorophore, and a quencher.

11. The method of claim 10, wherein said oligonucleotide has a minor groove binder attached thereto.

12. The method of claim 2 or 11, wherein said minor groove binder has a formula selected from the group consisting of:

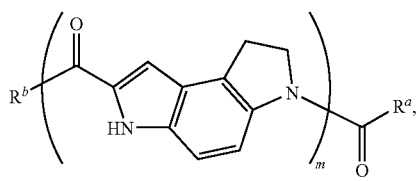

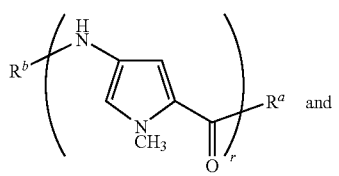 and

-continued

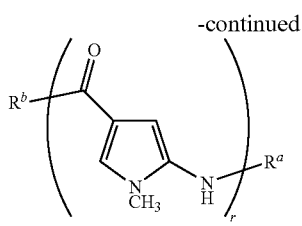

wherein
the subscript m is an integer of from 2 to 5;
the subscript r is an integer of from 2 to 10; and
each $R^a$ and $R^b$ is independently a linking group to said modified oligonucleotide, H, $OR^c$, $NR^cR^d$, $COOR^c$, or —$CONR^cR^d$ wherein each $R^c$ and $R^d$ is selected from the group consisting of H, ($C_1$-$C_{12}$)heteroalkyl, ($C_2$-$C_{12}$)heteroalkenyl, ($C_2$-$C_{12}$)heteroalkynyl, ($C_1$-$C_{12}$)alkyl, ($C_2$-$C_{12}$)alkenyl, ($C_2$-$C_{12}$)alkynyl, aryl($C_1$-$C_{12}$)alkyl, and aryl.

13. The method of claim 11, wherein said minor groove binder is attached to the oligonucleotide via a quencher molecule.

14. The method of any one of claim 1 or 2, wherein said algorithm predicts the melting temperature ($T_m$) of said oligonucleotide with an accuracy of about +/−2° C.

15. The method of any one of claim 1 or 2, wherein said method is applied to establish appropriate conditions for hybridization, renaturation, mapping variations of base compositions of sequences, or determination of sequence complexity and divergence.

16. The method of any one of claim 1 or 2, wherein said oligonucleotide is a capture probe in an array.

17. The method of claim 6, wherein said oligonucleotide has an enhanced ability of mismatch discrimination, in comparison to unmodified nucleotides.

18. The method of claim 7, wherein said oligonucleotide has an enhanced ability of mismatch discrimination, in comparison to unmodified nucleotides.

19. The method of claim 1, wherein the oligonucleotide sequence comprises a universal base and wherein the modified oligonucleotide sequences comprise the universal base and at least one modified base selected from the group consisting of unsubstituted pyrazolo[3,4-d]pyrimidines, 3-substituted pyrazolo[3,4-d]pyrimidines, and 5-substituted pyrimidines.

20. The method of claim 2, wherein the oligonucleotide sequence comprises a universal base and wherein the modified oligonucleotide sequences comprise the universal base and at least one modified base selected from the group consisting of unsubstituted pyrazolo[3,4-d]pyrimidines, 3-substituted pyrazolo[3,4-d]pyrimidines, and 5-substituted pyrimidines.

* * * * *

SEQUENCE LISTING

<160> NUMBER OF SEQ ID NOS: 90

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:minor groove
      binder (MGB)-modified FAM probe
<220> FEATURE:
<221> NAME/KEY: modified_base
<222> LOCATION: (1)
<223> OTHER INFORMATION: n = c modified by FAM
<220> FEATURE:
<221> NAME/KEY: modified_base
<222> LOCATION: (18)
<223> OTHER INFORMATION: n = t modified by a quencher (Q) and minor
      groove binder (MGB)

<400> SEQUENCE: 1
nttttgacct aacaaatn                                                 18

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence:minor groove
      binder (MGB)-modified FAM probe complement

<400> SEQUENCE: 2
atgttaattt gttaggtcaa aagaaaaatc tttaga                             36

```
<210> SEQ ID NO 3
<211> LENGTH: 36
<212> TYPE: DNA
<213> ORGANISM: Artificial Sequence
<220> FEATURE:
<223> OTHER INFORMATION: Description of Artificial
      Sequence:4-amino-3-(prop-1-ynyl)pyrazolo[3,4-d]pyrimidine
      (PPPA) analog of adenosine and pyrazolo[3,4-d]pyrimidine
      analog of guanosine (PPG) containing minor groove binder
      (MGB)-modified FAM probe

<400> SEQUENCE: 3
tacaattaaa caatccagtt ttcttttag aaatct                              36

<210> SEQ ID NO 4
<211> LENGTH: 15
<212> TYPE: DNA
<213> ORGANISM: Artificial Sequence
<220> FEATURE:
<223> OTHER INFORMATION: Description of Artificial
      Sequence:4-amino-3-(prop-1-ynyl)pyrazolo[3,4-d]pyrimidine
      (PPPA) analog of adenosine and pyrazolo[3,4-d]pyrimidine
      guanosine (PPG) containing minor groove binder
      (MGB)-modified FAM probe complement
<220> FEATURE:
<221> NAME/KEY: modified_base
<222> LOCATION: (1)
<223> OTHER INFORMATION: n = pyrazolo[3,4-d]pyrimidine analog of
      guanosine modified by FAM
<220> FEATURE:
<221> NAME/KEY: modified_base
<222> LOCATION: (5)..(6)
<223> OTHER INFORMATION: n = pyrazolo[3,4-d]pyrimidine analog of
      guanosine
<220> FEATURE:
<221> NAME/KEY: modified_base
<222> LOCATION: (9)..(11)
<223> OTHER INFORMATION: n =
      4-amino-3-(prop-1-ynyl)pyrazolo[3,4-d]pyrimidine
      analog of adenosine
<220> FEATURE:
<221> NAME/KEY: modified_base
<222> LOCATION: (15)
<223> OTHER INFORMATION: n = a modified by a quencher (Q) and minor
      groove binder (MGB)

<400> SEQUENCE: 4
nttanntcnn nagan                                                    15

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:TM-Invader
      probe substituted with six
      pyrazolo[3,4-d]pyrimidine analogs of guanosine
<220> FEATURE:
<221> NAME/KEY: modified_base
<222> LOCATION: (2)..(7)
<223> OTHER INFORMATION: n = pyrazolo[3,4-d]pyrimidine analog of
      guanosine

<400> SEQUENCE: 5
tnnnnnncct tggcggctac g                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:TM-Invader
```

```
        probe substituted with one
        pyrazolo[3,4-d]pyrimidine analog of guanosine:
<220> FEATURE:
<221> NAME/KEY: modified_base
<222> LOCATION: (5)
<223> OTHER INFORMATION: n = pyrazolo[3,4-d]pyrimidine analog of
        guanosine

<400> SEQUENCE: 6
tgggnggcct tggcggctac g                                                  21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:TM-Invader
        probe

<400> SEQUENCE: 7 tgggggcct tggcggctac g                                                   21

<210> SEQ ID NO 8
<211> LENGTH: 10
<212> TYPE: DNA
<213> ORGANISM: Artificial Sequence
<220> FEATURE:
<223> OTHER INFORMATION: Description of Artificial
        Sequence:complementary target 1

<400> SEQUENCE: 8
tcggcggcgt                                                               10

<210> SEQ ID NO 9
<211> LENGTH: 10
<212> TYPE: DNA
<213> ORGANISM: Artificial Sequence
<220> FEATURE:
<223> OTHER INFORMATION: Description of Artificial
        Sequence:complementary target 2

<400> SEQUENCE: 9
acagcggcgt                                                               10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial
        Sequence:complementary target 3

<400> SEQUENCE: 10
acagcgacgt                                                               10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial
        Sequence:complementary target 4

<400> SEQUENCE: 11
tcagtgacga                                                               10

<210> SEQ ID NO 12
```

```
<211> LENGTH: 10
<212> TYPE: DNA
<213> ORGANISM: Artificial Sequence
<220> FEATURE:
<223> OTHER INFORMATION: Description of Artificial
      Sequence:complementary target 5

<400> SEQUENCE: 12
tcagtgacaa                                                          10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial
      Sequence:complementary target 6

<400> SEQUENCE: 13
tcaatgacag                                                          10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial
      Sequence:complementary target 7

<400> SEQUENCE: 14
acaatgataa                                                          10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial
      Sequence:complementary target 8

<400> SEQUENCE: 15
ccaataataa                                                          10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial
      Sequence:complementary target 9

<400> SEQUENCE: 16
gtaataataa                                                          10

<210> SEQ ID NO 17
<211> LENGTH: 23
<212> TYPE: DNA
<213> ORGANISM: Artificial Sequence
<220> FEATURE:
<223> OTHER INFORMATION: Description of Artificial
      Sequence:probe sequence 1

<400> SEQUENCE: 17
aaagttatgt ctacttacag aaa                                           23

<210> SEQ ID NO 18
<211> LENGTH: 23
```

```
<212> TYPE: DNA
<213> ORGANISM: Artificial Sequence
<220> FEATURE:
<223> OTHER INFORMATION: Description of Artificial
      Sequence:probe sequence 2

<400> SEQUENCE: 18
aaagctatgt ctacttacag aaa                                            23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial
      Sequence:probe sequence 3

<400> SEQUENCE: 19
aaagtcatgt ctacttacag aaa                                            23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial
      Sequence:probe sequence 4

<400> SEQUENCE: 20
aaagttgtgt ctacttacag aaa                                            23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial
      Sequence:probe sequence 5

<400> SEQUENCE: 21
aaagttacgt ctacttacag aaa                                            23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial
      Sequence:probe sequence 6

<400> SEQUENCE: 22
aaagttatat ctacttacag aaa                                            23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial
      Sequence:probe sequence 7

<400> SEQUENCE: 23
aaagttatgc ctacttacag aaa                                            23

<210> SEQ ID NO 24
<211> LENGTH: 23
<212> TYPE: DNA
```

-continued

```
<213> ORGANISM: Artificial Sequence
<220> FEATURE:
<223> OTHER INFORMATION: Description of Artificial
      Sequence:probe sequence 8

<400> SEQUENCE: 24
aaagttatgt ttacttacag aaa                                           23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial
      Sequence:probe sequence 9

<400> SEQUENCE: 25
aaagttatgt ccacttacag aaa                                           23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial
      Sequence:probe sequence 10

<400> SEQUENCE: 26
aaagttatgt ctgcttacag aaa                                           23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial
      Sequence:probe sequence 11

<400> SEQUENCE: 27
aaagttatgt ctatttacag aaa                                           23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial
      Sequence:probe sequence 12

<400> SEQUENCE: 28
aaagttatgt ctacctacag aaa                                           23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial
      Sequence:probe sequence 13

<400> SEQUENCE: 29
aaagttatgt ctactcacag aaa                                           23

<210> SEQ ID NO 30
<211> LENGTH: 23
<212> TYPE: DNA
<213> ORGANISM: Artificial Sequence
```

-continued

```
<220> FEATURE:
<223> OTHER INFORMATION: Description of Artificial
      Sequence:probe sequence 14

<400> SEQUENCE: 30
aaagttatgt ctacttgcag aaa                                              23

<210> SEQ ID NO 31
<211> LENGTH: 15
<212> TYPE: DNA
<213> ORGANISM: Artificial Sequence
<220> FEATURE:
<223> OTHER INFORMATION: Description of Artificial
      Sequence:target sequence 1

<400> SEQUENCE: 31
gtaagtagac ataac                                                       15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial
      Sequence:target sequence 2
<220> FEATURE:
<221> NAME/KEY: modified_base
<222> LOCATION: (1)..(15)
<223> OTHER INFORMATION: n = 4-amino-3-(prop-1-ynyl)pyrazolo[3,4-
      d]pyrimidine analog of adenosine

<400> SEQUENCE: 32
gtnngtngnc ntnnc                                                       15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial
      Sequence:target sequence 3
<220> FEATURE:
<221> NAME/KEY: modified_base
<222> LOCATION: (15)
<223> OTHER INFORMATION: n = c modified by minor groove binder (MGB)

<400> SEQUENCE: 33
gtaagtagac ataan                                                       15

<210> SEQ ID NO 34
<211> LENGTH: 15
<212> TYPE: DNA
<213> ORGANISM: Artificial Sequence
<220> FEATURE:
<223> OTHER INFORMATION: Description of Artificial
      Sequence:target sequence 4
<220> FEATURE:
<221> NAME/KEY: modified_base
<222> LOCATION: (1)..(14)
<223> OTHER INFORMATION: n = 4-amino-3-(prop-1-ynyl)pyrazolo[3,4-
      d]pyrimidine analog of adenosine
<220> FEATURE:
<221> NAME/KEY: modified_base
<222> LOCATION: (15)
<223> OTHER INFORMATION: n = c modified by minor groove binder (MGB)

<400> SEQUENCE: 34
gtnngtngnc ntnnn                                                       15
```

```
<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence:duplex
      complement match

<400> SEQUENCE: 35
agctgtgact                                                                 10

<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence:duplex
      complement 1

<400> SEQUENCE: 36
agctgtgact                                                                 10

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence:duplex
      complement 2

<400> SEQUENCE: 37
agcggtgact                                                                 10

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence:duplex
      complement 3

<400> SEQUENCE: 38
agccgtgact                                                                 10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence:duplex
      complement 4

<400> SEQUENCE: 39
agcagagact                                                                 10

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence:duplex
      complement 5

<400> SEQUENCE: 40
agcagggact                                                                 10

<210> SEQ ID NO 41
```

```
<211> LENGTH: 10
<212> TYPE: DNA
<213> ORGANISM: Artificial Sequence
<220> FEATURE:
<223> OTHER INFORMATION: Description of Artificial Sequence:duplex
      complement 6

<400> SEQUENCE: 41
agcagcgact                                                              10

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence:duplex
      complement 7

<400> SEQUENCE: 42
agcaatgact                                                              10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence:duplex
      complement 8

<400> SEQUENCE: 43
agcattgact                                                              10

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence:duplex
      complement 9

<400> SEQUENCE: 44
agcactgact                                                              10

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence:duplex
      complement match

<400> SEQUENCE: 45
aataataacc                                                              10

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence:duplex
      complement 10

<400> SEQUENCE: 46
aattataacc                                                              10

<210> SEQ ID NO 47
<211> LENGTH: 10
```

```
<212> TYPE: DNA
<213> ORGANISM: Artificial Sequence
<220> FEATURE:
<223> OTHER INFORMATION: Description of Artificial Sequence:duplex
      complement 11

<400> SEQUENCE: 47
aatgataacc                                                              10

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence:duplex
      complement 12

<400> SEQUENCE: 48
aatcataacc                                                              10

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence:duplex
      complement 13

<400> SEQUENCE: 49
aataaaaacc                                                              10

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence:duplex
      complement 14

<400> SEQUENCE: 50
aataagaacc                                                              10

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence:duplex
      complement 15

<400> SEQUENCE: 51
aataacaacc                                                              10

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence:primer
      extension template

<400> SEQUENCE: 52
aaccactctg tccta                                                        15

<210> SEQ ID NO 53
<211> LENGTH: 17
<212> TYPE: DNA
```

```
<213> ORGANISM: Artificial Sequence
<220> FEATURE:
<223> OTHER INFORMATION: Description of Artificial
      Sequence:probe sequence

<400> SEQUENCE: 53
ctgtaagtag atataac                                               17

<210> SEQ ID NO 54
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 54
ggcaagatat atag                                                  14

<210> SEQ ID NO 55
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 55
gtgacgcaga ttcc                                                  14

<210> SEQ ID NO 56
<211> LENGTH: 15
<212> TYPE: DNA
<213> ORGANISM: Artificial Sequence
<220> FEATURE:
<223> OTHER INFORMATION: Description of Artificial
      Sequence:probe sequence

<400> SEQUENCE: 56
gtaagtagac ataac                                                 15

<210> SEQ ID NO 57
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 57
cagggagctt tgga                                                  14

<210> SEQ ID NO 58
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 58
cactcgtgaa gctg                                                  14

<210> SEQ ID NO 59
<211> LENGTH: 15
<212> TYPE: DNA
<213> ORGANISM: Artificial Sequence
```

-continued

```
<220> FEATURE:
<223> OTHER INFORMATION: Description of Artificial
      Sequence:probe sequence

<400> SEQUENCE: 59
gtaagtaggc ataac                                                      15

<210> SEQ ID NO 60
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 60
ccggatgtag gatc                                                       14

<210> SEQ ID NO 61
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 61
gattacctgg attt                                                       14

<210> SEQ ID NO 62
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 62
ccgtcaatgg tcac                                                       14

<210> SEQ ID NO 63
<211> LENGTH: 12
<212> TYPE: DNA
<213> ORGANISM: Artificial Sequence
<220> FEATURE:
<223> OTHER INFORMATION: Description of Artificial
      Sequence:probe sequence

<400> SEQUENCE: 63
cagcacgtag cc                                                         12

<210> SEQ ID NO 64
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 64
cggctacgtg ctgg                                                       14

<210> SEQ ID NO 65
<211> LENGTH: 14
<212> TYPE: DNA
<213> ORGANISM: Artificial Sequence
<220> FEATURE:
```

```
<223> OTHER INFORMATION: Description of Artificial
      Sequence:probe sequence

<400> SEQUENCE: 65
cggctacatg ctgg                                                       14

<210> SEQ ID NO 66
<211> LENGTH: 12
<212> TYPE: DNA
<213> ORGANISM: Artificial Sequence
<220> FEATURE:
<223> OTHER INFORMATION: Description of Artificial
      Sequence:probe sequence

<400> SEQUENCE: 66
ctaaatctgc cg                                                         12

<210> SEQ ID NO 67
<211> LENGTH: 15
<212> TYPE: DNA
<213> ORGANISM: Artificial Sequence
<220> FEATURE:
<223> OTHER INFORMATION: Description of Artificial
      Sequence:probe sequence

<400> SEQUENCE: 67
tctggatgat gggca                                                      15

<210> SEQ ID NO 68
<211> LENGTH: 15
<212> TYPE: DNA
<213> ORGANISM: Artificial Sequence
<220> FEATURE:
<223> OTHER INFORMATION: Description of Artificial
      Sequence:probe sequence

<400> SEQUENCE: 68
gttcatgggt gtaat                                                      15

<210> SEQ ID NO 69
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 69
cggaggtagg atca                                                       14

<210> SEQ ID NO 70
<211> LENGTH: 13
<212> TYPE: DNA
<213> ORGANISM: Artificial Sequence
<220> FEATURE:
<223> OTHER INFORMATION: Description of Artificial
      Sequence:probe sequence

<400> SEQUENCE: 70
ccacccgcct cag                                                        13

<210> SEQ ID NO 71
<211> LENGTH: 15
<212> TYPE: DNA
<213> ORGANISM: Artificial Sequence
<220> FEATURE:
<223> OTHER INFORMATION: Description of Artificial
```

-continued

Sequence:probe sequence

<400> SEQUENCE: 71
cacaggagtg gttgg     15

<210> SEQ ID NO 72
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 72
cggaccagtg cgtg     14

<210> SEQ ID NO 73
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 73
tcggaccagt gcgt     14

<210> SEQ ID NO 74
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 74
aacggggtac gata     14

<210> SEQ ID NO 75
<211> LENGTH: 18
<212> TYPE: DNA
<213> ORGANISM: Artificial Sequence
<220> FEATURE:
<223> OTHER INFORMATION: Description of Artificial
      Sequence:probe sequence

<400> SEQUENCE: 75
cagttgagat tctaagac     18

<210> SEQ ID NO 76
<211> LENGTH: 12
<212> TYPE: DNA
<213> ORGANISM: Artificial Sequence
<220> FEATURE:
<223> OTHER INFORMATION: Description of Artificial
      Sequence:probe sequence

<400> SEQUENCE: 76
aggggcgtct tg     12

<210> SEQ ID NO 77
<211> LENGTH: 15
<212> TYPE: DNA
<213> ORGANISM: Artificial Sequence
<220> FEATURE:
<223> OTHER INFORMATION: Description of Artificial
      Sequence:probe sequence

```
<400> SEQUENCE: 77
gtaagtaggc atagc                                                          15

<210> SEQ ID NO 78
<211> LENGTH: 13
<212> TYPE: DNA
<213> ORGANISM: Artificial Sequence
<220> FEATURE:
<223> OTHER INFORMATION: Description of Artificial
      Sequence:probe sequence

<400> SEQUENCE: 78
tgcccagccc cag                                                            13

<210> SEQ ID NO 79
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 79
ccaacactcg tgaa                                                           14

<210> SEQ ID NO 80
<211> LENGTH: 15
<212> TYPE: DNA
<213> ORGANISM: Artificial Sequence
<220> FEATURE:
<223> OTHER INFORMATION: Description of Artificial
      Sequence:probe sequence

<400> SEQUENCE: 80
gtaagtagac acagc                                                          15

<210> SEQ ID NO 81
<211> LENGTH: 12
<212> TYPE: DNA
<213> ORGANISM: Artificial Sequence
<220> FEATURE:
<223> OTHER INFORMATION: Description of Artificial
      Sequence:probe sequence

<400> SEQUENCE: 81
tcggaccagt gc                                                             12

<210> SEQ ID NO 82
<211> LENGTH: 13
<212> TYPE: DNA
<213> ORGANISM: Artificial Sequence
<220> FEATURE:
<223> OTHER INFORMATION: Description of Artificial
      Sequence:probe sequence

<400> SEQUENCE: 82
cgatcacgct ggc                                                            13

<210> SEQ ID NO 83
<211> LENGTH: 13
<212> TYPE: DNA
<213> ORGANISM: Artificial Sequence
<220> FEATURE:
<223> OTHER INFORMATION: Description of Artificial
      Sequence:probe sequence
```

-continued

<400> SEQUENCE: 83 gtcctgggggg tgg                                                         13

<210> SEQ ID NO 84
<211> LENGTH: 15
<212> TYPE: DNA
<213> ORGANISM: Artificial Sequence
<220> FEATURE:
<223> OTHER INFORMATION: Description of Artificial
      Sequence:probe sequence

<400> SEQUENCE: 84
gtaagtaggt gtgac                                                        15

<210> SEQ ID NO 85
<211> LENGTH: 17
<212> TYPE: DNA
<213> ORGANISM: Artificial Sequence
<220> FEATURE:
<223> OTHER INFORMATION: Description of Artificial
      Sequence:probe sequence

<400> SEQUENCE: 85
ggttgtacgg gttcacg                                                      17

<210> SEQ ID NO 86
<211> LENGTH: 14
<212> TYPE: DNA
<213> ORGANISM: Artificial Sequence
<220> FEATURE:
<223> OTHER INFORMATION: Description of Artificial
      Sequence:probe sequence

<400> SEQUENCE: 86
ggaccagtgc gtga                                                         14

<210> SEQ ID NO 87
<211> LENGTH: 15
<212> TYPE: DNA
<213> ORGANISM: Artificial Sequence
<220> FEATURE:
<223> OTHER INFORMATION: Description of Artificial
      Sequence:probe sequence

<400> SEQUENCE: 87
gtaagtagac gcagc                                                        15

<210> SEQ ID NO 88
<211> LENGTH: 15
<212> TYPE: DNA
<213> ORGANISM: Artificial Sequence
<220> FEATURE:
<223> OTHER INFORMATION: Description of Artificial
      Sequence:probe sequence

<400> SEQUENCE: 88
gtaagtaggc gcagc                                                        15

<210> SEQ ID NO 89
<211> LENGTH: 15
<212> TYPE: DNA
<213> ORGANISM: Artificial Sequence
<220> FEATURE:
<223> OTHER INFORMATION: Description of Artificial
      Sequence:probe sequence

<400> SEQUENCE: 89

```
gtaagtaggc gcggc                                                    15

<210> SEQ ID NO 90
<211> LENGTH: 12
<212> TYPE: DNA
<213> ORGANISM: Artificial Sequence
<220> FEATURE:
<223> OTHER INFORMATION: Description of Artificial
      Sequence:probe sequence

<400> SEQUENCE: 90
ggttcccgag cg                                                       12
```